United States Patent
Adlem et al.

(10) Patent No.: US 10,465,115 B2
(45) Date of Patent: Nov. 5, 2019

(54) CINNAMIC ACID DERIVATIVES

(71) Applicant: MERCK PATENT GMBH, Darmstadt (DE)

(72) Inventors: Kevin Adlem, Bournemouth (GB); Alex Davis, Chandlers Ford (GB); Hassan Arasi, Eastleigh (GB); Joseph Sargent, Southampton (GB); Rachel Tuffin, Chandlers Ford (GB); Ian Charles Sage, Malvern (GB)

(73) Assignee: MERCK PATENT GMBH, Darmstadt (DE)

(*) Notice: Subject to any disclaimer, the term of this patent is extended or adjusted under 35 U.S.C. 154(b) by 0 days.

(21) Appl. No.: 16/062,942

(22) PCT Filed: Nov. 18, 2016

(86) PCT No.: PCT/EP2016/001942
§ 371 (c)(1),
(2) Date: Jun. 15, 2018

(87) PCT Pub. No.: WO2017/102053
PCT Pub. Date: Jun. 22, 2017

(65) Prior Publication Data
US 2018/0371318 A1 Dec. 27, 2018

(30) Foreign Application Priority Data

Dec. 17, 2015 (EP) ...................................... 1500928

(51) Int. Cl.
| | | |
|---|---|---|
| *C09K 19/56* | (2006.01) | |
| *C09K 19/30* | (2006.01) | |
| *C09K 19/20* | (2006.01) | |
| *C07C 69/734* | (2006.01) | |
| *C07F 7/18* | (2006.01) | |
| *C09K 19/34* | (2006.01) | |
| *G02F 1/1337* | (2006.01) | |
| *G02F 1/1341* | (2006.01) | |
| *C09K 19/04* | (2006.01) | |

(52) U.S. Cl.
CPC ........ *C09K 19/3068* (2013.01); *C07C 69/734* (2013.01); *C07F 7/1876* (2013.01); *C09K 19/20* (2013.01); *C09K 19/2014* (2013.01); *C09K 19/3066* (2013.01); *C09K 19/3402* (2013.01); *G02F 1/1341* (2013.01); *G02F 1/133788* (2013.01); *C09K 2019/0448* (2013.01); *C09K 2019/0466* (2013.01); *C09K 2019/3004* (2013.01); *C09K 2019/3416* (2013.01)

(58) Field of Classification Search
CPC ......... C09K 19/20; C09K 19/30; C09K 19/56
USPC ......... 445/24; 252/299.1, 0.01, 0.2, 0.3, 0.4, 252/0.5, 0.6, 0.61, 0.62, 0.63, 0.64, 0.65, 252/0.66, 0.67, 0.68, 0.7
See application file for complete search history.

(56) References Cited

U.S. PATENT DOCUMENTS

| | | |
|---|---|---|
| 5,965,761 A | 10/1999 | Buchecker |
| 6,335,409 B1 | 1/2002 | Herr |
| 9,249,355 B2 | 2/2016 | Archetti |
| 9,868,904 B2 | 1/2018 | Graziano |
| 2004/0142116 A1 | 7/2004 | Nishikawa |
| 2011/0105700 A1* | 5/2011 | Akiike .................. C08G 77/38 525/449 |
| 2015/0232599 A1* | 8/2015 | Kitagawa .............. C08F 222/14 526/318.1 |
| 2017/0068031 A1 | 3/2017 | Yoshizawa |

FOREIGN PATENT DOCUMENTS

| | | |
|---|---|---|
| EP | 163552 A2 | 3/1997 |
| EP | 1524308 A1 | 4/2005 |
| KR | 100784460 B1 * | 12/2007 |
| WO | 2012038026 A1 | 3/2012 |
| WO | 2012104008 A1 | 8/2012 |
| WO | 2015182704 A1 | 12/2015 |

OTHER PUBLICATIONS

Search report in PCT/EP2016/001942 dated Jun. 22, 2017.
Hui-Xiong Dai et al: "Pd(II)-Catalyzed ortho- or meta-C—H Olefination of Phenol Derivatives", Journal of the American Chemical Society, vol. 135, No. 20, May 22, 2013 (May 22, 2013), US, pp. 7567-7571, XP055387665, ISSN: 0002-7863.

* cited by examiner

*Primary Examiner* — Christopher M Raabe
(74) *Attorney, Agent, or Firm* — Millen, White, Zelano and Branigan, P.C.

(57) ABSTRACT

The invention relates to cinnamic acid derivatives of formula S

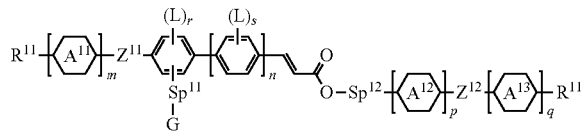

wherein the radicals have the meaning indicated in claim 1, to a process for their preparation and their use as self assembling photoalignment agent in liquid crystal mixtures. The invention further relates to a process for the fabrication of a liquid crystal (LC) display device with homogeneous alignment by photoaligning a liquid crystal mixture with positive or negative dielectric anisotropy comprising one or more compounds of formula S and optionally a polymerizable compound, to the liquid crystal mixture comprising the self assembling photoaligning agent and optionally the polymerizable compound and to the LC display produced by said process.

21 Claims, No Drawings

CINNAMIC ACID DERIVATIVES

The invention relates to cinnamic acid derivatives, a process for their preparation and their use as self assembling photoalignment agent in liquid crystal mixtures. The invention further relates to liquid crystal mixtures comprising said cinnamic acid derivatives and optionally a polymerisable compound, to a process for the fabrication of a liquid crystal (LC) display device with homogeneous alignment by photoaligning the cinnamic acid derivative after its self assembly, and to the LC display produced by said process.

Liquid-crystalline media have been used for decades in electro-optical displays (liquid crystal displays—LCD) for the purpose of information display. The liquid crystal displays (LC displays) used at present are often those of the TN ("twisted nematic") type. However, these have the disadvantage of a strong viewing-angle dependence of the contrast.

In addition, so-called VA ("vertically aligned") displays are known which have a broader viewing angle. The LC cell of a VA display contains a layer of an LC medium between two transparent electrodes, where the LC medium usually has a negative value of the dielectric (DC) anisotropy. In the switched-off state, the molecules of the LC layer are aligned perpendicular to the electrode surfaces (homeotropically) or have a tilted planar (homogeneous) alignment. On application of an electrical voltage to the two electrodes, a realignment of the LC molecules parallel to the electrode surfaces takes place. Furthermore, so-called IPS ("in plane switching") displays and later, FFS ("fringe-field switching") displays have been reported (see, inter alia, S. H. Jung et al., Jpn. J. Appl. Phys., Volume 43, No. 3, 2004, 1028), which contain two electrodes on the same substrate, one of which is structured in a comb-shaped manner and the other is unstructured. A strong, so-called "fringe field" is thereby generated, i.e. a strong electric field close to the edge of the electrodes, and, throughout the cell, an electric field which has both a strong vertical component and also a strong horizontal component. FFS displays have a low viewing-angle dependence of the contrast. FFS displays usually contain an LC medium with positive dielectric anisotropy, and an alignment layer, usually of polyimide, which provides planar alignment to the molecules of the LC medium.

Furthermore, FFS displays have been disclosed (see S. H. Lee et al., Appl. Phys. Lett. 73(20), 1998, 2882-2883 and S. H. Lee et al., Liquid Crystals 39(9), 2012, 1141-1148), which have similar electrode design and layer thickness as FFS displays, but comprise a layer of an LC medium with negative dielectric anisotropy instead of an LC medium with positive dielectric anisotropy. The LC medium with negative dielectric anisotropy shows a more favourable director orientation that has less tilt and more twist orientation compared to the LC medium with positive dielectric anisotropy; as a result these displays have a higher transmission.

A further development are the so-called PS (polymer sustained) or PSA (polymer sustained alignment) displays, for which the term "polymer stabilised" is also occasionally used. The PSA displays are distinguished by the shortening of the response times without significant adverse effects on other parameters, such as, in particular, the favourable viewing-angle dependence of the contrast.

In these displays, a small amount (for example 0.3% by weight, typically <1% by weight) of one or more polymerisable compound(s) is added to the LC medium and, after introduction into the LC cell, is polymerised or crosslinked in situ, usually by UV photopolymerisation, between the electrodes with or without an applied electrical voltage. The addition of polymerisable mesogenic or liquid-crystalline compounds, also known as reactive mesogens or "RMs", to the LC mixture has proven particularly suitable. PSA technology has hitherto been employed principally for LC media having negative dielectric anisotropy.

Unless indicated otherwise, the term "PSA" is used below as representative of PS displays and PSA displays.

In the meantime, the PSA principle is being used in diverse classical LC displays. Thus, for example, PSA-VA, PSA-OCB, PSA-IPS, PSA-FFS and PSA-TN displays are known. The polymerisation of the polymerisable compound(s) preferably takes place with an applied electrical voltage in the case of PSA-VA and PSA-OCB displays, and with or without an applied electrical voltage in the case of PSA-IPS displays. As can be demonstrated in test cells, the PS(A) method results in a 'pretilt' in the cell. In the case of PSA-OCB displays, for example, it is possible for the bend structure to be stabilised so that an offset voltage is unnecessary or can be reduced. In the case of PSA-VA displays, the pretilt has a positive effect on the response times. A standard MVA or PVA pixel and electrode layout can be used for PSA-VA displays. In addition, however, it is also possible, for example, to manage with only one structured electrode side and no protrusions, which significantly simplifies production and at the same time results in very good contrast at the same time as very good light transmission.

PSA-VA displays are described, for example, in JP 10-036847 A, EP 1 170 626 A2, U.S. Pat. Nos. 6,861,107, 7,169,449, US 2004/0191428 A1, US 2006/0066793 A1 and US 2006/0103804 A1. PSA-OCB displays are described, for example, in T.-J-Chen et al., Jpn. J. Appl. Phys. 45, 2006, 2702-2704 and S. H. Kim, L.-C-Chien, Jpn. J. Appl. Phys. 43, 2004, 7643-7647. PSA-IPS displays are described, for example, in U.S. Pat. No. 6,177,972 and Appl. Phys. Lett. 1999, 75(21), 3264. PSA-TN displays are described, for example, in Optics Express 2004, 12(7), 1221. PSA-VA-IPS displays are disclosed, for example, in WO 2010/089092 A1.

Like the conventional LC displays described above, PSA displays can be operated as active-matrix or passive-matrix displays. In the case of active-matrix displays, individual pixels are usually addressed by integrated, non-linear active elements, such as, for example, transistors (for example thin-film transistors or "TFTs"), while in the case of passive-matrix displays, individual pixels are usually addressed by the multiplex method, both methods being known from the prior art.

In the prior art, polymerisable compounds of the following formula, for example, are used for PSA-VA:

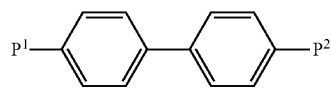

wherein $P^1$ and $P^2$ denote polymerisable groups, usually acrylate or methacrylate groups, as described, for example, in U.S. Pat. No. 7,169,449.

Below the polymer layer which induces the above mentioned pretilt, an orientation layer—usually a polyimide—provides the initial uniform alignment of the liquid crystal regardless of the polymer stabilisation step of the production process.

Rubbed polyimide has been used for a long time to align liquid crystals. However, the rubbing process causes a number of problems: mura, contamination, problems with static discharge, debris, etc. Hence, the effort for the production of a polyimide layer, treatment of the layer and improvement with bumps or polymer layers is relatively great. A simplifying technology which on the one hand reduces production costs and on the other hand helps to optimise the image quality (viewing-angle dependence, contrast, response times) would therefore be desirable.

In the prior art, a mechanism of orienting polymers comprising a suitable chromophore is described where photomodification is initiated by irradiation with linear polarised light resulting in a preferred molecular configuration (cf. U.S. Pat. No. 5,389,698). Based on these findings, photoalignment was developed, which is a technology for achieving liquid crystal alignment that avoids rubbing by such a light-induced orientational ordering of the alignment surface. This can be achieved through the mechanisms of photodecomposition, photodimerisation, and photoisomerisation (N. A. Clark et al. Langmuir 2010, 26(22), 17482-17488, and literature cited therein) by means of linear polarised light.

Photocrosslinkable cinnamates are known from the prior art, e.g. of the following structure

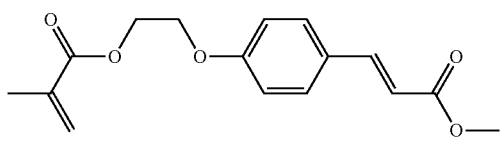 [SMILES: C=C(C)C(=O)OCCOc1ccc(/C=C/C(=O)OC)cc1]

as disclosed in EP0763552. From such compounds, polymers can be obtained, for example the following

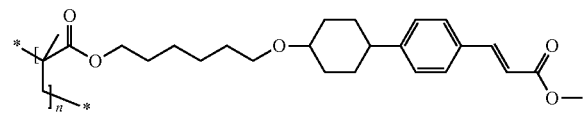 [SMILES: *CC(*)(C)C(=O)OCCCCCCOC1CCC(c2ccc(/C=C/C(=O)OC)cc2)CC1]

which was used in photoalignment as disclosed in WO9949360 where a polarisation-sensitive photopolymer is oriented by irradiation with linearly polarised light, which can be used as orientation layer of liquid crystals when the orientation is performed on a suitable substrate. A disadvantage of orientation layers obtained by this process is that they give lower voltage holding ratios than polyimides.

Thus, ideally still a suitably derivatised polyimide layer is required that comprises the photoreactive group. A further improvement would be to avoid the use of polyimide at all without sacrificing high VHR values. For VA displays this was achieved by adding a self alignment agent to the LC that induces alignment in situ by a self assembling mechanism followed by a polymerisation process known from PSA displays, as disclosed in WO 2012/104008 and WO 2012/038026.

Siloxanes and polysiloxanes derived thereof were proposed as alignment material for displays (e.g. WO 2014/021174 A1, WO 2008/044644 and WO 2009/025388). However, the substrates have to be coated with these materials before assembly of the display.

N. A. Clark et al., Langmuir 2010, 26(22), 17482-17488 have shown that it is possible to self assemble a compound of the following structure

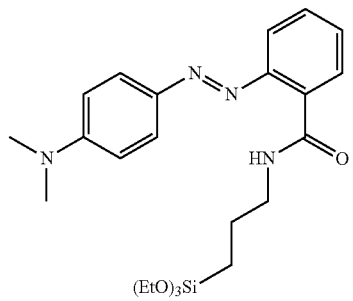

onto a substrate to give a monolayer that is able to be photoaligned to induce homogeneous alignment of a liquid crystal. However, a separate step of self assembly before manufacture of the LC cell was performed and reversibility of the alignment upon exposure to light was reported. Furthermore, due to their intense chromaticity their application in displays for monitor or TV is restricted.

It is an object of the present invention to provide a photoalignable, self assembling material that does not have the disadvantages of the material known form prior art.

It is a further object of this invention to simplify the production process of an LC display by providing a method to align liquid crystals without the use of polyimide and without giving up the advantages of IPS technology, such as relatively short response times, good viewing-angle dependence and high contrast.

Surprisingly it was found that it is possible to manufacture a liquid crystal display without a polyimide alignment layer by interposing a liquid crystal mixture between two substrates, the liquid crystal mixture comprising liquid crystal molecules, one or more self assembling photoalignment agents of formula S below, and one or more polymerisable compounds of formula P below; irradiating the liquid crystal mixture with linearly polarised light causing photoalignment of the liquid crystal; and curing the polymerisable compound in the liquid crystal mixture by irradiation with ultraviolet light.

Accordingly, the present invention relates to compounds of formula S

S

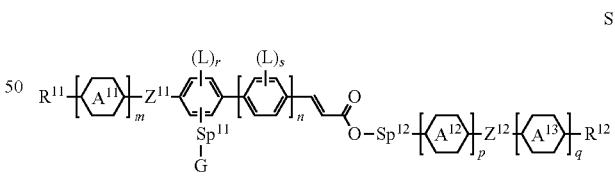

wherein $R^{11}$ and $R^{12}$ identically or differently denote P, P-Sp-, H, F, Cl, Br, I, —CN, —NO$_2$, —NCO, —NCS, —OCN, —SCN, SF$_5$ or straight-chain or branched alkyl having 1 to 25 C atoms, in which, in addition, one or more non-adjacent CH$_2$ groups may each be replaced, independently of one another, by —C(R$^0$)=C(R$^{00}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN, P or P-Sp-, P denotes a polymerisable group,
Sp,
$Sp^{11}$, $Sp^{12}$ denotes a spacer group or a single bond,
$A^{11}$, $A^{12}$ and
$A^{13}$ on each occurrence, identically or differently, denote an aromatic, alicyclic or heterocyclic group, preferably having 4 to 25 ring atoms, which may also contain fused rings, and which is unsubstituted, or mono- or polysubstituted by L,
$Z^{11}$, $Z^{12}$ on each occurrence, identically or differently, denote —O—, —S—, —CO—, —CO—O—, —OCO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —C≡C—, —CH=CH—COO—, —OCO—CH=CH—, $CR^0R^{00}$ or a single bond,
$R^0$ and $R^{00}$ each, independently of one another, denote H or alkyl having 1 to 12 C atoms,
n1 is 1, 2, 3 or 4,
m is 0, 1 or 2,
n is 0 or 1
p is 0 or 1
q is 0, 1 or 2
m+n+p+q is ≤4
r on each occurrence, identically or differently, is 0, 1, 2 or 3,
s on each occurrence, identically or differently, is 0, 1, 2, 3, or 4,
L P, P-Sp-, OH, CH$_2$OH, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may be replaced by F, Cl, P or P-Sp-,
P and Sp have the meanings indicated above,
$Y^1$ denotes halogen,
$R^x$ denotes P, P-Sp-, H, halogen, straight-chain, branched or cyclic alkyl having 1 to 25 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P or P-Sp-, an optionally substituted aryl or aryloxy group having 6 to 40 C atoms, or an optionally substituted heteroaryl or heteroaryloxy group having 2 to 40 C atoms.
G denotes OH or Si(OR$^{13}$)$_3$,
$R^{13}$ denotes straight chain or branched alkyl having 1 to 6 C atoms.

Further the present invention relates to liquid crystal mixtures comprising one or more compounds of formula S.

The present invention further relates to a process for the fabrication of an LC display device with homogeneous alignment, preferably of the IPS or FFS type, by photoaligning a liquid crystal mixture inside an LC cell having at least one substrate, preferably two substrates and at least two electrodes, where at least one substrate is transparent to light and at least one substrate has one or two electrodes, comprising at least the process steps of:
providing a first substrate which includes a pixel electrode and a common electrode;
providing a second substrate, the second substrate being disposed opposite to the first substrate;
interposing a liquid crystal mixture between the first substrate and the second substrate, the liquid crystal mixture comprising liquid crystal molecules, one or more self assembling photoalignment agents of formula S above and optionally one or more polymerisable compounds of formula P below;
irradiating the liquid crystal mixture with linearly polarised ultraviolet light or linearly polarised visible light causing photoalignment of the liquid crystal;
curing the polymerisable compounds of the liquid crystal mixture by irradiation with ultraviolet light.

In a preferred embodiment the linearly polarised light is ultraviolet light which enables simultaneous photoalignment of the self assembling photoalignment agent and photocuring of the polymerisable compound.

The present invention further relates to the use of the liquid crystal mixtures according to the invention for the fabrication of a liquid crystal display.

The present invention further relates to LC displays fabricated by a process described above.

A self assembling photoalignment agent (SAPA) according to the present invention is a compound comprising at least one polar lateral group and at least one photoreactive group. Considering the investigations for this invention it appears that the polar lateral group interacts with the substrate surface thus enabling the SAPA to phase separate from the LC mixture after filling of the LC cell. According to this opinion, the SAPA forms a layer on the substrate which can be photoaligned with linearly polarised UV light. The liquid crystal follows the orientation of the aligned SAPA to give uniform planar alignment across the whole display.

According to the present application, the term "linearly polarised light" means light, which is at least partially linearly polarized. Preferably, the aligning light is linearly polarized with a degree of polarization of more than 5:1. Wavelengths, intensity and energy of the linearly polarised light are chosen depending on the photosensitivity of the photoalignable material. Typically, the wavelengths are in the UV-A, UV-B and/or UV-C range or in the visible range. Preferably, the linearly polarised light comprises light of wavelengths less than 450 nm, more preferably less than 420 nm.

The photoalignment process according to the present invention causes the SAPA of formula S to undergo a photochemical reaction under irradiation with linearly polarised light of appropriate wavelength. This photochemical reaction is an angle-dependent process, resulting eventually in the photoselection of SAPA orientations that are preferentially perpendicular or parallel to the polarization of the actinic light and with orientational anisotropy capable of aligning LCs.

The wavelength region of the polarised light is preferably chosen so as to match the absorption spectrum of the SAPA.

In case the alignment is reversible, for example under the influence of heat or light, it is desirable to fix the alignment of the SAPA and the LC. Surprisingly it was found that it is possible to fix the alignment by photopolymerising a polymerisable compound of formula P described below, with UV light inside the cell after or during the photoalignment step. As a result, the homogeneous alignment of the LC is irreversible and stable towards heat or light.

The compounds of formula S are preferably selected from the following sub-formulae

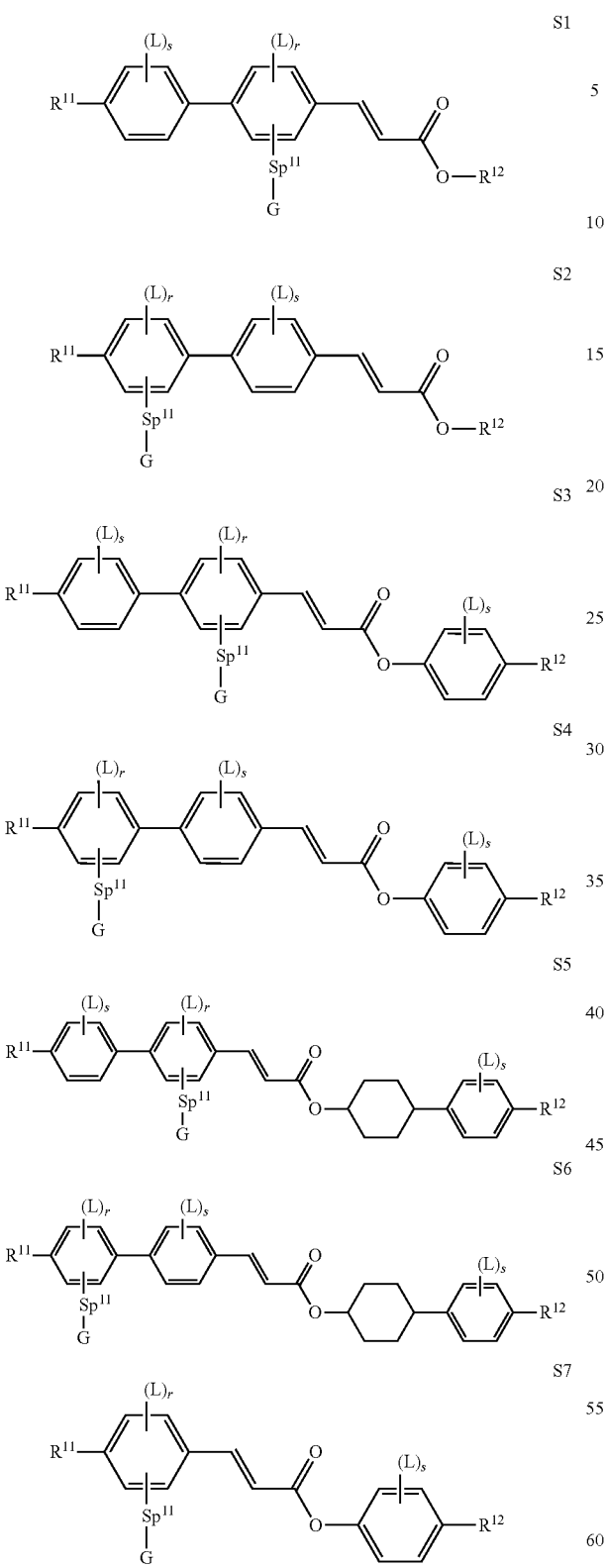
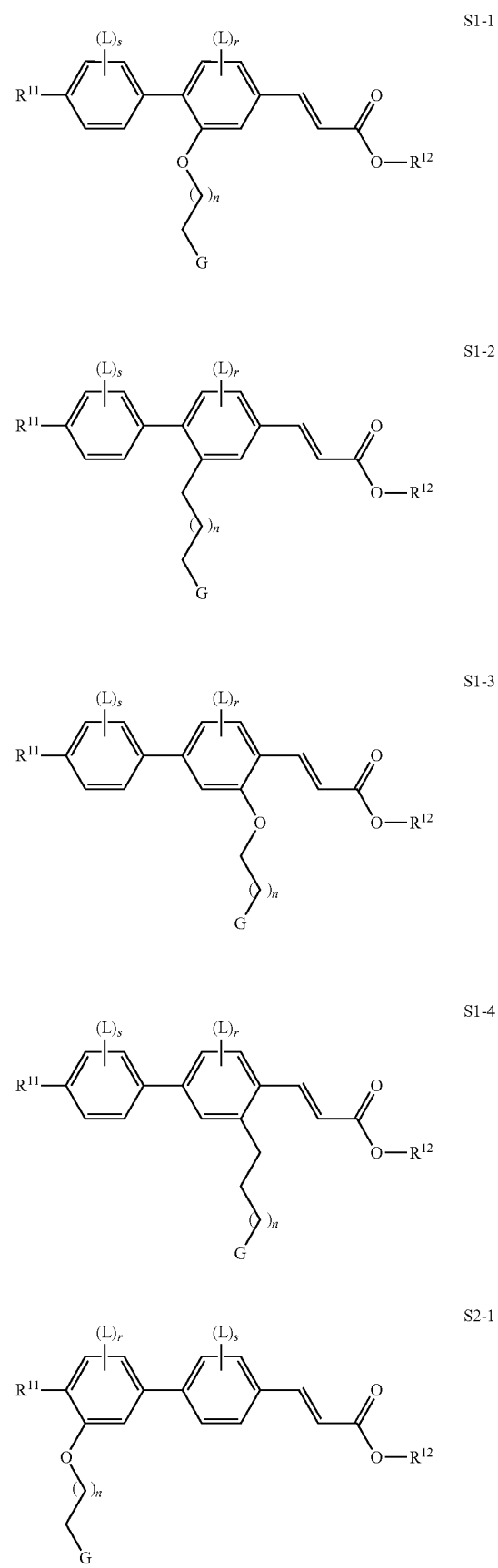
Wherein the radicals and parameters have the meaning indicated above.
Particularly preferred compounds of formulae S1 to S7 are selected from the following sub-formulae

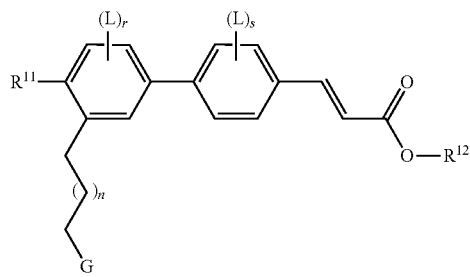
S2-2
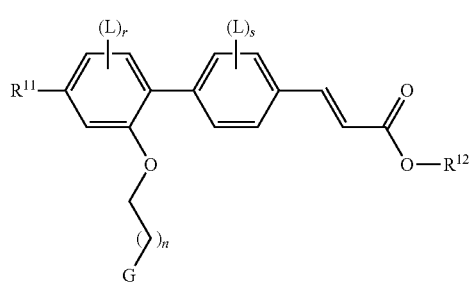
S2-3
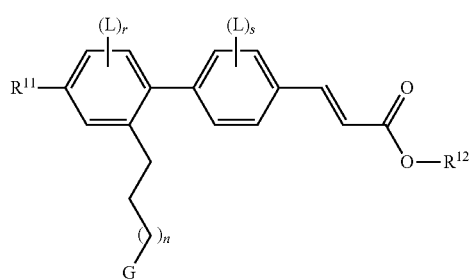
S2-4
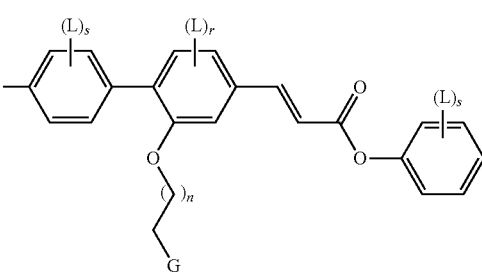
S3-1
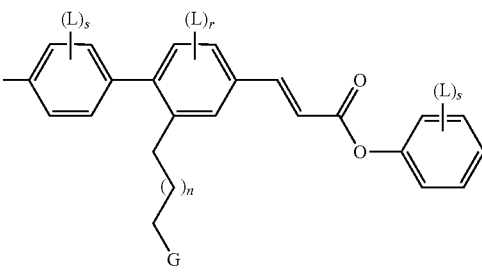
S3-2
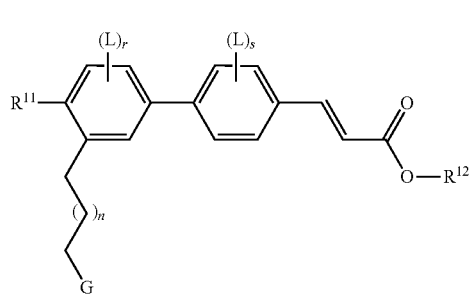
S3-3
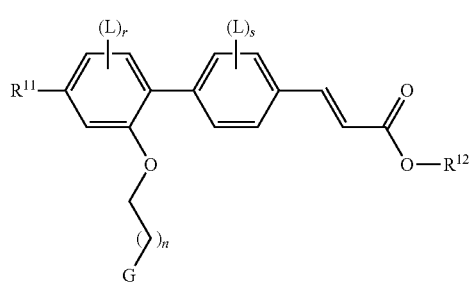
S3-4
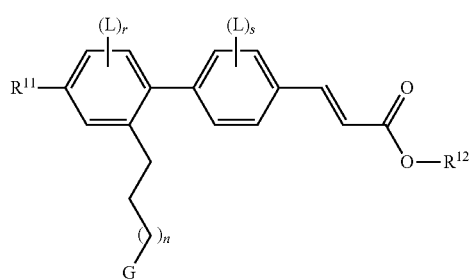
S4-1
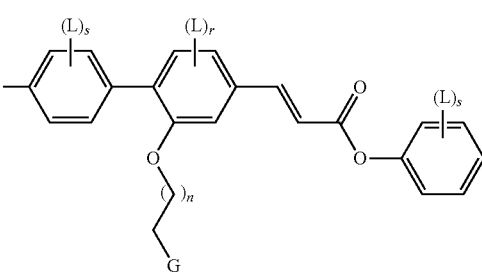
S4-2
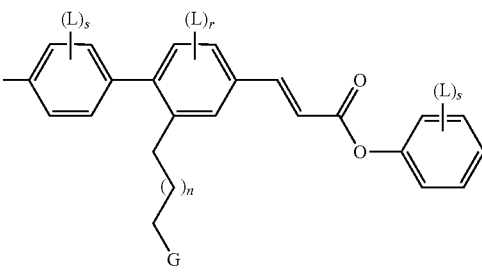
S4-3

-continued

S4-4
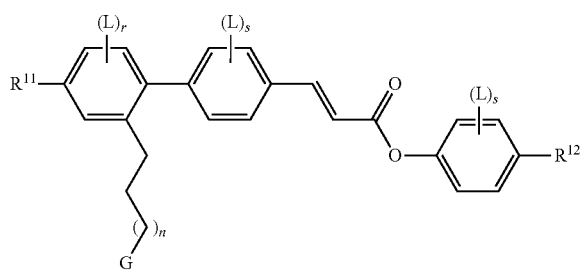

S5-1
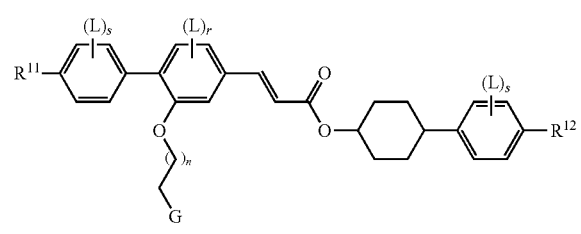

S5-2
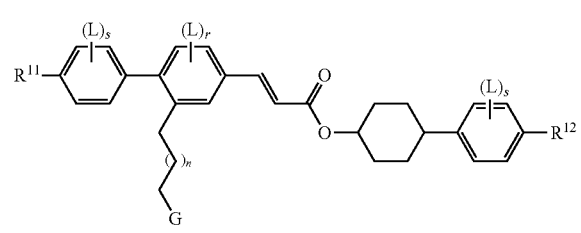

S5-3
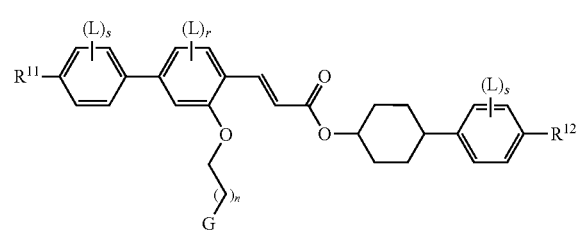

S5-4
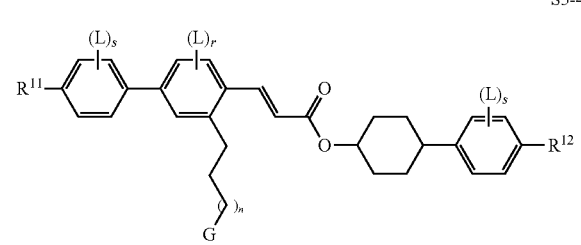

S6-1
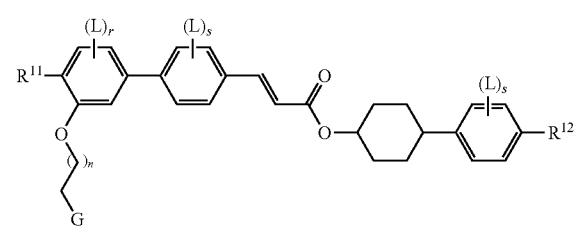

S6-2
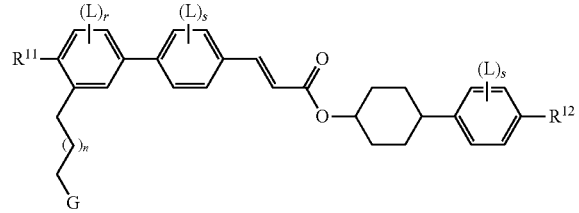

S6-3
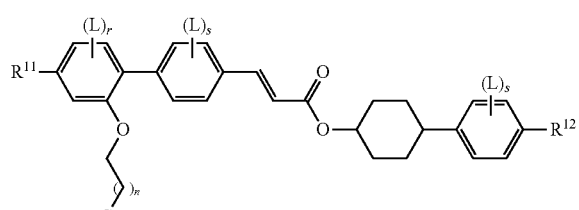

S6-4
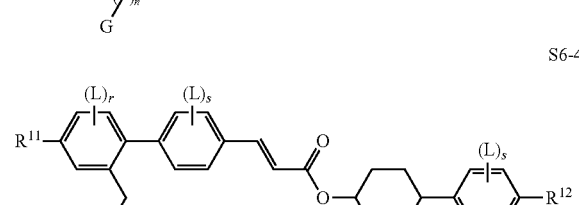

S7-1
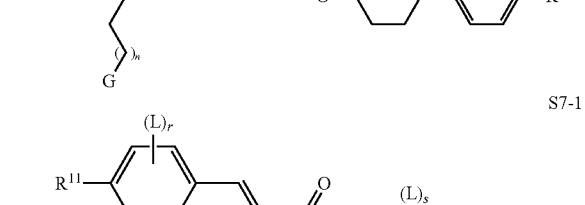

S7-2
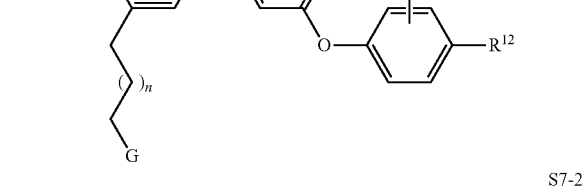

wherein $R^{11}$, $R^{12}$ and G, L and s have the meaning indicated above, n is an integer from 1 to 11, and preferably G denotes $Si(OR^{13})_3$.

In a first preferred embodiment $R^{11}$ and $R^{12}$ in compounds of formula S each, identically or differently, denote alkyl with 1 to 8 C atoms.

In a second preferred embodiment one of $R^{11}$ and $R^{12}$ in compounds of formula S denotes alkyl with 1 to 8 C atoms and the other of $R^{11}$ and $R^{12}$ denotes P-Sp.

In a third preferred embodiment $R^{11}$ and $R^{12}$ in compounds of formula S each, identically or differently, denote P-Sp.

Preferably, P denotes acrylate or methacrylate.

Sp preferably has one of the preferred meanings indicated below for formula P and particularly preferably denotes straight chain alkylene with 2 to 12 C atoms.

The compounds of formula S can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

Compounds of formula S are preferably synthesised as exemplified in scheme 1 below.

lates, preferably formed in situ by reaction with sodium hydride. Using terminal diols gives hydroxy ethers (6). The cinnamate moiety is preferably made by Heck reaction of aryl bromides or iodides (5, 6) with suitable acrylic acid esters, such as ethyl acrylate to give cinnamates 7. Phenols (5) can be alkylated with terminal alkenyl halides, e.g. allyl bromide, to give ethers 8 which can be hydrosilylated with trialkoxysilanes in the presence of e.g. Karstedt's catalyst (J. Stein et al., *J. Am. Chem. Soc.* 1999, 121, 3693-3703) to give compounds 9.

In a preferred embodiment, the liquid crystal mixture additionally comprises one or more polymerisable compounds of formula P,

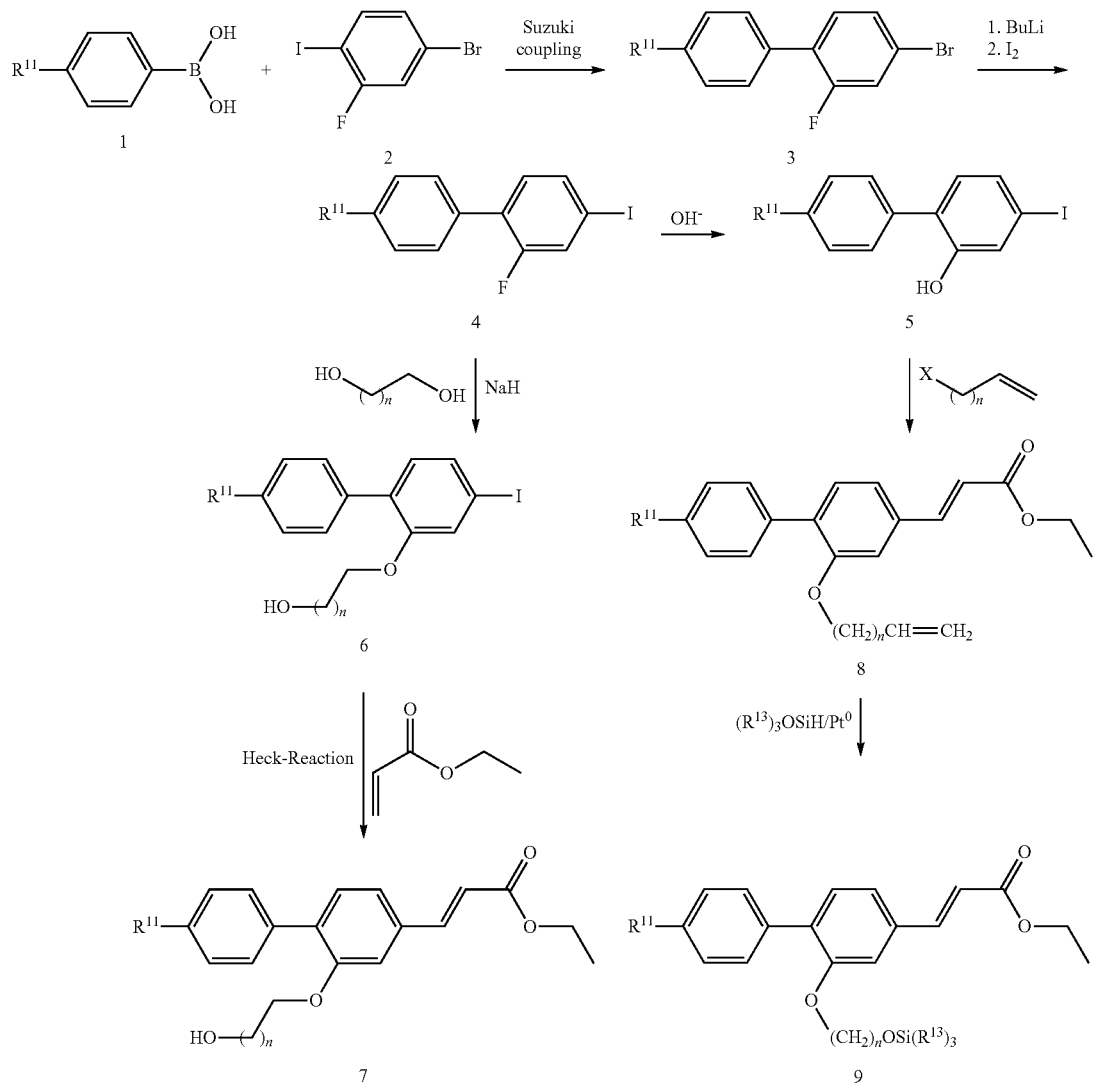

Preferred intermediates for the synthesis of compounds of formula S according to the present invention are fluoroaromatic compounds as for example compound 4 which can be synthesised following standard transformations as shown in scheme 1. The fluorine atom can be replaced nucleophilically by either hydroxide to give phenols (5) or by alcoho- $$P^a\text{-}(Sp^a)_{s1}\text{-}A^2\text{-}(Z^a\text{-}A^1)_{n2}\text{-}(Sp^b)_{s2}\text{-}P^b \quad\quad P$$

wherein the individual radicals have the following meanings:

$P^a$, $P^b$ each, independently of one another, denote a polymerisable group,

Sp$^a$, Sp$^b$ on each occurrence, identically or differently, denote a spacer group, s1, s2 each, independently of one another, denote 0 or 1, A$^1$, A$^2$ each, independently of one another, denote a radical selected from the following groups:
  a) the group consisting of trans-1,4-cyclohexylene, 1,4-cyclohexenylene and 4,4'-bicyclohexylene, wherein, in addition, one or more non-adjacent CH$_2$ groups may be replaced by —O— and/or —S— and wherein, in addition, one or more H atoms may be replaced by F,
  b) the group consisting of 1,4-phenylene and 1,3-phenylene, wherein, in addition, one or two CH groups may be replaced by N and wherein, in addition, one or more H atoms may be replaced by L,
  c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may also be mono- or polysubstituted by L,
  d) the group consisting of saturated, partially unsaturated or fully unsaturated, and optionally substituted, polycyclic radicals having 5 to 20 cyclic C atoms, one or more of which may, in addition, be replaced by heteroatoms, preferably selected from the group consisting of

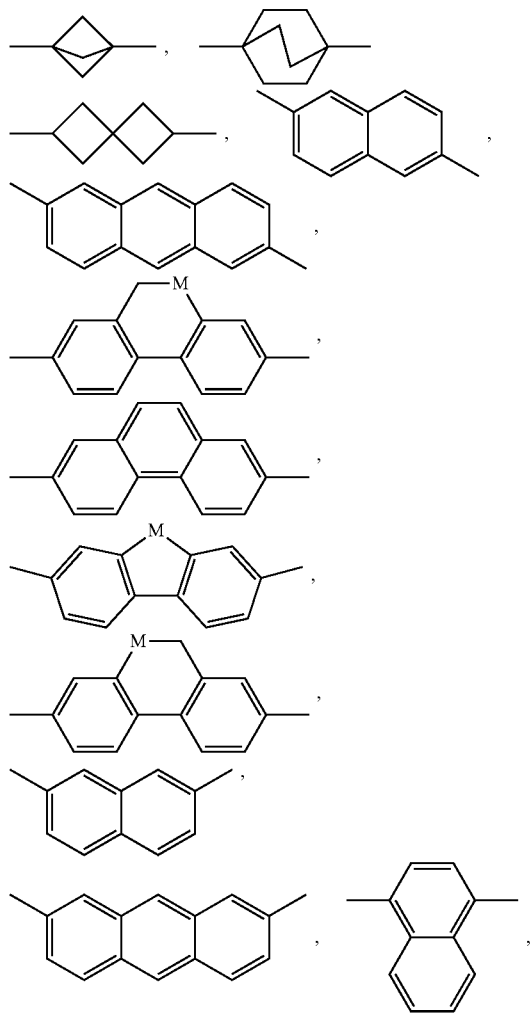

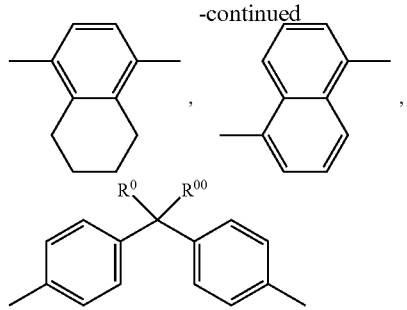

where, in addition, one or more H atoms in these radicals may be replaced by L, and/or one or more double bonds may be replaced by single bonds, and/or one or more CH groups may be replaced by N, n2 denotes 0, 1, 2 or 3, Z$^a$ in each case, independently of one another, denotes —CO—O—, —O—CO—, —CH$_2$O—, —OCH$_2$—, —CF$_2$O—, —OCF$_2$—, or —(CH$_2$)$_n$—, where n is 2, 3 or 4, —O—, —CO—, —C(R$^y$R$^z$)—, —CH$_2$CF$_2$—, —CF$_2$CF$_2$— or a single bond, L on each occurrence, identically or differently, denotes F, Cl, CN, SCN, SF$_5$ or straight-chain or branched, in each case optionally fluorinated, alkyl, alkoxy, alkylcarbonyl, alkoxycarbonyl, alkylcarbonyloxy or alkoxycarbonyloxy having 1 to 12 C atoms, R$^y$, R$^z$ each, independently of one another, denote H, F or straight-chain or branched alkyl having 1 to 12 C atoms, wherein, in addition, one or more H atoms may be replaced by F, M denotes —O—, —S—, —CH$_2$—, —CHY$^1$— or —CY$^1$Y$^2$—, and Y$^1$ and Y$^2$ each, independently of one another, have one of the meanings indicated above for R$^y$ or denote Cl or CN.

The polymerisable group P$^{a,b}$ is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or —C≡C— triple bond, and groups which are suitable for polymerisation with ring opening, such as, for example, oxetane or epoxide groups.

Preferred groups P$^{a,b}$ are selected from the group consisting of CH$_2$=CW$^1$—CO—O—, CH$_2$=CW$^1$—CO—,

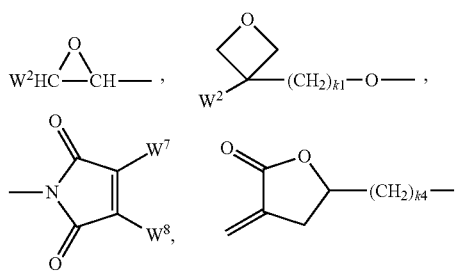

CH$_2$=CW$^2$—(O)$_{k3}$—,  CW$^1$=CH—CO—(O)$_{k3}$—,
CW$^1$=CH—CO—NH—,  CH$_2$=CW$^1$—CO—NH—,
CH$_3$—CH=CH—O—,  (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, CH$_2$=CH—(CO)$_{k1}$-Phe-(O)$_{k2}$—, Phe-CH=CH—, HOOC—, OCN— and W$^4$W$^5$W$^6$Si—, wherein W$^1$ denotes H, F, Cl, CN, CF$_3$, phenyl or alkyl having 1 to 5 C atoms, in particular H, F, Cl or CH$_3$, W$^2$ and W$^3$ each, independently of one another, denote H or alkyl having 1 to 5 C atoms, in particular H, methyl, ethyl or n-propyl, W$^4$, W$^5$ and W$^6$ each, independently of one another, denote Cl, oxaalkyl or oxa-carbonyl-alkyl having 1 to 5 C atoms, W$^7$ and W$^8$ each, independently of one another, denote H, Cl or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Particularly preferred groups $P^{a,b}$ are selected from the group consisting of CH$_2$=CW$^1$—CO—O—, in particular CH$_2$=CH—CO—O—, CH$_2$=C(CH$_3$)—CO—O— and CH$_2$=CF—CO—O—, furthermore CH$_2$=CH—O—, (CH$_2$=CH)$_2$CH—O—CO—, (CH$_2$=CH)$_2$CH—O—,

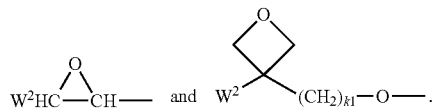

Very particularly preferred groups $P^{a,b}$ are selected from the group consisting of acrylate, methacrylate, fluoroacrylate, furthermore vinyloxy, chloroacrylate, oxetane and epoxide groups, and of these preferably an acrylate or methacrylate group.

Preferred spacer groups $Sp^{a,b}$ are selected from the formula Sp"-X", so that the radical $P^{a/b}$-$Sp^{a/b}$- conforms to the formula $P^{a/b}$-Sp"-X"—, where Sp" denotes alkylene having 1 to 20, preferably 1 to 12, C atoms, which is optionally mono- or polysubstituted by F, Cl, Br, I or CN and wherein, in addition, one or more non-adjacent CH$_2$ groups may each be replaced, independently of one another, by —O—, —S—, —NH—, —N(R$^0$)—, —Si(R$^{00}$R$^{000}$)—, —CO—, —CO—O—, —O—CO—, —O—CO—O—, —S—CO—, —CO—S—, —N(R$^0$)—CO—O—, —O—CO—N(R$^{00}$)—, —N(R$^{00}$)—CO—N(R$^{00}$)—, —CH=CH— or —C≡C— in such a way that O and/or S atoms are not linked directly to one another, X" denotes —O—, —S—, —CO—, —CO—O—, —O—CO—, —O—CO—O—, —CO—N(R$^{00}$)—, —N(R$^{00}$)—CO—, —N(R$^{00}$)—CO—N(R$^{00}$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^3$=CY$^4$—, —C≡C—, —CH=CH—CO—O—, —O—CO—CH=CH— or a single bond, R$^0$, R$^{00}$ and R$^{000}$ each, independently of one another, denote H or alkyl having 1 to 12 C atoms, and Y$^3$ and Y$^4$ each, identically or differently, denote H, F, Cl or CN.

X" is preferably —O—, —S—, —CO—, —C(O)O—, —OC(O)—, —O—C(O)O—, —CO—NR$^0$—, —NR$^0$—CO—, —NR$^0$—CO—NR$^0$— or a single bond.

Typical spacer groups Sp" are, for example, —(CH$_2$)$_{p1}$—, —(CH$_2$CH$_2$O)$_{q1}$—CH$_2$CH$_2$—, —CH$_2$CH$_2$—S—CH$_2$CH$_2$—, —CH$_2$CH$_2$—NH—CH$_2$CH$_2$— or —(SiR$^{00}$R$^{000}$—O)$_{p1}$—, wherein p1 is an integer from 1 to 12, q1 is an integer from 1 to 3, and R$^{00}$ and R$^{000}$ have the meanings indicated above.

Particularly preferred groups -Sp"-X"— are —(CH$_2$)$_{p1}$—, —(CH$_2$)$_{p1}$—O—, —(CH$_2$)$_{p1}$—O—CO—, —(CH$_2$)$_{p1}$—O—CO—O—, wherein p1 and q1 have the meanings indicated above.

Particularly preferred groups Sp" are, for example, in each case straight-chain ethylene, propylene, butylene, pentylene, hexylene, heptylene, octylene, nonylene, decylene, undecylene, dodecylene, octadecylene, ethylene-oxyethylene, methyleneoxybutylene, ethylenethioethylene, ethylene-N-methyliminoethylene, 1-methylalkylene, ethenylene, propenylene and butenylene.

Particularly preferred monomers of formula P are the following:

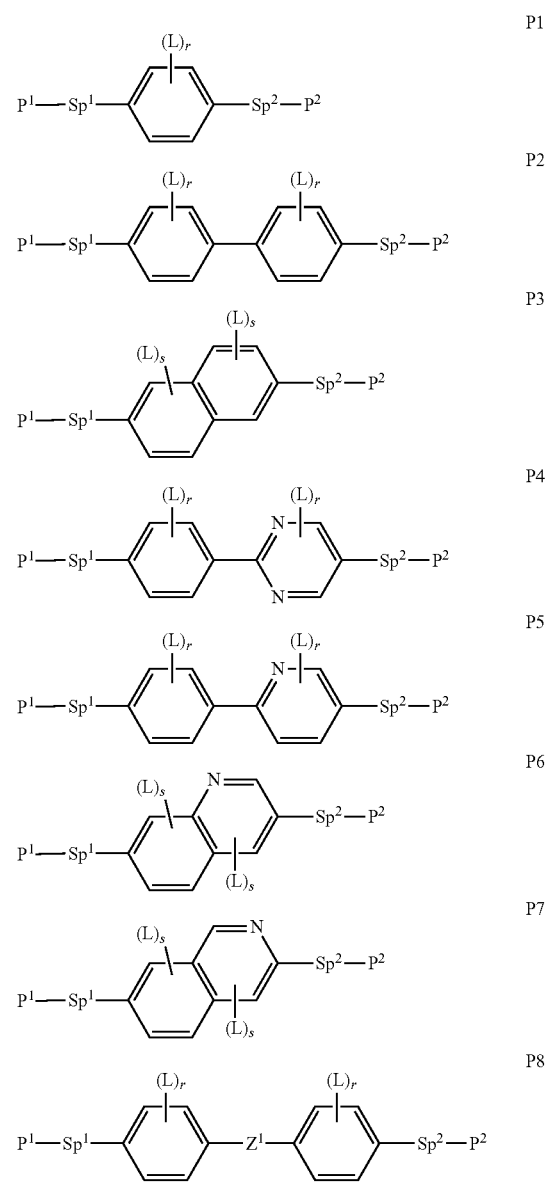

-continued
P9
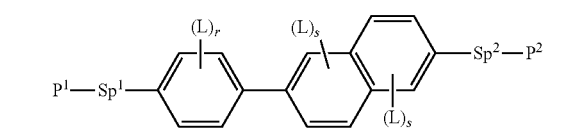
P10
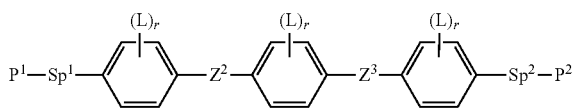
P11
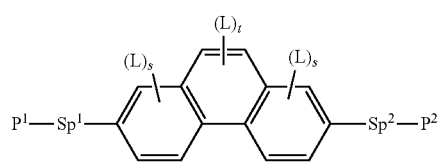
P12
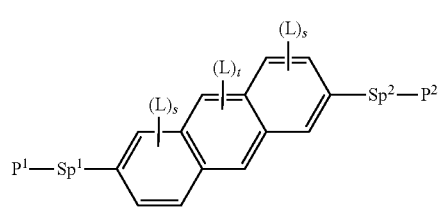
P13
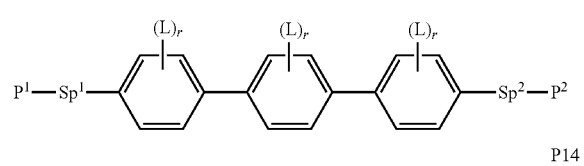
P14
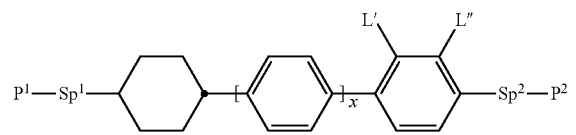
P15
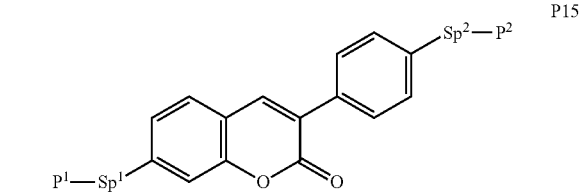
P16
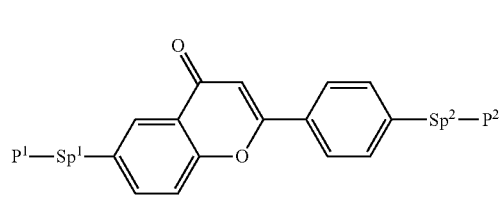
P17
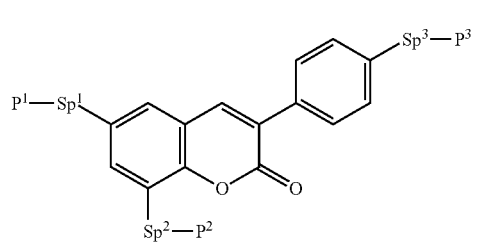
-continued
P18
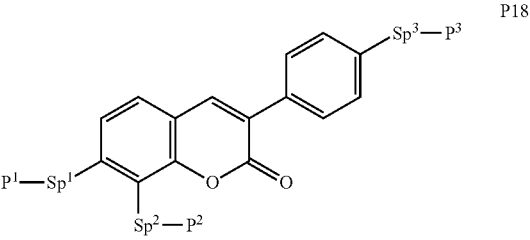
P19
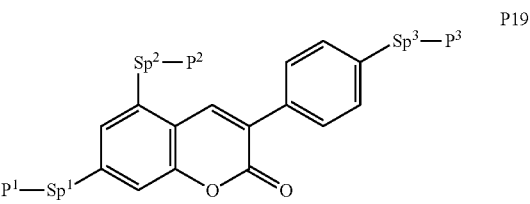
P20
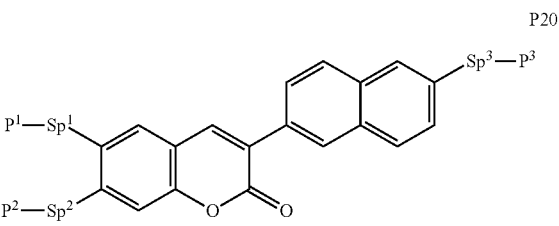
P21
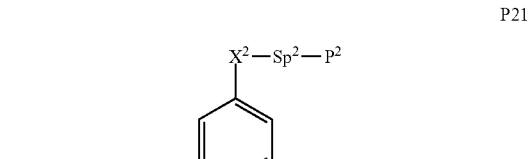
P22
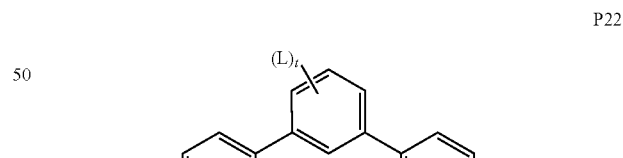
P23
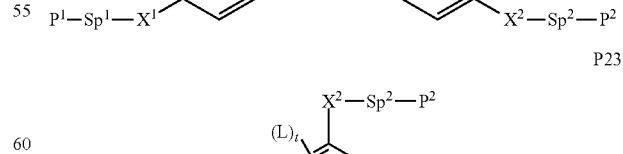

-continued

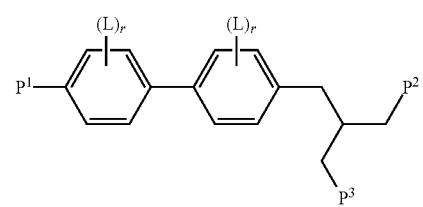
P24

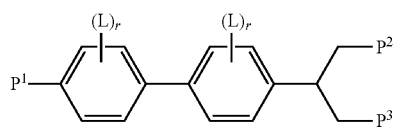
P25

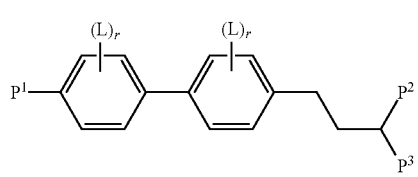
P26

P27

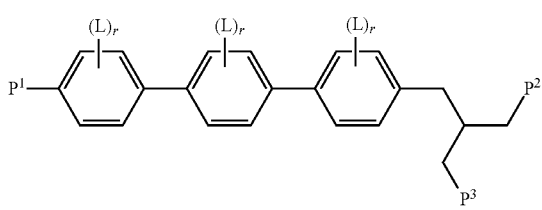
P28

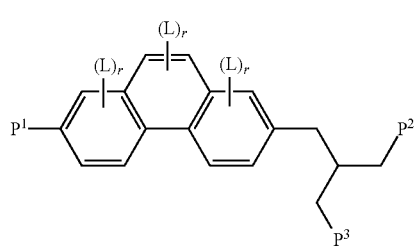
P29

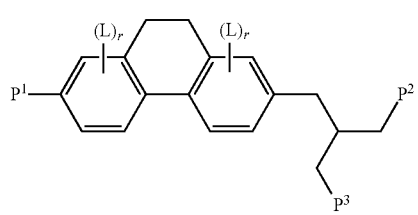
P30

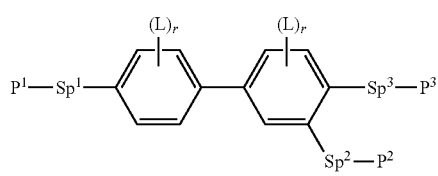
P31

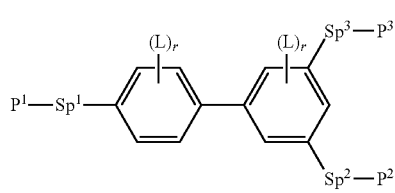

wherein the individual radicals have the following meanings:

P¹, P² and P³ each, independently of one another, denote a polymerisable group as defined for formula P, preferably an acrylate, methacrylate, fluoroacrylate, oxetane, vinyloxy or epoxide group, Sp¹, Sp² and Sp³ each, independently of one another, denote a single bond or a spacer group, preferably having one of the meanings indicated above and below for Sp$^a$, and particularly preferably —(CH$_2$)$_{p1}$—, —(CH$_2$)$_{p1}$—O—, —(CH$_2$)$_{p1}$—CO—O— or —(CH$_2$)$_{p1}$—O—CO—O—, wherein p1 is an integer from 1 to 12, and where the linking to the adjacent ring in the last-mentioned groups takes place via the O-atom, where, in addition, one or more of the radicals P¹-Sp¹-, P²—Sp²- and P³—Sp³- may denote a radical R$^{aa}$, with the proviso that at least one of the radicals P¹-Sp¹-, P²—Sp²- and P³—Sp³- present does not denote R$^{aa}$, R$^{aa}$ denotes H, F, Cl, CN or straight-chain or branched alkyl having 1 to 25 C atoms, wherein, in addition, one or more non-adjacent CH$_2$ groups may each be replaced, independently of one another, by C(R$^0$)=C(R$^{00}$)—, —C≡C—, —N(R$^0$)—, —O—, —S—, —CO—, —CO—O—, —O—CO—, —O—CO—O— in such a way that O and/or S atoms are not linked directly to one another, and wherein, in addition, one or more H atoms may be replaced by F, Cl, CN or P¹—Sp¹-, particularly preferably straight-chain or branched, optionally mono- or polyfluorinated alkyl, alkoxy, alkenyl, alkynyl, alkylcarbonyl, alkoxycarbonyl or alkylcarbonyloxy having 1 to 12 C atoms (where the alkenyl and alkynyl radicals have at least two C atoms and the branched radicals have at least three C atoms), R$^0$, R$^{00}$ each, independently of one another, denote H or alkyl having 1 to 12 C atoms, R$^y$ and R$^z$ each, independently of one another, denote H, F, CH$_3$ or CF$_3$, Z$^{p1}$ denotes —O—, —CO—, —C(R$^y$R$^z$)— or —CF$_2$CF$_2$—, Z$^{p2}$ and Z$^{p3}$ each, independently of one another, denote —CO—O—, —O—CO—, —CH$_2$O—, —OCH$_2$—, —CF$_2$O—, —OCF$_2$— or —(CH$_2$)$_{n3}$—, where n3 is 2, 3 or 4, L on each occurrence, identically or differently, denotes F, Cl, CN, SCN, SF$_5$ or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4,
s denotes 0, 1, 2 or 3,
t denotes 0, 1 or 2, and
x denotes 0 or 1.

In a particularly preferred embodiment of the present invention the LC mixture comprises one or more compounds or formula P10-1

P10-1 wherein the parameters are defined as described above and P¹ and P² preferably denote acrylate or methacrylate.

Particularly preferred compounds of formula P10-1 are selected from the group of the following subformulae

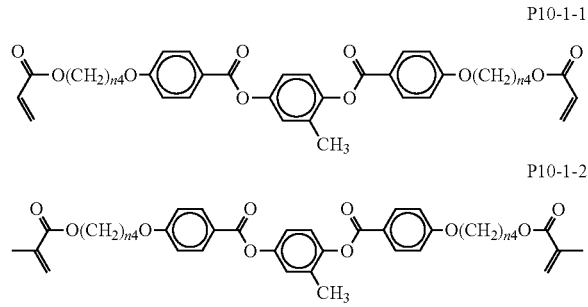

P10-1-1

P10-1-2 wherein each n4 denote independently of each other an integer between 2 and 10, preferably 3, 4, 5 or 6.

Suitable and preferred polymerisation methods are, for example, thermal or photopolymerisation, preferably photopolymerisation, in particular UV photopolymerisation. One or more initiators can optionally also be added here.

Suitable conditions for the polymerisation and suitable types and amounts of initiators are known to the person skilled in the art and are described in the literature. Suitable for free-radical polymerisation are, for example, the commercially available photoinitiators Irgacure651®, Irgacure184®, Irgacure907®, Irgacure369® or Darocure1173® (BASF SE). If an initiator is employed, its proportion is preferably 0.001 to 5% by weight, particularly preferably 0.001 to 1% by weight.

The polymerisable compounds according to the invention are also suitable for polymerisation without an initiator, which is associated with considerable advantages, such as, for example, lower material costs and, in particular, reduced contamination of the LC medium by possible residual amounts of the initiator or degradation products thereof. The polymerisation can thus also be carried out without addition of an initiator. The LC medium thus, in a preferred embodiment, comprises no polymerisation initiator.

The polymerisable component or the LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (BASF SE), such as, for example, Irganox® 1076. If stabilisers are employed, their proportion, based on the total amount of the RMs or the polymerisable component, is preferably 10-10,000 ppm, particularly preferably 50-500 ppm.

Besides the SAPA of formula S described above and the polymerisable compounds of formula P described above, the LC media for use in the LC displays according to the invention comprise an LC mixture ("host mixture") comprising one or more, preferably two or more, low-molecular-weight (i.e. monomeric or unpolymerised) compounds. The latter are stable or unreactive with respect to a polymerisation reaction or photoalignment under the conditions used for the polymerisation of the polymerisable compounds or photoalignment of the SAPA. In principle, a suitable host mixture is any dielectrically negative or positive LC mixture which is suitable for use in conventional VA, IPS or FFS displays.

Suitable LC mixtures are known to the person skilled in the art and are described in the literature. LC media for VA displays having negative dielectric anisotropy are described in EP 1 378 557 A1.

Suitable LC mixtures having positive dielectric anisotropy which are suitable for LCDs and especially for IPS displays are known, for example, from JP 07-181 439 (A), EP 0 667 555, EP 0 673 986, DE 195 09 410, DE 195 28 106, DE 195 28 107, WO 96/23 851, WO 96/28 521 and WO2012/079676.

Preferred embodiments of the liquid-crystalline medium having negative or positive dielectric anisotropy according to the invention are indicated below.

As already mentioned, the compounds of the general formula S and of the general formula P can be used in liquid-crystalline media. Thus, the present invention also relates to liquid-crystalline media comprising 2 to 40, preferably 4 to 30, components as further constituents besides one or more compounds of the formula P and one or more compounds of formula S according to the invention. These media particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, 1,3-dioxanes, 2,5-tetrahydropyrans, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolanes and substituted cinnamic acids. The 1,4-phenylene groups in these compounds may also be mono- or polyfluorinated.

Hence, the LC media for use in the LC displays according to the invention comprise an LC mixture ("host mixture") comprising one or more, preferably two or more mesogenic compounds and one or more compounds selected from compounds of the formula S and one or more compounds of formula P described above.

The media according to the invention preferably comprise from 0.01 to 10%, particularly preferably from 0.05 to 2.5% and most preferably from 0.1 to 0.5% of the compounds of the formula S according to the invention. The media preferably comprise one, two or three, more preferably one or two and most preferably one compound of the formula S according to the invention.

The media according to the invention preferably comprise from 0.01 to 10%, particularly preferably from 0.05 to 7.5% and most preferably from 2 to 5% of the compounds of the formula P according to the invention. The media preferably comprise one, two or three, more preferably one or two and most preferably one compound of the formula P according to the invention.

The LC host mixture is preferably a nematic LC mixture, and preferably does not have a chiral LC phase.

In one preferred embodiment of the present invention the LC medium contains an LC host mixture with negative dielectric anisotropy. Preferred embodiments of such an LC medium, and the corresponding LC host mixture, are those of sections a)-z) below:

a) LC medium which comprises one or more compounds of the formulae CY and/or PY:

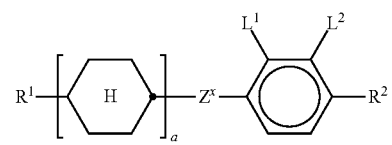

CY

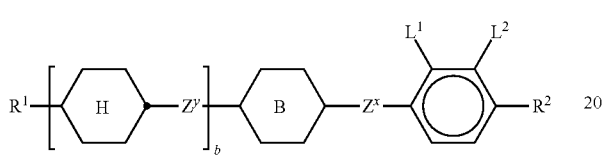

PY wherein
a denotes 1 or 2,
b denotes 0 or 1

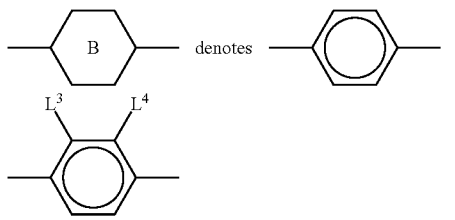

$R^1$ and $R^2$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms, $Z^x$ and $Z^y$ each, independently of one another, denote —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond, preferably a single bond, $L^{1-4}$ each, independently of one another, denote F, Cl, $OCF_3$, $CF_3$, $CH_3$, $CH_2F$, $CHF_2$.

Preferably, both $L^1$ and $L^2$ denote F or one of $L^1$ and $L^2$ denotes F and the other denotes Cl, or both $L^3$ and $L^4$ denote F or one of $L^3$ and $L^4$ denotes F and the other denotes Cl.

The compounds of the formula CY are preferably selected from the group consisting of the following sub-formulae:

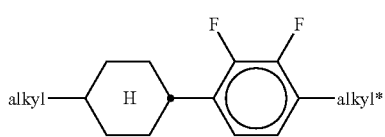

CY1

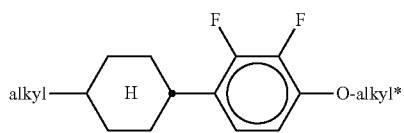

CY2

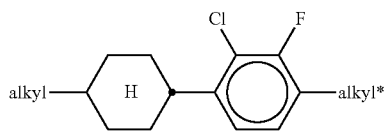

CY3

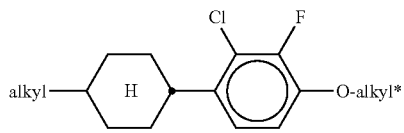

CY4

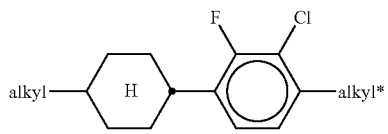

CY5

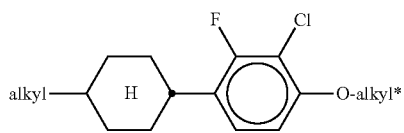

CY6

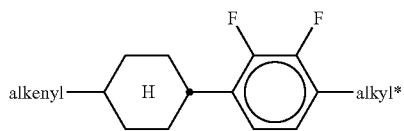

CY7

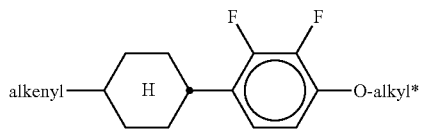

CY8

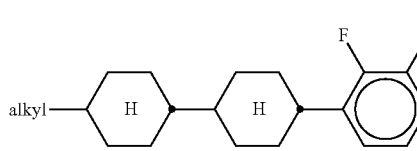

CY9

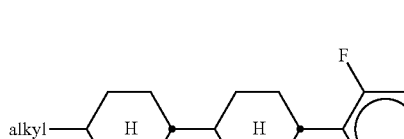

CY10

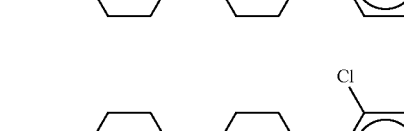

CY11

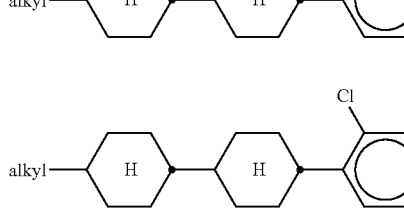

CY12

-continued
CY13
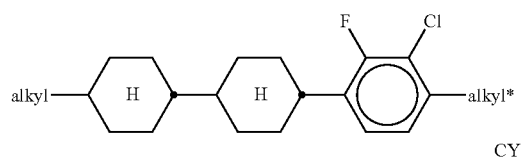
CY14
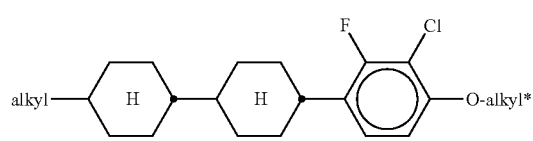
CY15
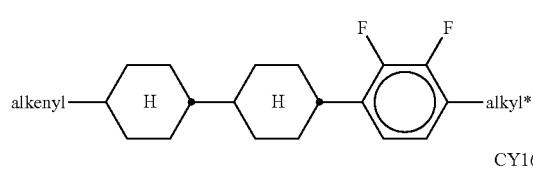
CY16
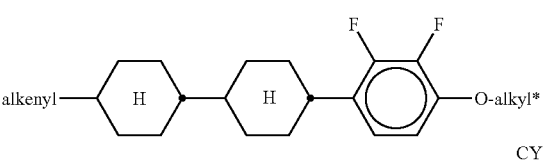
CY17
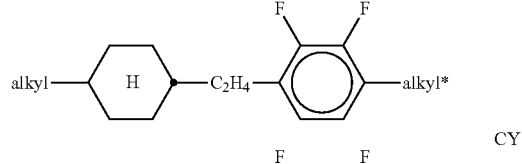
CY18
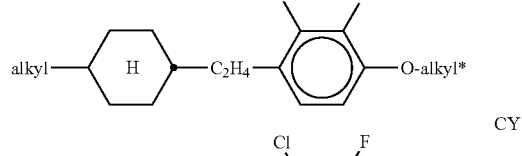
CY19
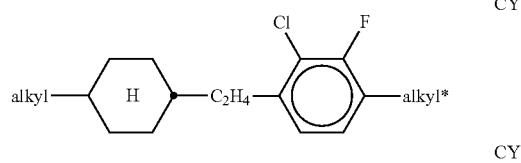
CY20
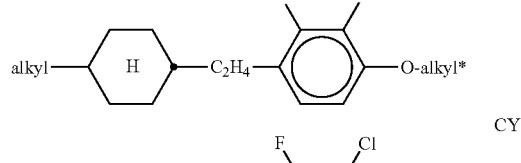
CY21
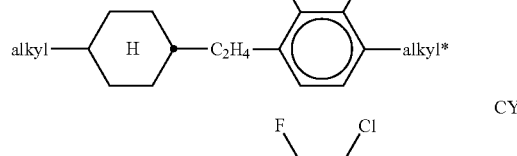
CY22
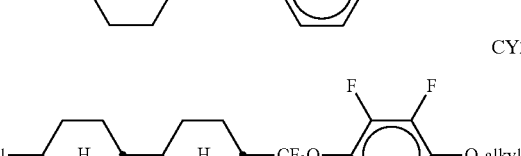
CY23
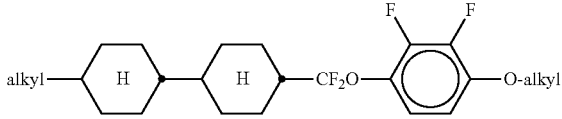
-continued
CY24
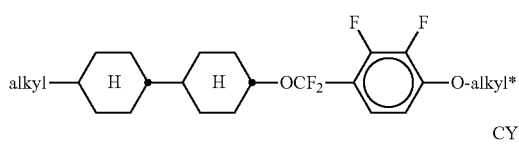
CY25
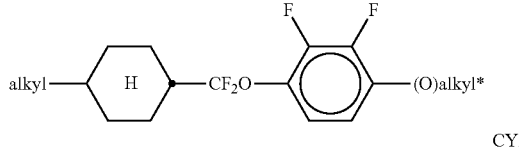
CY26
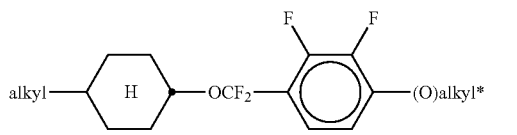
CY27
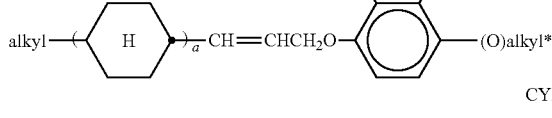
CY28
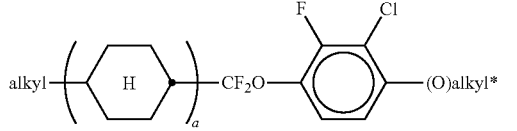
CY29
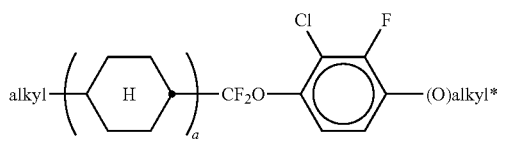
CY30
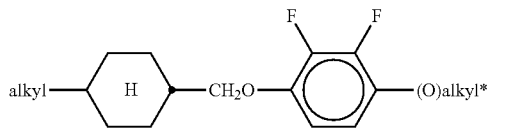
CY31
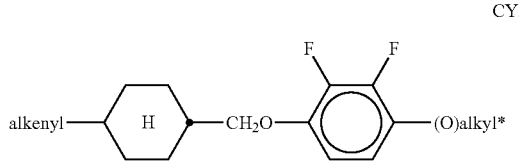
CY32
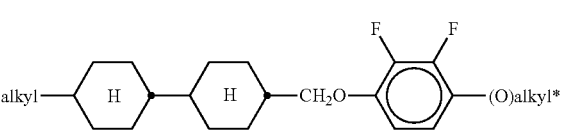
CY33
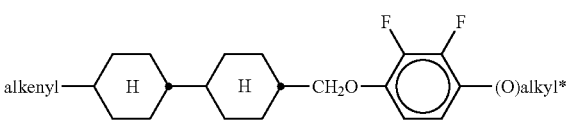
wherein a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

The compounds of the formula PY are preferably selected from the group consisting of the following sub-formulae:

PY1
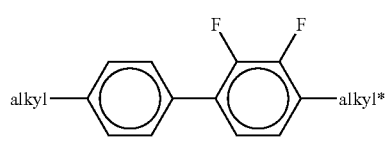

PY2
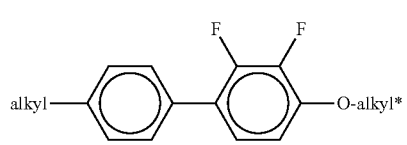

PY3
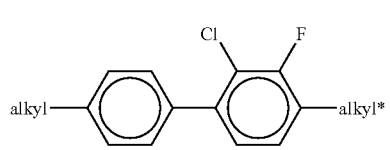

PY4
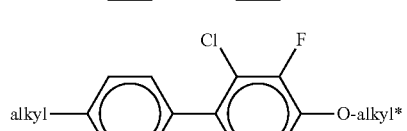

PY5
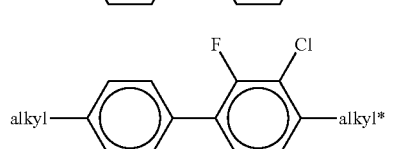

PY6

PY7
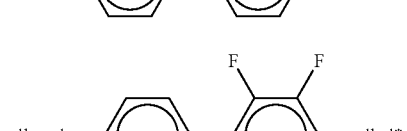

PY8
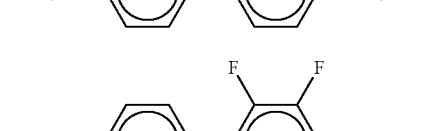

PY9

-continued

PY10
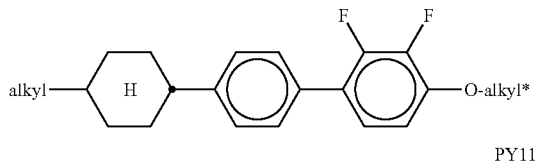

PY11
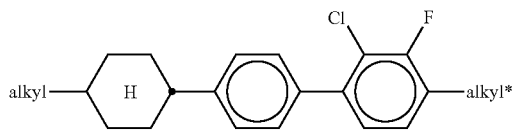

PY12
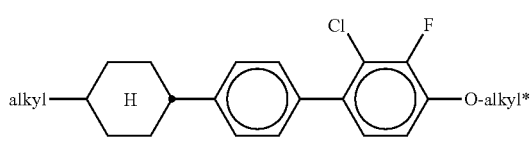

PY13
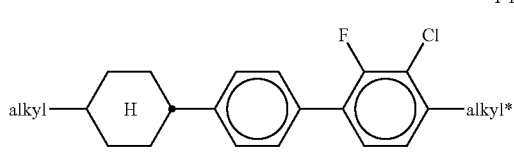

PY14
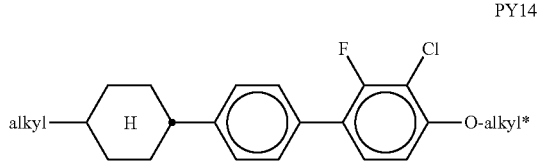

PY15
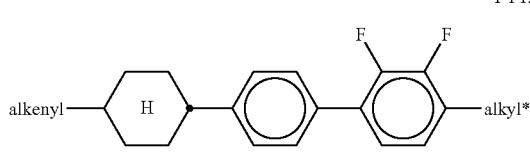

PY16
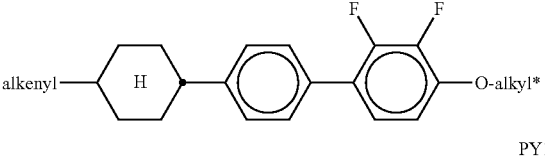

PY17
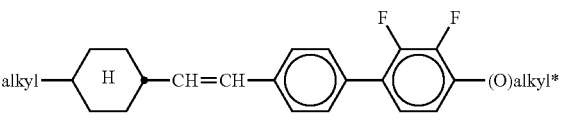

PY18
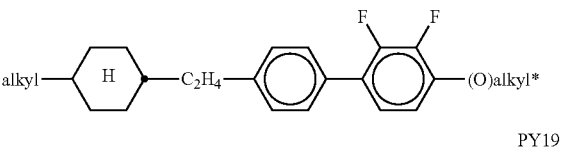

PY19
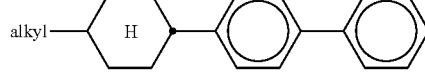

PY20

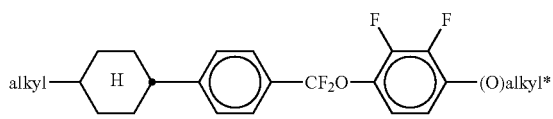

wherein alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

b) LC medium which additionally comprises one or more compounds of the following formula:

ZK

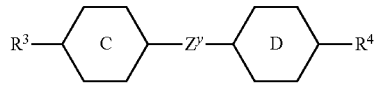

in which the individual radicals have the following meanings:

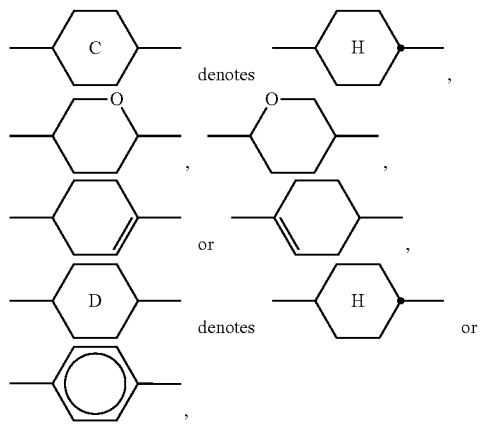

R$^3$ and R$^4$ each, independently of one another, denote alkyl having 1 to 12 C atoms, in which, in addition, one or two non-adjacent CH$_2$ groups may be replaced by —O—, —CH=CH—, —CO—, —O—CO— or —CO—O— in such a way that O atoms are not linked directly to one another, Z$^y$ denotes —CH$_2$CH$_2$—, —CH=CH—, —CF$_2$O—, —OCF$_2$—, —CH$_2$O—, —OCH$_2$—, —CO—O—, —O—CO—, —C$_2$F4-, —CF=CF—, —CH=CH—CH$_2$O— or a single bond, preferably a single bond.

The compounds of the formula ZK are preferably selected from the group consisting of the following sub-formulae:

ZK1

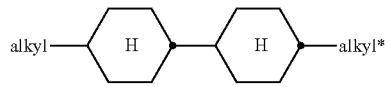

ZK2

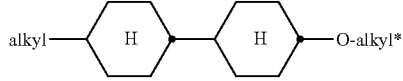

ZK3

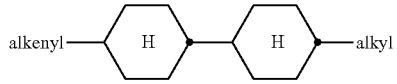

ZK4

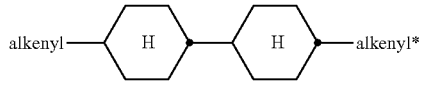

ZK5

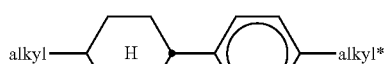

ZK6

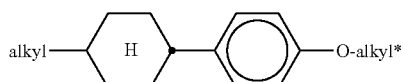

ZK7

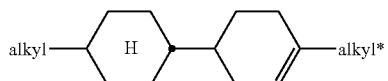

ZK8

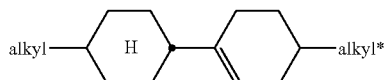

ZK9

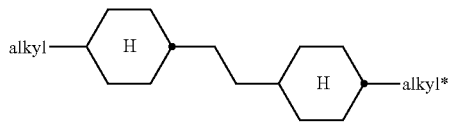

ZK10

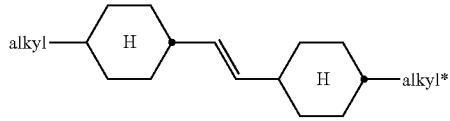

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Especially preferred are compounds of formula ZK1 and ZK3.

Particularly preferred compounds of formula ZK are selected from the following sub-formulae:

ZK1a

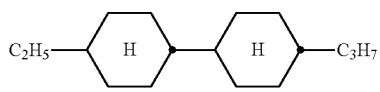

ZK1b

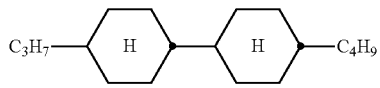

-continued

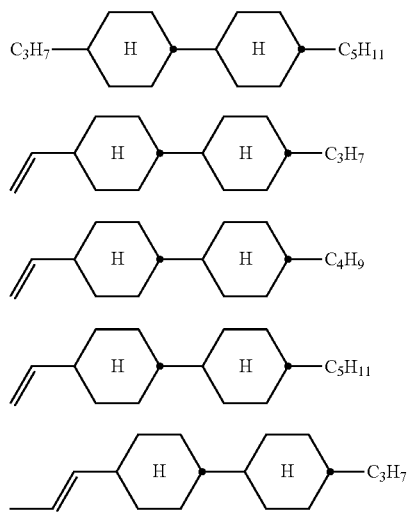

ZK1c, ZK3a, ZK3b, ZK3c, ZK3d wherein the propyl, butyl and pentyl groups are straight-chain groups.

Most preferred are compounds of formula ZK1a and ZK3a.

c) LC medium which additionally comprises one or more compounds of the following formula:

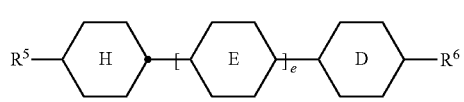

DK in which the individual radicals on each occurrence, identically or differently, have the following meanings:

$R^5$ and $R^6$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms,

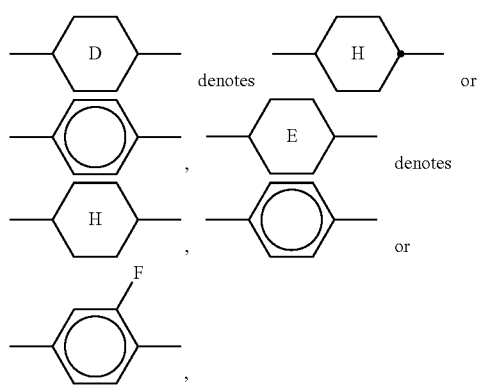

e denotes 1 or 2.

The compounds of the formula DK are preferably selected from the group consisting of the following sub-formulae:

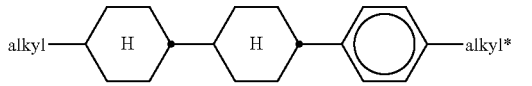
DK1

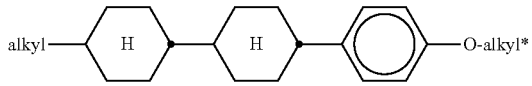
DK2

DK3

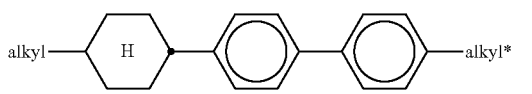
DK4

DK5

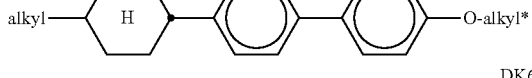
DK6

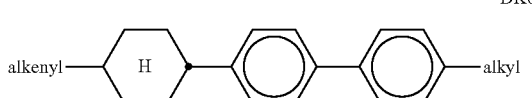
DK7

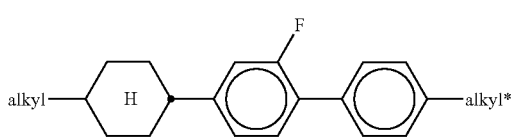
DK8

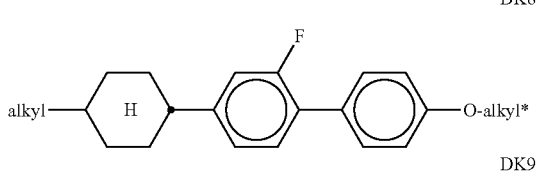
DK9

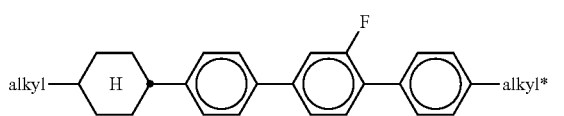
DK10

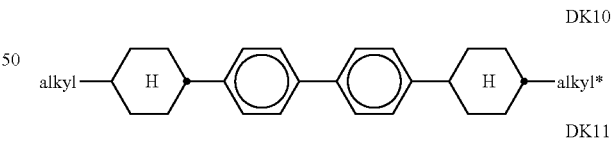
DK11

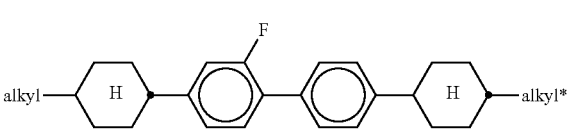
DK12

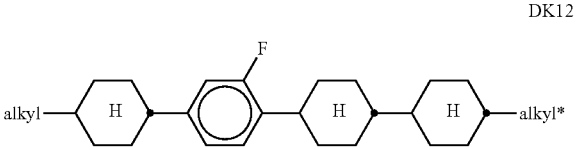

in which alkyl and alkyl* each, independently of one another, denote a straight-chain alkyl radical having 1-6

C atoms, and alkenyl denotes a straight-chain alkenyl radical having 2-6 C atoms. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

d) LC medium which additionally comprises one or more compounds of the following formula:

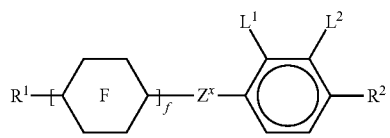

LY in which the individual radicals have the following meanings:

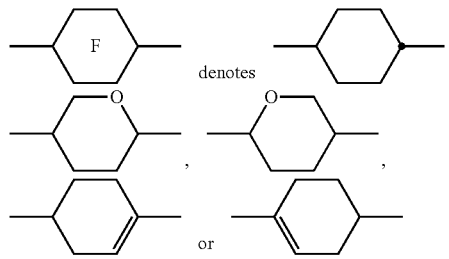

denotes with at least one ring F being different from cyclohexylene, f denotes 1 or 2, $R^1$ and $R^2$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, $Z^x$ denotes —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond, preferably a single bond, $L^1$ and $L^2$ each, independently of one another, denote F, Cl, $OCF_3$, $CF_3$, $CH_3$, $CH_2F$, $CHF_2$.

Preferably, both radicals $L^1$ and $L^2$ denote F or one of the radicals $L^1$ and $L^2$ denotes F and the other denotes Cl. The compounds of the formula LY are preferably selected from the group consisting of the following sub-formulae:

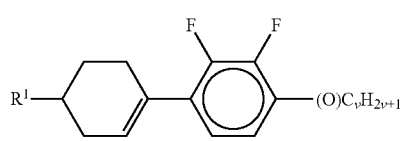

LY1

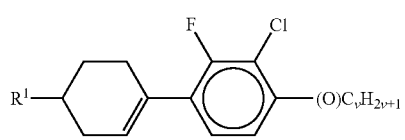

LY2

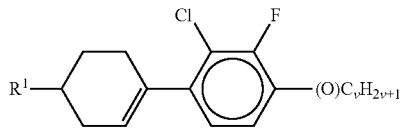

LY3

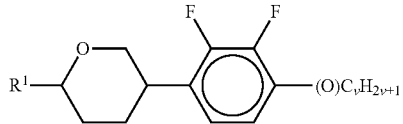

LY4

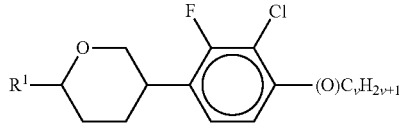

LY5

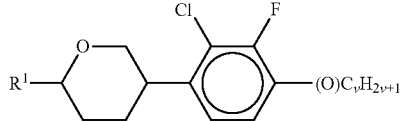

LY6

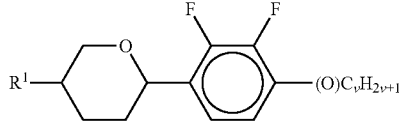

LY7

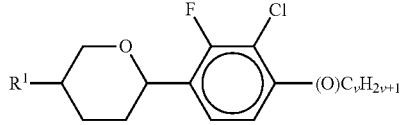

LY8

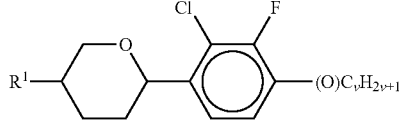

LY9

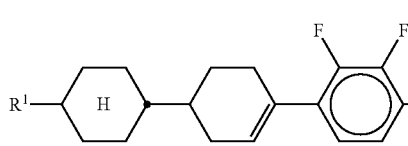

LY10

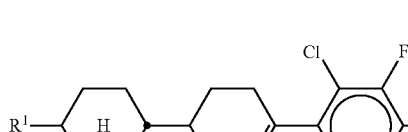

LY11

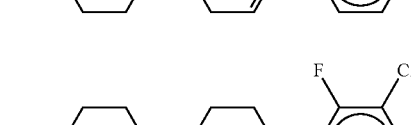

LY12

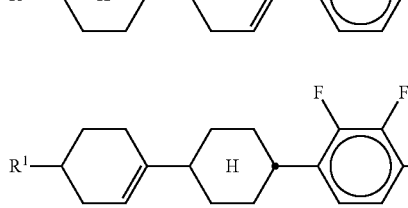

LY13

LY14
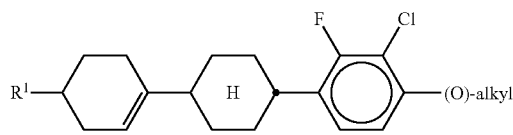

LY15
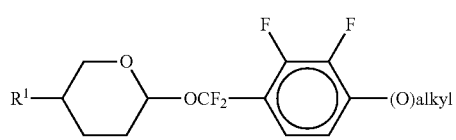

LY16
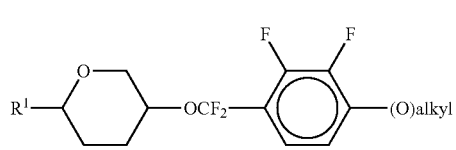

LY17
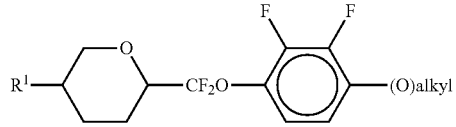

LY18
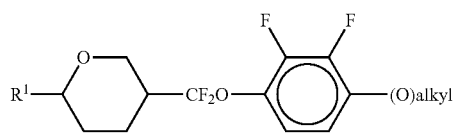

LY19
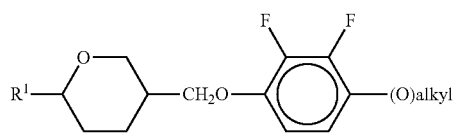

LY20
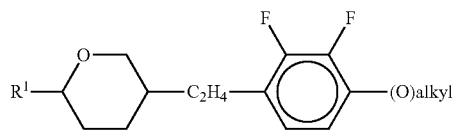

LY21
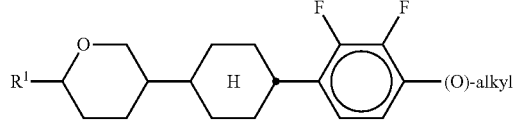

LY22
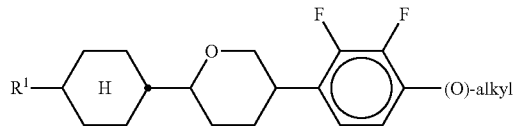

LY23
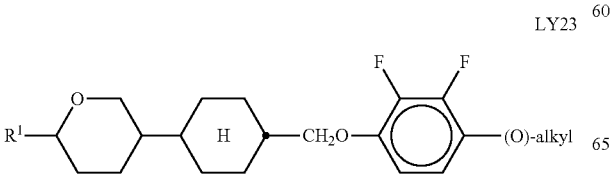

LY24
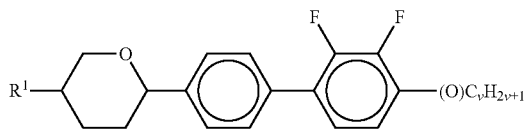

in which $R^1$ has the meaning indicated above, alkyl denotes a straight-chain alkyl radical having 1-6 C atoms, (O) denotes an oxygen atom or a single bond, and v denotes an integer from 1 to 6. $R^1$ preferably denotes straight-chain alkyl having 1 to 6 C atoms or straight-chain alkenyl having 2 to 6 C atoms, in particular $CH_3$, $C_2H_5$, n-$C_3H_7$, n-$C_4H_9$, n-$C_5H_{11}$, $CH_2\!\!=\!\!CH\!-\!$, $CH_2\!\!=\!\!CHCH_2CH_2\!-\!$, $CH_3\!-\!CH\!\!=\!\!CH\!-\!$, $CH_3\!-\!CH_2\!-\!CH\!\!=\!\!CH\!-\!$, $CH_3\!-\!(CH_2)_2\!-\!CH\!\!=\!\!CH\!-\!$, $CH_3\!-\!(CH_2)_3\!-\!CH\!\!=\!\!CH\!-\!$ or $CH_3\!-\!CH\!\!=\!\!CH\!-\!(CH_2)_2\!-\!$.

e) LC medium which additionally comprises one or more compounds selected from the group consisting of the following formulae:

G1
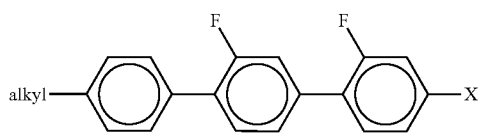

G2
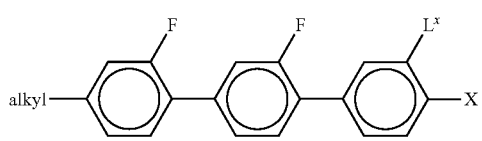

G3
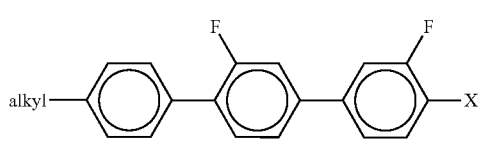

G4
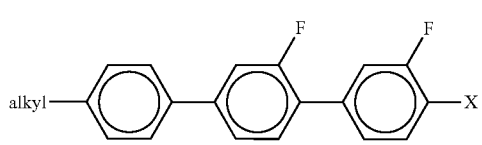

in which alkyl denotes $C_{1-6}$-alkyl, $L^x$ denotes H or F, and X denotes F, Cl, $OCF_3$, $OCHF_2$ or $OCH\!\!=\!\!CF_2$. Particular preference is given to compounds of the formula G1 in which X denotes F.

f) LC medium which additionally comprises one or more compounds selected from the group consisting of the following formulae:

Y1
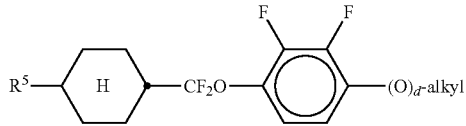

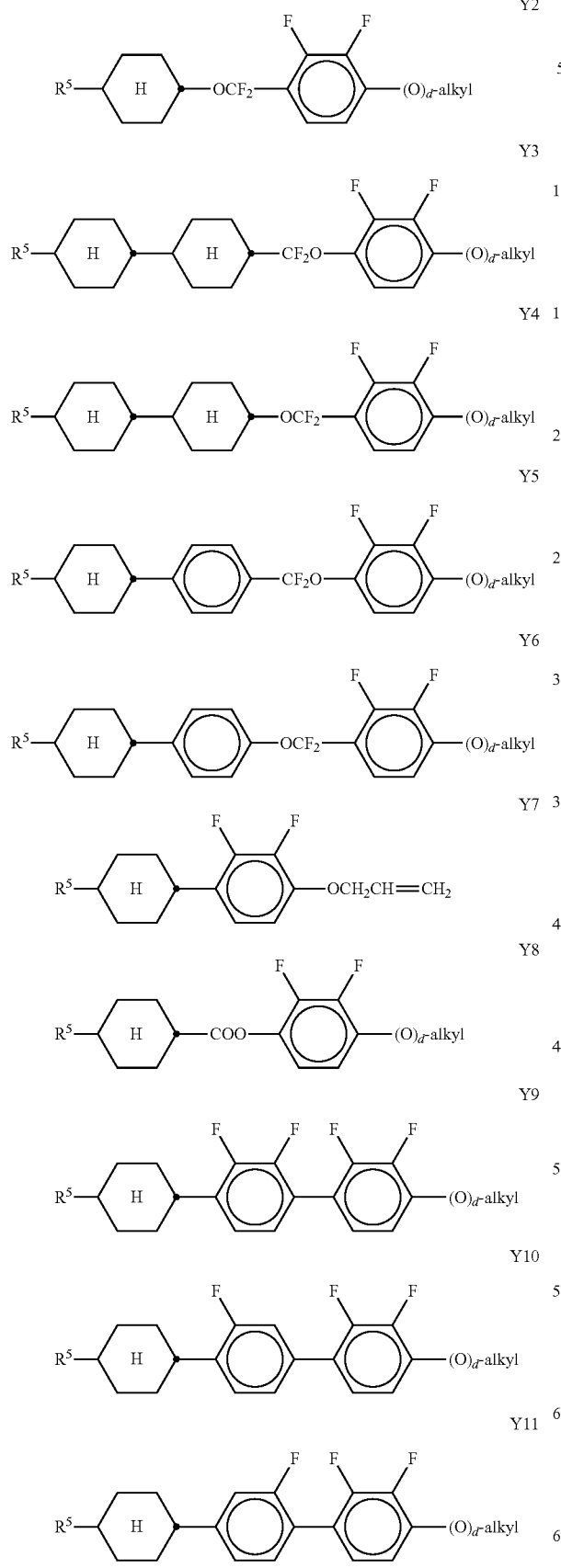

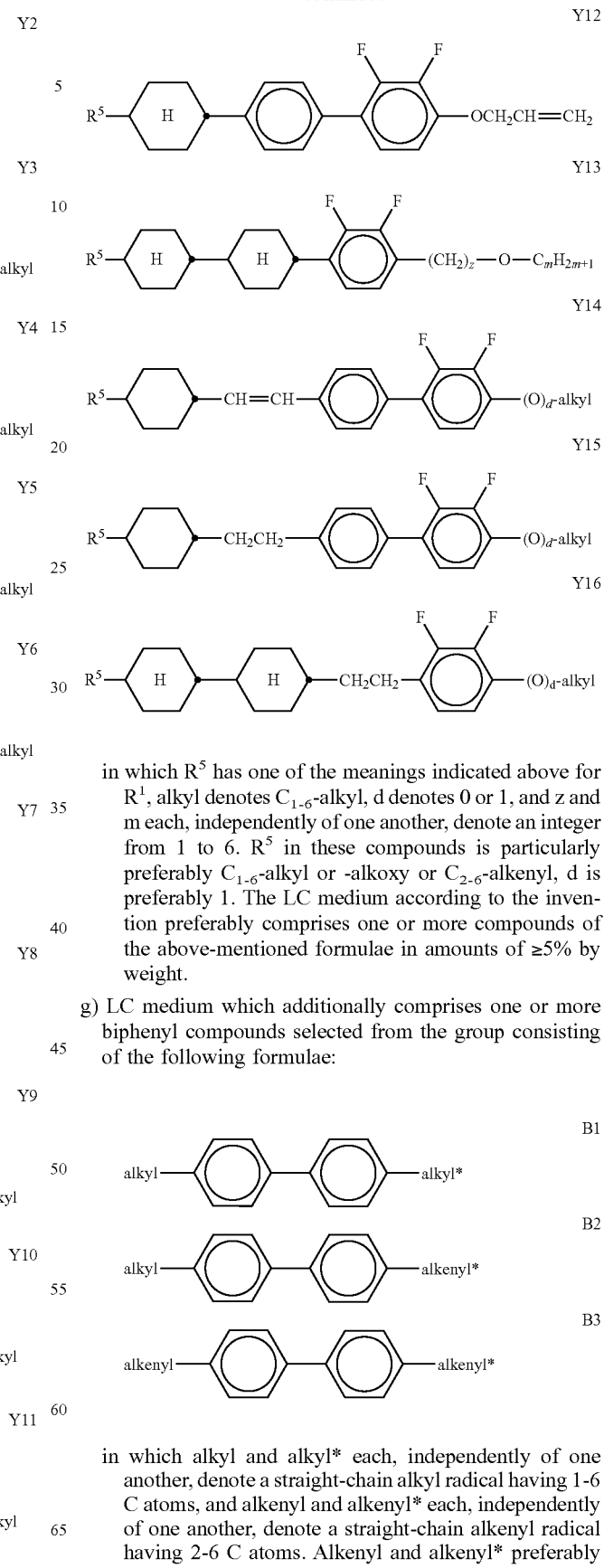

in which $R^5$ has one of the meanings indicated above for $R^1$, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of ≥5% by weight.

g) LC medium which additionally comprises one or more biphenyl compounds selected from the group consisting of the following formulae:

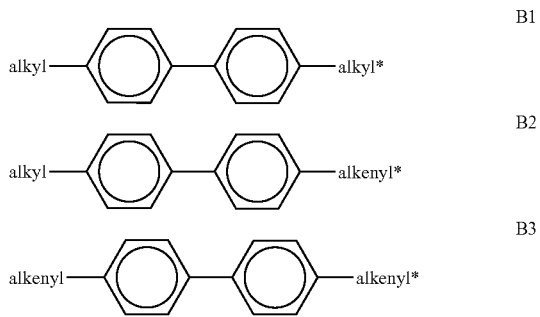

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2$=CH—, $CH_2$=CHCH$_2$CH$_2$—, $CH_3$—

CH=CH—, CH₃—CH₂—CH=CH—, CH₃—(CH₂)₂—CH=CH—, CH₃—(CH₂)₃—CH=CH— or CH₃—CH=CH—(CH₂)₂—.

The proportion of the biphenyls of the formulae B1 to B3 in the LC mixture is preferably at least 3% by weight, in particular ≥5% by weight.

The compounds of the formula B2 are particularly preferred.

The compounds of the formulae B1 to B3 are preferably selected from the group consisting of the following sub-formulae:

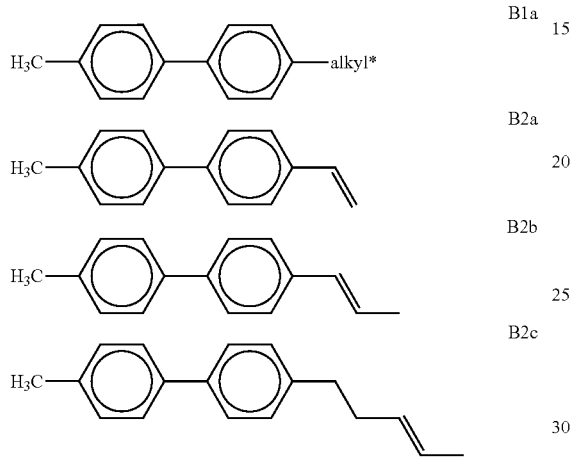

in which alkyl* denotes an alkyl radical having 1-6 C atoms. The medium according to the invention particularly preferably comprises one or more compounds of the formulae B1a and/or B2c.

h) LC medium which additionally comprises one or more terphenyl compounds of the following formula:

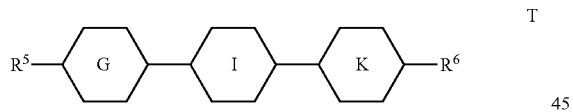

in which $R^5$ and $R^6$ each, independently of one another, have one of the meanings indicated above, and

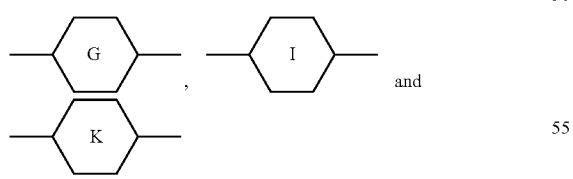

each, independently of one another, denote

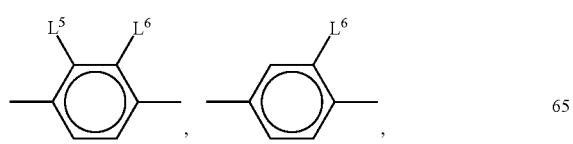

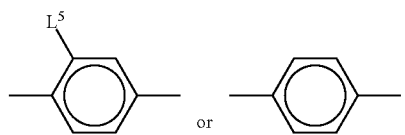

in which $L^5$ denotes F or Cl, preferably F, and $L^6$ denotes F, Cl, OCF₃, CF₃, CH₃, CH₂F or CHF₂, preferably F.

The compounds of the formula T are preferably selected from the group consisting of the following sub-formulae:

T1

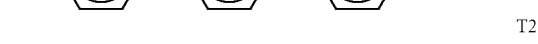

T2

T3

T4

T5

T6

T7

T8

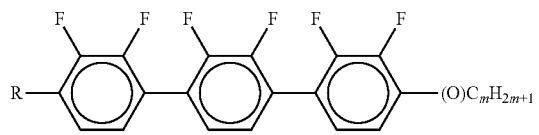
T9

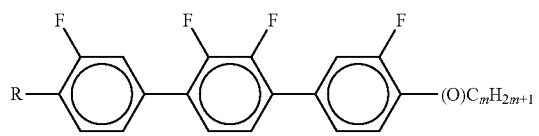
T10

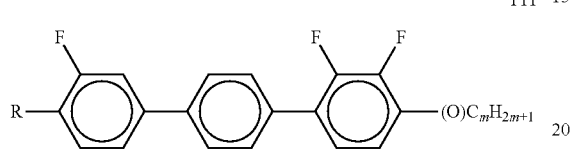
T11

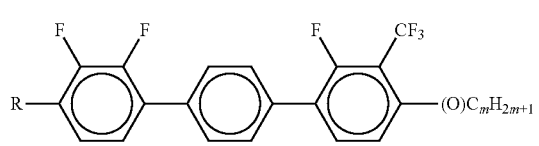
T12

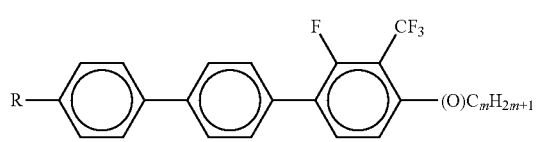
T13

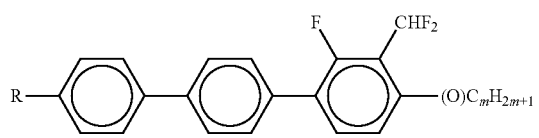
T14

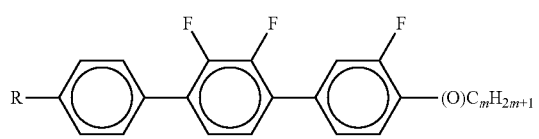
T15

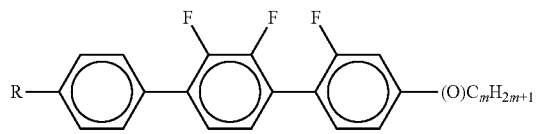
T16

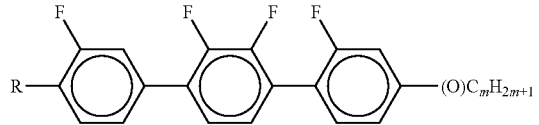
T17

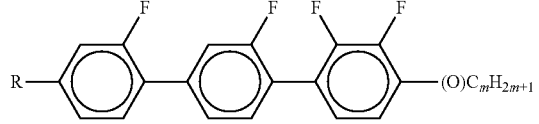
T18

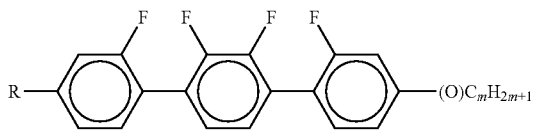
T19

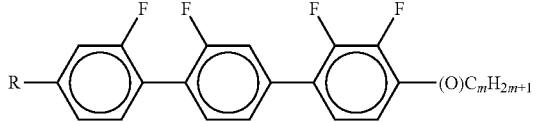
T20

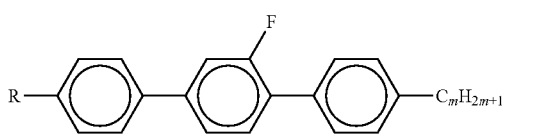
T21

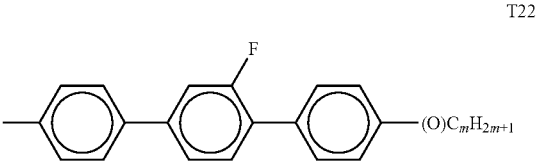
T22

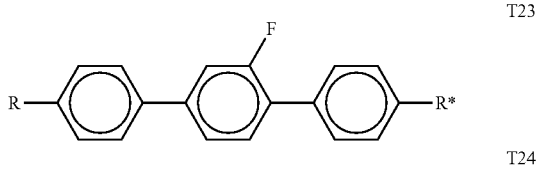
T23

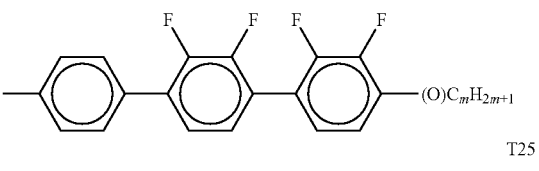
T24

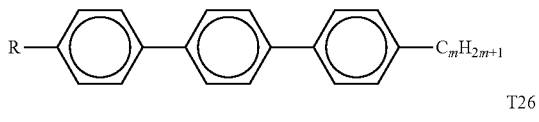
T25

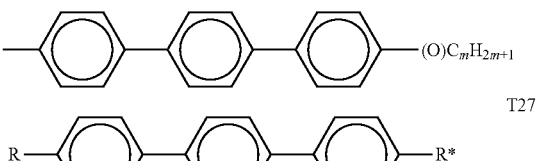
T26

T27 in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

R preferably denotes methyl, ethyl, propyl, butyl, pentyl, hexyl, methoxy, ethoxy, propoxy, butoxy or pentoxy.

The LC medium according to the invention preferably comprises the terphenyls of the formula T and the preferred sub-formulae thereof in an amount of 0.5-30% by weight, in particular 1-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in mixtures according to the invention if the Δn value of the mixture is to be ≥0.1. Preferred mixtures comprise 2-20% by weight of one or more terphenyl compounds of the formula T, preferably selected from the group of compounds T1 to T22.

i) LC medium which additionally comprises one or more compounds selected from the group consisting of the following formulae:

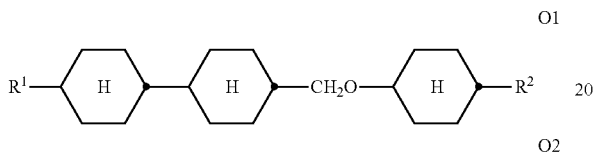

O1

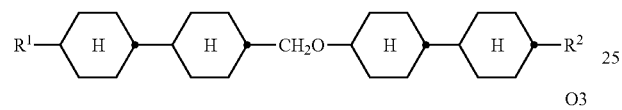

O2

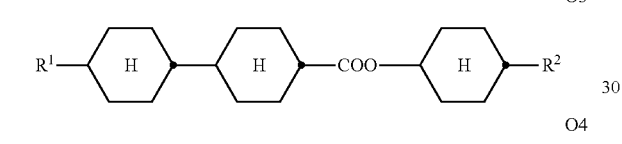

O3

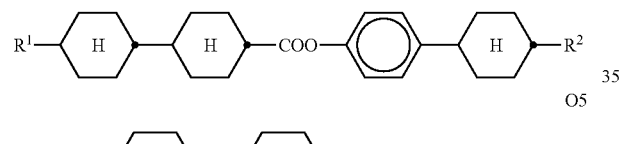

O4

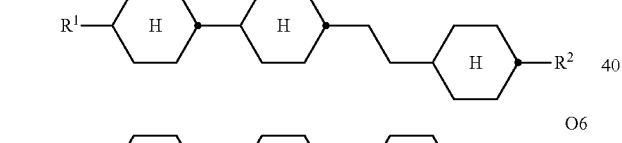

O5

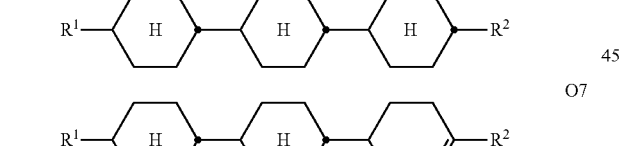

O6

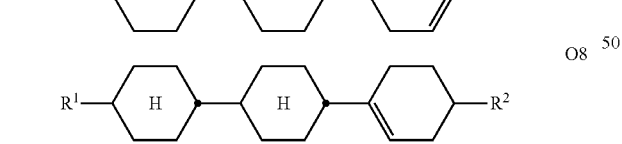

O7

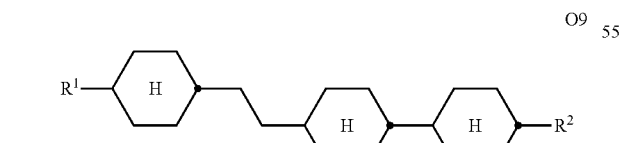

O8

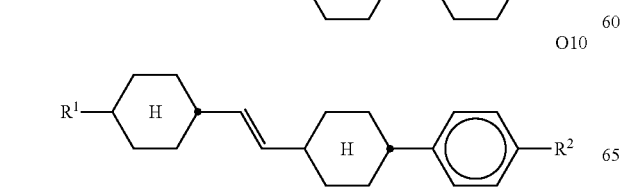

O9

O10

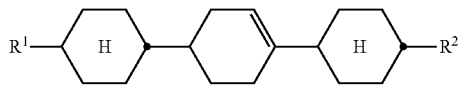

O11 in which $R^1$ and $R^2$ have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O1, O3 and O4.

k) LC medium which additionally comprises one or more compounds of the following formula:

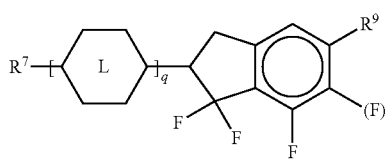

FI in which

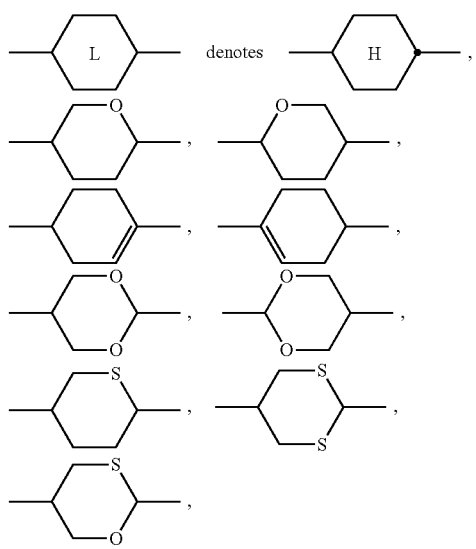

$R^9$ denotes H, $CH_3$, $C_2H_5$ or n-$C_3H_7$, (F) denotes an optional fluorine substituent, and q denotes 1, 2 or 3, and $R^7$ has one of the meanings indicated for $R^1$, preferably in amounts of >3% by weight, in particular ≥5% by weight and very particularly preferably 5-30% by weight.

Particularly preferred compounds of the formula FI are selected from the group consisting of the following sub-formulae:

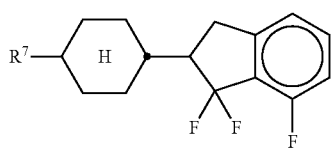

FI1

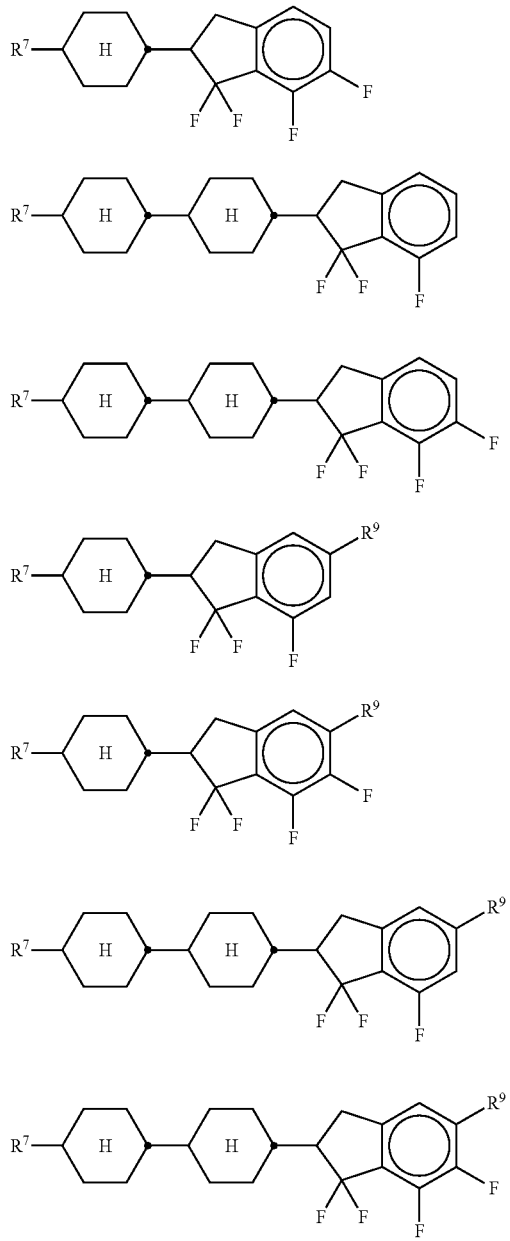

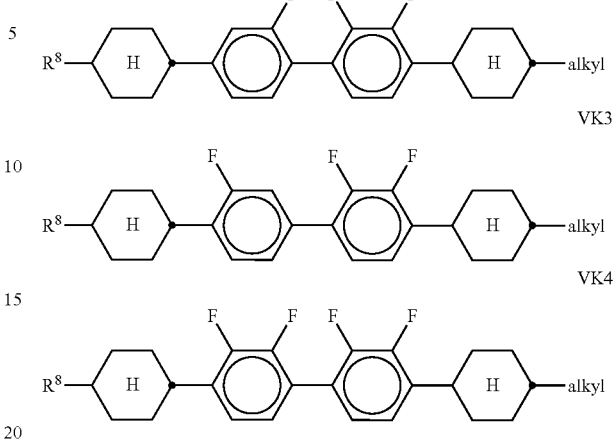

in which $R^7$ preferably denotes straight-chain alkyl, and $R^9$ denotes $CH_3$, $C_2H_5$ or n-$C_3H_7$. Particular preference is given to the compounds of the formulae FI1, FI2 and FI3.

l) LC medium which additionally comprises one or more compounds selected from the group consisting of the following formulae:

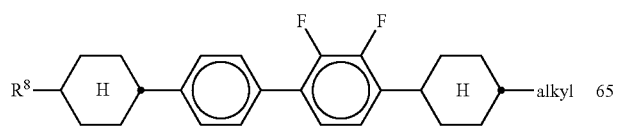

in which $R^8$ has the meaning indicated for $R^1$, and alkyl denotes a straight-chain alkyl radical having 1-6 C atoms.

m) LC medium which additionally comprises one or more compounds which contain a tetrahydronaphthyl or naphthyl unit, such as, for example, the compounds selected from the group consisting of the following formulae:

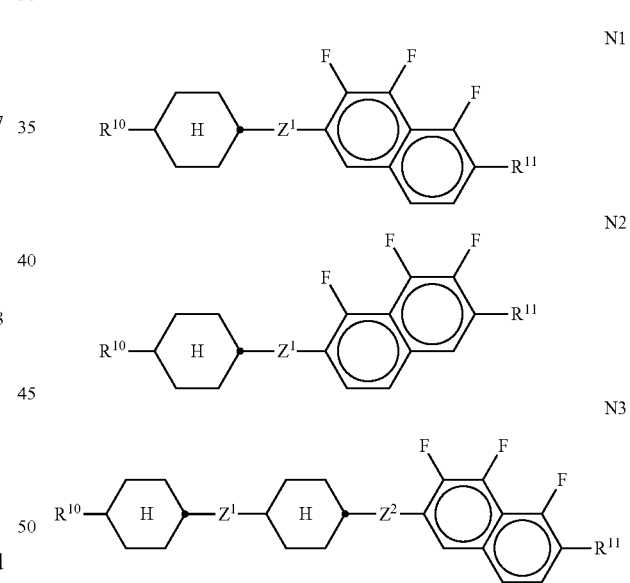

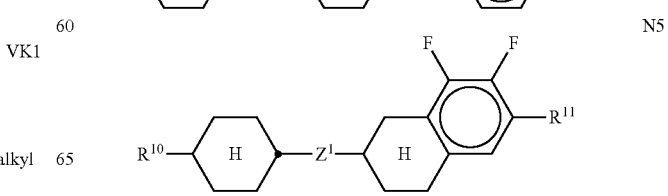

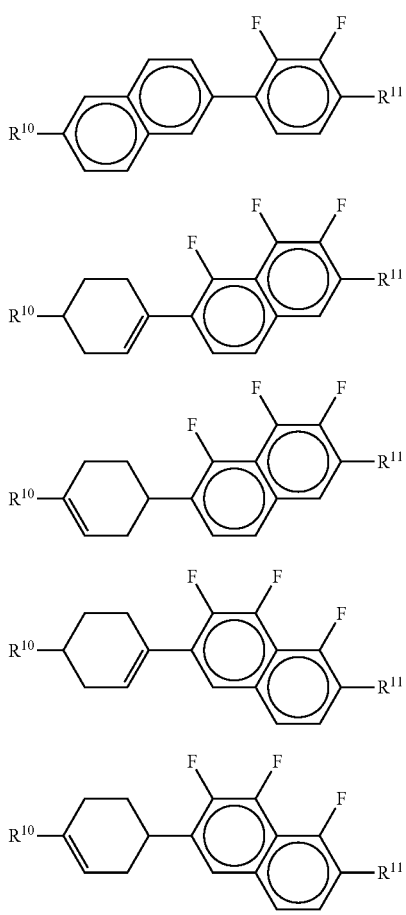

in which
R$^{10}$ and R$^{11}$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms,
and R$^{10}$ and R$^{11}$ preferably denote straight-chain alkyl or alkoxy having 1 to 6 C atoms or straight-chain alkenyl having 2 to 6 C atoms, and
Z$^1$ and Z$^2$ each, independently of one another, denote —C$_2$H$_4$—, —CH=CH—, —(CH$_2$)$_4$—, —(CH$_2$)$_3$O—, —O(CH$_2$)$_3$—, —CH=CH—CH$_2$CH$_2$—, —CH$_2$CH$_2$CH=CH—, —CH$_2$O—, —OCH$_2$—, —CO—O—, —O—CO—, —C$_2$F$_4$—, —CF=CF—, —CF=CH—, —CH=CF—, —CH$_2$— or a single bond.

n) LC medium which additionally comprises one or more difluorodibenzo-chromans and/or chromates of the following formulae:

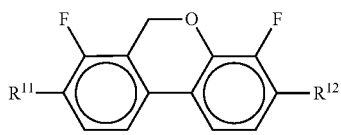

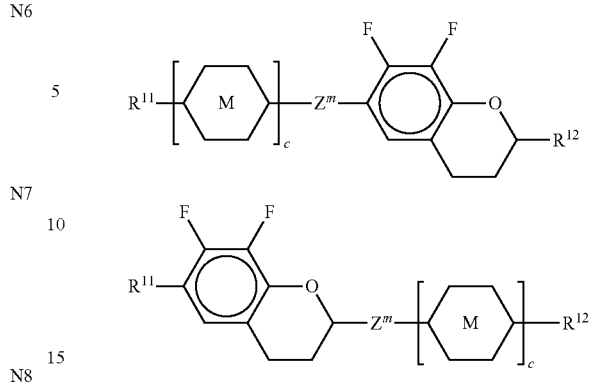

in which
R$^{11}$ and R$^{12}$ each, independently of one another, have one of the meanings indicated above for R$^{11}$,
ring M is trans-1,4-cyclohexylene or 1,4-phenylene,
Z$^m$ —C$_2$H$_4$—, —CH$_2$O—, —OCH$_2$—, —CO—O— or —O—CO—,
c is 0, 1 or 2,
preferably in amounts of 3 to 20% by weight, in particular in amounts of 3 to 15% by weight.

Particularly preferred compounds of the formulae BC, CR and RC are selected from the group consisting of the following sub-formulae:

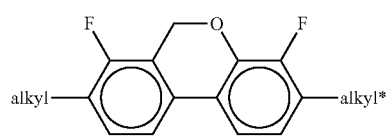

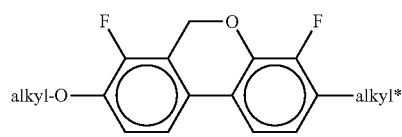

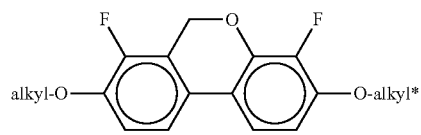

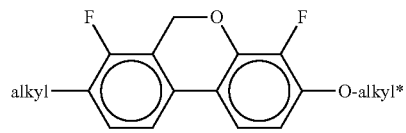

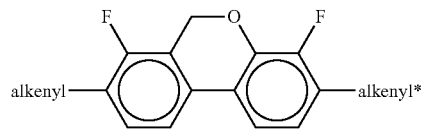

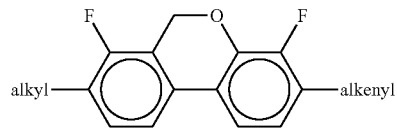

BC7

<img structure: alkenyl—[benzene with F, O bridge]—[benzene with F]—alkyl>

CR1

<img: alkyl—[H cyclohexane]—O—[difluorobenzene fused chroman]—alkyl*>

CR2

<img: alkyl-O—[H cyclohexane]—CH2—[difluorobenzene fused chroman]—alkyl*>

CR3

<img: Alkyl(O)—[H cyclohexane]—CH2CH2—[difluorobenzene fused chroman]—Alkyl*>

CR4

<img: Alkyl(O)—[H cyclohexane]—COO—[difluorobenzene fused chroman]—Alkyl*>

CR5

<img: Alkyl—[H]—[H]—O—[difluorobenzene fused chroman]—Alkyl*>

CR6

<img: Alkyl-O—[H]—[H]—CH2—[difluorobenzene fused chroman]—Alkyl*>

CR7

<img: Alkenyl—[H]—[H]—CH2—[difluorobenzene fused chroman]—Alkyl*>

CR8

<img: Alkyl(O)—[H]—[H]—CH2CH2—[difluorobenzene fused chroman]—Alkyl*>

CR9

<img: Alkyl(O)—[H]—[H]—COO—[difluorobenzene fused chroman]—Alkyl*>

RC1

<img: Alkyl(O)—[difluorobenzene fused chroman]—CH2—O—[H cyclohexane]c—Alkyl>

RC2

<img: Alkyl(O)—[difluorobenzene fused chroman]—CH2CH2—[H cyclohexane]c—Alkyl>

RC3

<img: Alkyl(O)—[difluorobenzene fused chroman]—COO—[H cyclohexane]c—Alkyl> in which alkyl and alkyl* each, independently of one another, denote a straight-chain alkyl radical having 1-6 C atoms, (O) denotes an oxygen atom or a single bond, c is 1 or 2, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Very particular preference is given to mixtures comprising one, two or three compounds of the formula BC-2.

o) LC medium which additionally comprises one or more fluorinated phenanthrenes and/or dibenzofurans of the following formulae:

PH

<img: phenanthrene with $R^{11}$, $R^{12}$, $(L)_r$ substituents>

BF

<img: dibenzofuran structure with $R^{11}$—[ring]$_b$—[dibenzofuran]—$R^{12}$, $(L)_r$> in which $R^{11}$ and $R^{12}$ each, independently of one another, have one of the meanings indicated above for $R^{11}$, b denotes 0 or 1, L denotes F, and r denotes 1, 2 or 3.

Particularly preferred compounds of the formulae PH and BF are selected from the group consisting of the following sub-formulae:

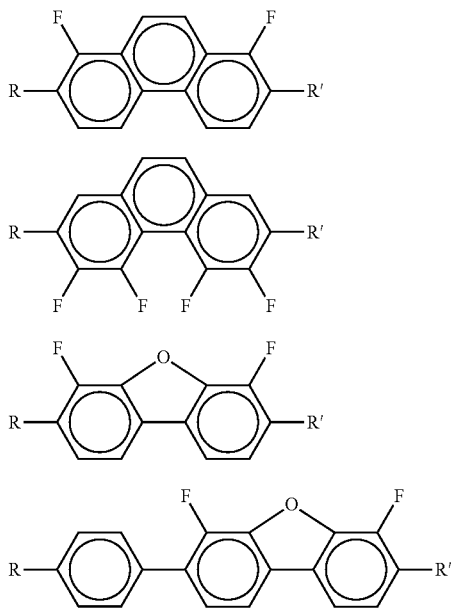

in which R and R' each, independently of one another, denote a straight-chain alkyl or alkoxy radical having 1-7 C atoms.

p) LC medium which additionally comprises one or more monocyclic compounds of the following formula

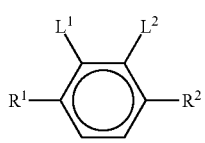

wherein
R¹ and R² each, independently of one another, denote alkyl having 1 to 12 C atoms, where, in addition, one or two non-adjacent CH₂ groups may be replaced by —O—, —CH=CH—, —CO—, —OCO— or —COO— in such a way that O atoms are not linked directly to one another, preferably alkyl or alkoxy having 1 to 6 C atoms,
L¹ and L² each, independently of one another, denote F, Cl, OCF₃, CF₃, CH₃, CH₂F, CHF₂.
Preferably, both L¹ and L² denote F or one of L¹ and L² denotes F and the other denotes Cl,
The compounds of the formula Y are preferably selected from the group consisting of the following sub-formulae:

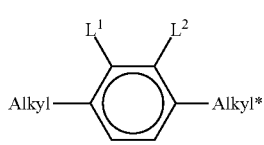

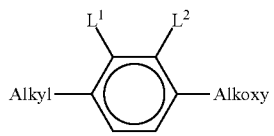

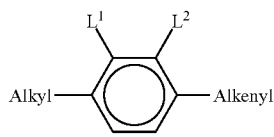

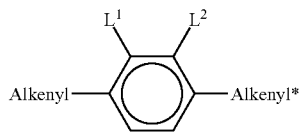

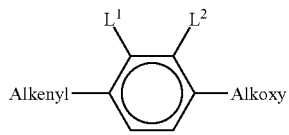

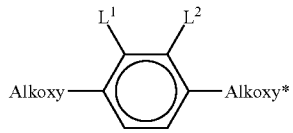

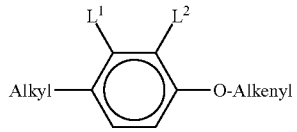

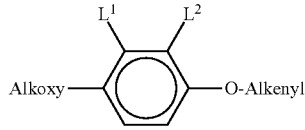

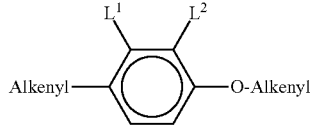

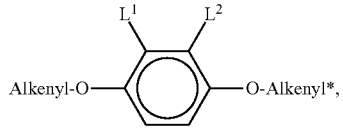

in which, Alkyl and Alkyl* each, independently of one another, denote a straight-chain alkyl radical having 1-6 C atoms, Alkoxy denotes a straight-chain alkoxy radical having 1-6 C atoms, Alkenyl and Alkenyl* each, independently of one another, denote a straight-chain alkenyl radical having 2-6 C atoms, and O denotes an oxygen atom or a single bond. Alkenyl and Alkenyl* preferably denote CH₂=CH—, CH₂=CHCH₂CH₂—, CH₃—CH=CH—, CH₃—CH₂—CH=CH—, CH₃—(CH₂)₂—CH=CH—, CH₃—(CH₂)₃—CH=CH— or CH₃—CH=CH—(CH₂)₂—.
Particularly preferred compounds of the formula Y are selected from the group consisting of the following sub-formulae:

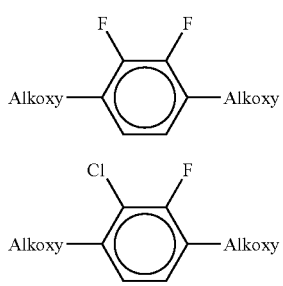

wherein Alkoxy preferably denotes straight-chain alkoxy with 3, 4, or 5 C atoms.

q) LC medium which, apart from the stabilisers according to the invention, in particular of the formula I or sub-formulae thereof and the comonomers, comprises no compounds which contain a terminal vinyloxy group (—O—CH=CH$_2$).

r) LC medium which comprises 1 to 5, preferably 1, 2 or 3, stabilisers, preferably selected from stabilisers according to the invention, in particular of the formula I or sub-formulae thereof.

s) LC medium in which the proportion of stabilisers, in particular of the formula I or sub-formulae thereof, in the mixture as a whole is 1 to 1500 ppm, preferably 100 to 1000 ppm.

t) LC medium which comprises 1 to 8, preferably 1 to 5, compounds of the formulae CY1, CY2, PY1 and/or PY2. The proportion of these compounds in the mixture as a whole is preferably 5 to 60%, particularly preferably 10 to 35%. The content of these individual compounds is preferably in each case 2 to 20%.

u) LC medium which comprises 1 to 8, preferably 1 to 5, compounds of the formulae CY9, CY10, PY9 and/or PY10. The proportion of these compounds in the mixture as a whole is preferably 5 to 60%, particularly preferably 10 to 35%. The content of these individual compounds is preferably in each case 2 to 20%.

v) LC medium which comprises 1 to 10, preferably 1 to 8, compounds of the formula ZK, in particular compounds of the formulae ZK1, ZK2 and/or ZK6. The proportion of these compounds in the mixture as a whole is preferably 3 to 25%, particularly preferably 5 to 45%. The content of these individual compounds is preferably in each case 2 to 20%.

w) LC medium in which the proportion of compounds of the formulae CY, PY and ZK in the mixture as a whole is greater than 70%, preferably greater than 80%.

x) LC medium in which the LC host mixture contains one or more compounds containing an alkenyl group, preferably selected from the group consisting of formula CY, PY and LY, wherein one or both of R$^1$ and R$^2$ denote straight-chain alkenyl having 2-6 C atoms, formula ZK and DK, wherein one or both of R$^3$ and R$^4$ or one or both of R$^5$ and R$^6$ denote straight-chain alkenyl having 2-6 C atoms, and formula B2 and B3, very preferably selected from formulae CY15, CY16, CY24, CY32, PY15, PY16, ZK3, ZK4, DK3, DK6, B2 and B3, most preferably selected from formulae ZK3, ZK4, B2 and B3. The concentration of these compounds in the LC host mixture is preferably from 2 to 70%, very preferably from 3 to 55%.

y) LC medium which contains one or more, preferably 1 to 5, compounds selected of formula PY1-PY8, very preferably of formula PY2. The proportion of these compounds in the mixture as a whole is preferably 1 to 30%, particularly preferably 2 to 20%. The content of these individual compounds is preferably in each case 1 to 20%.

z) LC medium which contains one or more, preferably 1, 2 or 3, compounds of formula T2. The content of these compounds in the mixture as a whole is preferably 1 to 20%.

In another preferred embodiment of the present invention the LC medium contains an LC host mixture with positive dielectric anisotropy. Preferred embodiments of such an LC medium, and the corresponding LC host mixture, are those of sections aa)-mmm) below:

aa) LC-medium, characterised in that it comprises one or more compounds selected from the group of compounds of the formulae II and III

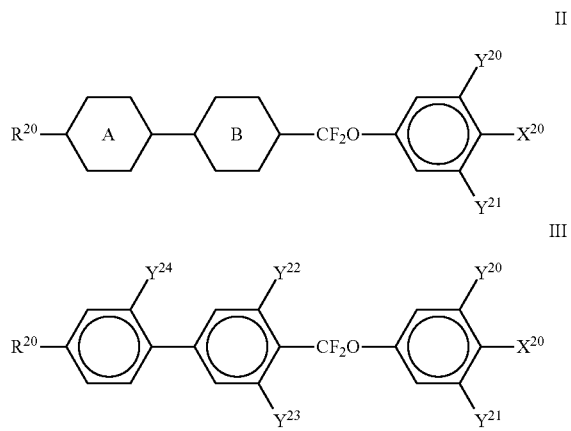

wherein

R$^{20}$ each, identically or differently, denote a halogenated or unsubstituted alkyl or alkoxy radical having 1 to 15 C atoms, where, in addition, one or more CH$_2$ groups in these radicals may each be replaced, independently of one another, by —C≡C—, —CF$_2$O—, —CH=CH—,

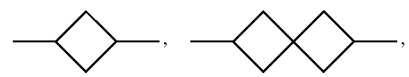

—O—, —CO—O— or —O—CO— in such a way that O atoms are not linked directly to one another, X$^{20}$ each, identically or differently, denote F, Cl, CN, SF$_5$, SCN, NCS, a halogenated alkyl radical, a halogenated alkenyl radical, a halogenated alkoxy radical or a halogenated alkenyloxy radical, each having up to 6 C atoms, and Y$^{20-24}$ each, identically or differently, denote H or F;

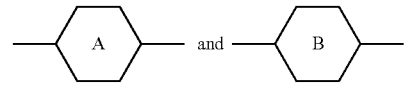

each, independently of one another, denote

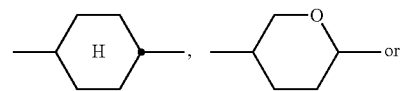

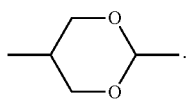

The compounds of the formula II are preferably selected from the following formulae:

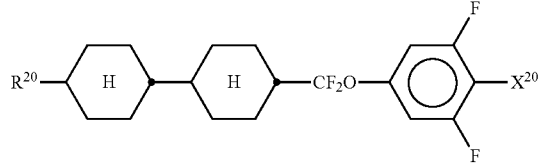
IIa

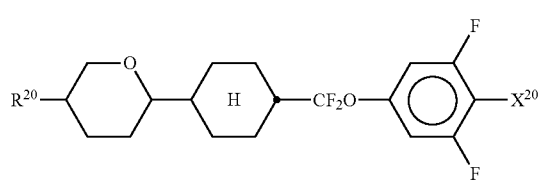
IIb

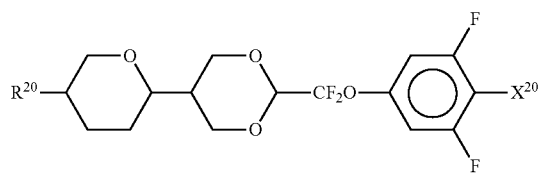
IIc

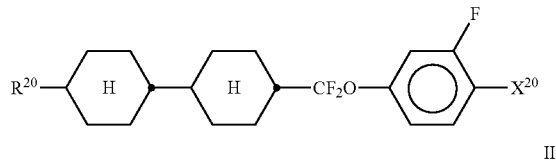
IId

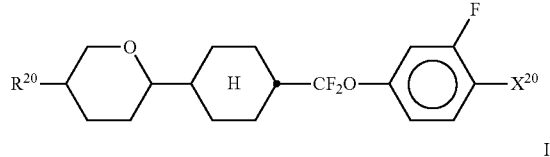
IIe

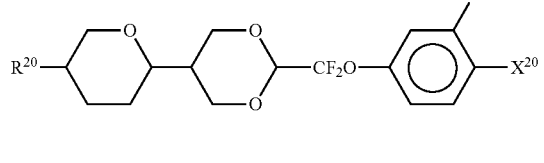
IIf wherein $R^{20}$ and $X^{20}$ have the meanings indicated above.

$R^{20}$ preferably denotes alkyl having 1 to 6 C atoms. $X^{20}$ preferably denotes F. Particular preference is given to compounds of the formulae IIa and IIb, in particular compounds of the formulae IIa and IIb wherein X denotes F.

The compounds of the formula III are preferably selected from the following formulae:

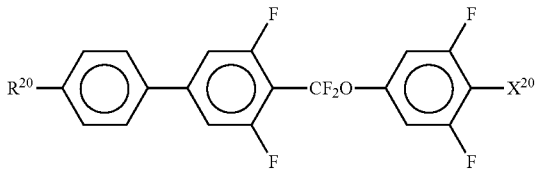
IIIa

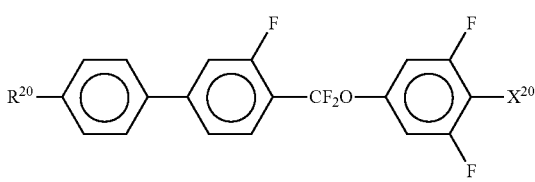
IIIb

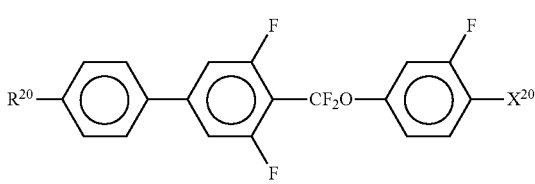
IIIc

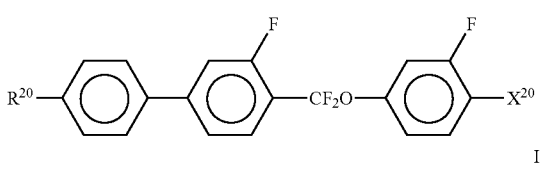
IIId

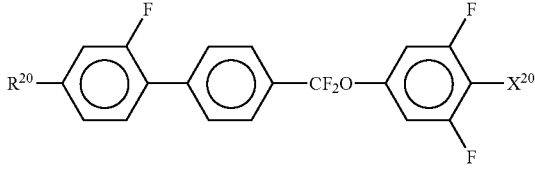
IIIe wherein $R^{20}$ and $X^{20}$ have the meanings indicated above.

$R^{20}$ preferably denotes alkyl having 1 to 6 C atoms. $X^{20}$ preferably denotes F. Particular preference is given to compounds of the formulae IIIa and IIIe, in particular compounds of the formula IIIa;

bb) LC-medium additionally comprising one or more compounds selected from the following formulae:

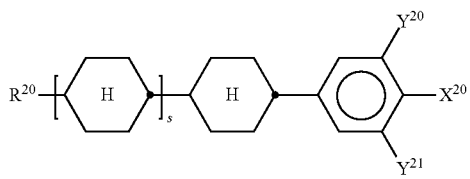
IV

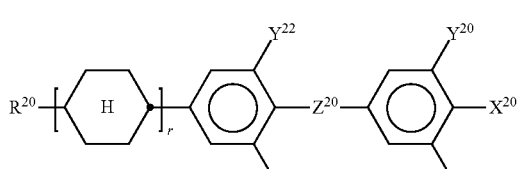
V

-continued

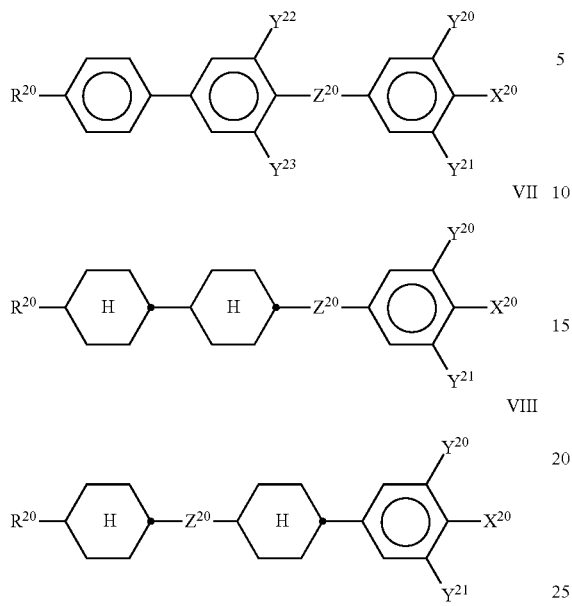

wherein
$R^{20}$, $X^{20}$ and $Y^{20-23}$ have the meanings indicated above, and
$Z^{20}$ denotes —$C_2H_4$—, —$(CH_2)_4$—, —CH=CH—, —CF=CF—, —$C_2F_4$—, —$CH_2CF_2$—, —$CF_2CH_2$—, —$CH_2O$—, —$OCH_2$—, —COO— or —$OCF_2$—, in formulae V and VI also a single bond, in formulae V and VIII also —$CF_2O$—,
r denotes 0 or 1, and
s denotes 0 or 1;

The compounds of the formula IV are preferably selected from the following formulae:

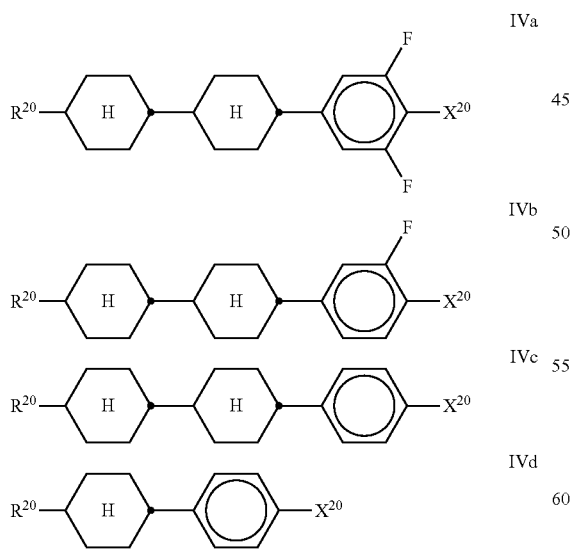

wherein $R^{20}$ and $X^{20}$ have the meanings indicated above. $R^{20}$ preferably denotes alkyl having 1 to 6 C atoms. $X^{20}$ preferably denotes F or $OCF_3$, furthermore OCF=$CF_2$ or Cl;

The compounds of the formula V are preferably selected from the following formulae:

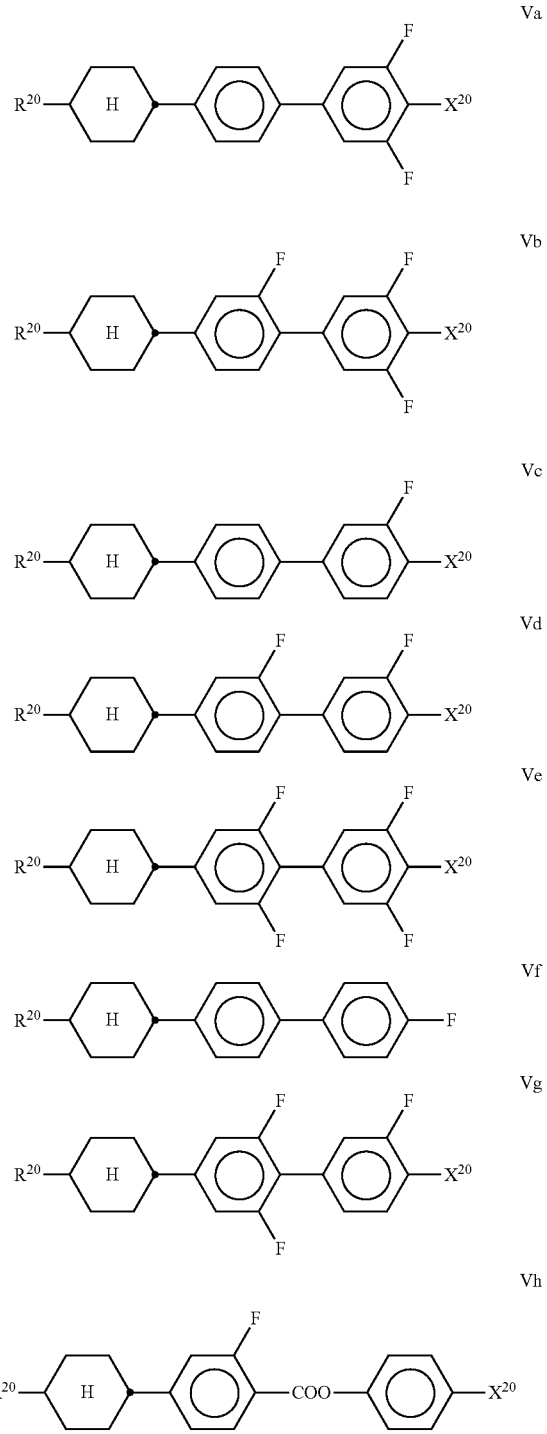

wherein $R^{20}$ and $X^{20}$ have the meanings indicated above. $R^{20}$ preferably denotes alkyl having 1 to 6 C atoms. $X^{20}$ preferably denotes F and $OCF_3$, furthermore $OCHF_2$, $CF_3$, OCF=$CF_2$ and OCH=$CF_2$;

The compounds of the formula VI are preferably selected from the following formulae:

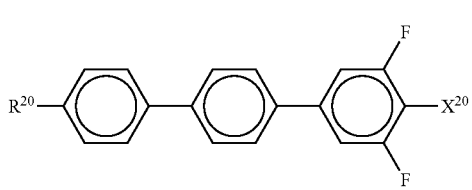
VIa

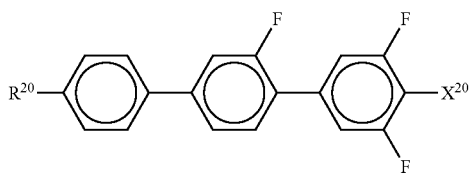
VIb

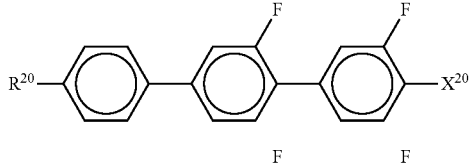
VIc

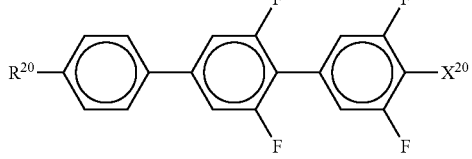
VId wherein $R^{20}$ and $X^{20}$ have the meanings indicated above. $R^{20}$ preferably denotes alkyl having 1 to 6 C atoms. $X^{20}$ preferably denotes F, furthermore $OCF_3$, $CF_3$, $CF=CF_2$, $OCHF_2$ and $OCH=CF_2$;

The compounds of the formula VII are preferably selected from the following formulae:

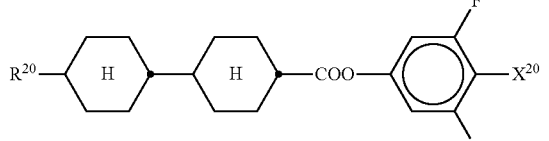
VIIa

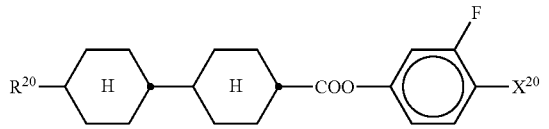
VIIb wherein $R^{20}$ and $X^{20}$ have the meanings indicated above. $R^{20}$ preferably denotes alkyl having 1 to 6 C atoms. $X^{20}$ preferably denotes F, furthermore $OCF_3$, $OCHF_2$ and $OCH=CF_2$.

cc) The medium additionally comprises one or more compounds selected from the formulae ZK1 to ZK10 given above. Especially preferred are compounds of formula ZK1 and ZK3. Particularly preferred compounds of formula ZK are selected from the sub-formulae ZK1a, ZK1b, ZK1c, ZK3a, ZK3b, ZK3c and ZK3d.

dd) The medium additionally comprises one or more compounds selected from the formulae DK1 to DK12 given above. Especially preferred compounds are DK3.

ee) The medium additionally comprises one or more compounds selected from the following formulae:

IX wherein $X^{20}$ has the meanings indicated above, and
L denotes H or F,
"alkenyl" denotes $C_{2-6}$-alkenyl.

ff) The compounds of the formulae DK-3a and IX are preferably selected from the following formulae:

DK3a

IXa wherein "alkyl" denotes $C_{1-6}$-alkyl, preferably n-$C_3H_7$, n-$C_4H_9$ or n-$C_5H_{11}$, in particular n-$C_3H_7$.

gg) The medium additionally comprises one or more compounds selected from the formulae B1, B2 and B3 given above, preferably from the formula B2. The compounds of the formulae B1 to B3 are particularly preferably selected from the formulae B1a, B2a, B2b and B2c.

hh) The medium additionally comprises one or more compounds selected from the following formula:

X wherein $L^{20}$ denotes H or F, and $R^{21}$ and $R^{22}$ each, identically or differently, denote n-alkyl, alkoxy, oxaalkyl, fluoroalkyl or alkenyl, each having up to 6 C atoms, and preferably each, identically or differently, denote alkyl having 1 to 6 C atoms.

ii) The medium comprises one or more compounds of the following formulae:

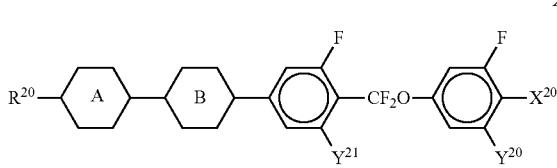
XI

XII
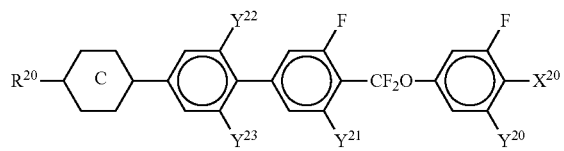
wherein $R^{20}$, $X^{20}$ and $Y^{20-23}$ have the meanings indicated in formula I, and
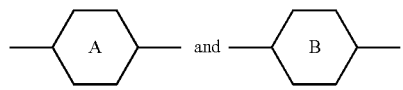
and each, independently of one another, denote
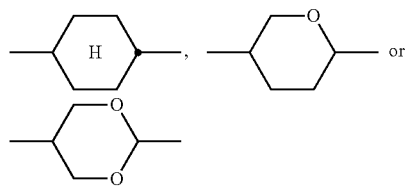
and
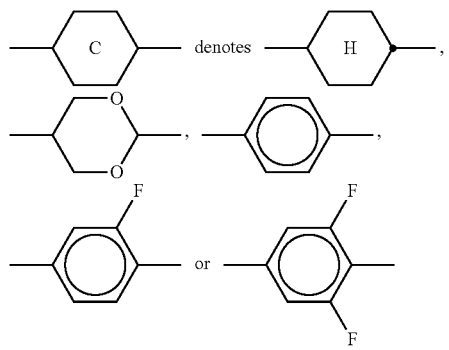
The compounds of the formulae XI and XII are preferably selected from the following formulae:
XIa
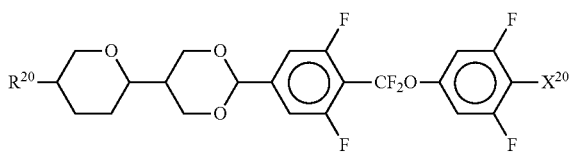
XIb
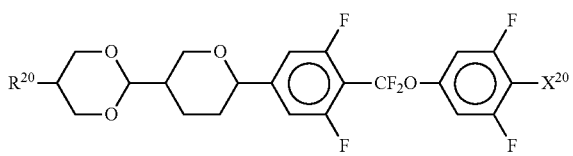
XIc
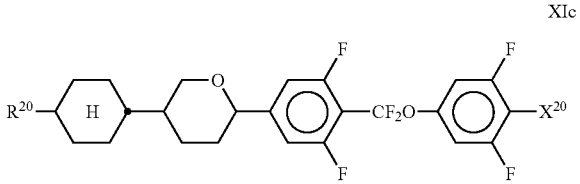
XId
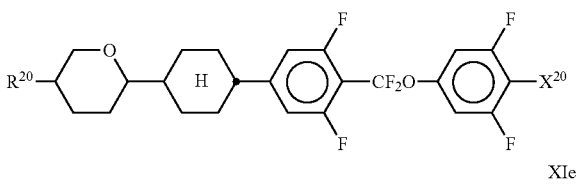
XIe
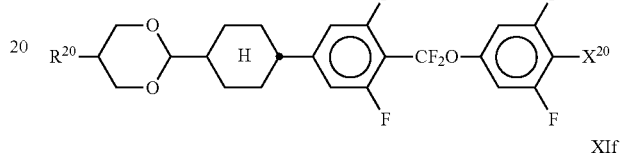
XIf
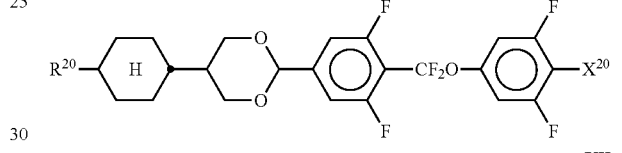
XIIa
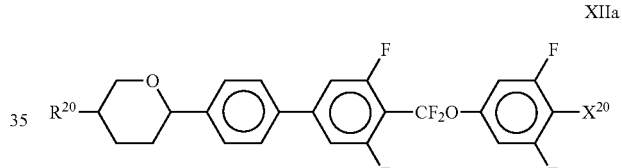
XIIb
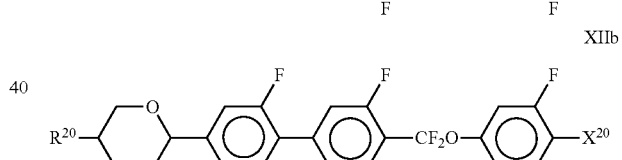
XIIc
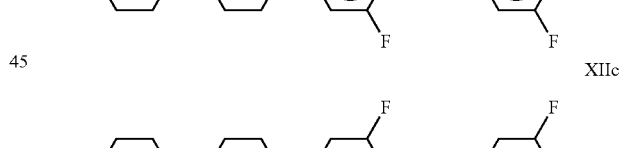
XIId
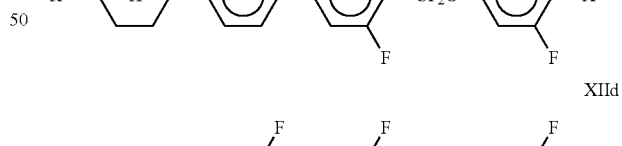
XIIe
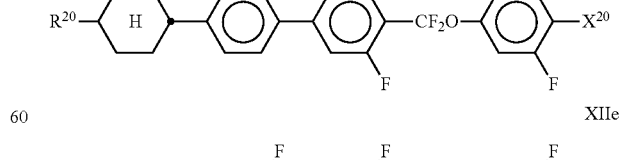

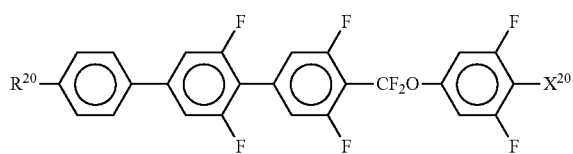
XIIf wherein R²⁰ and X²⁰ have the meaning indicated above and preferably R²⁰ denotes alkyl having 1 to 6 C atoms and X²⁰ denotes F.

The mixture according to the invention particularly preferably comprises at least one compound of the formula XIIa and/or XIIe.

jj) The medium comprises one or more compounds of formula T given above, preferably selected from the group of compounds of the formulae T21 to T23 and T25 to T27.

Particular preference is given to the compounds of the formulae T21 to T23. Very particular preference is given to the compounds of the formulae

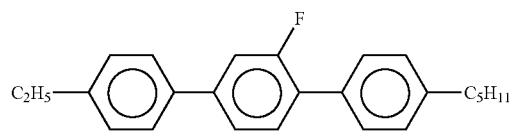

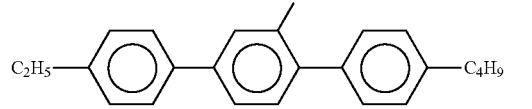

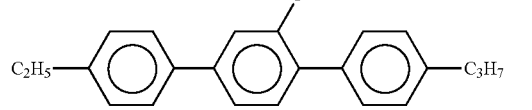

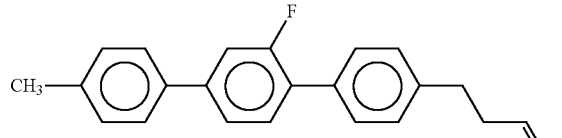

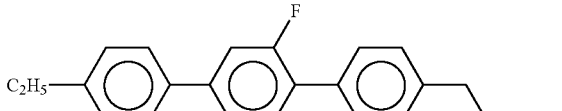

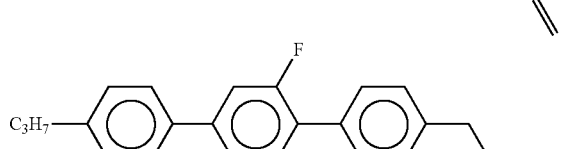

kk) The medium comprises one or more compounds selected from the group of formulae DK9, DK10 and DK11 given above.

ll) The medium additionally comprises one or more compounds selected from the following formulae:

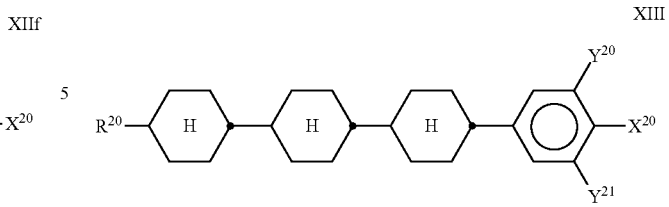
XIII

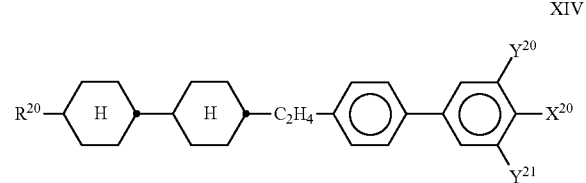
XIV

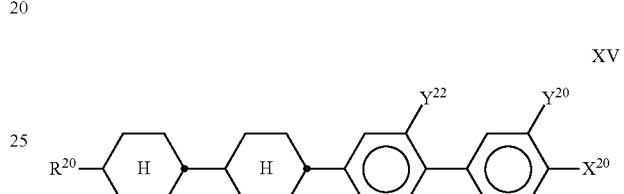
XV

XVI

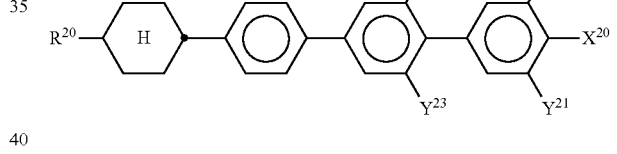
XVII

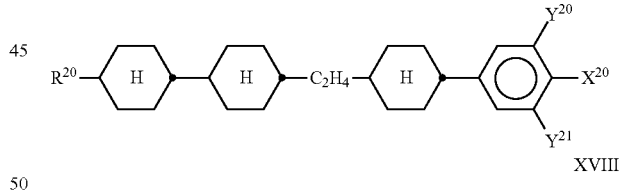
XVIII

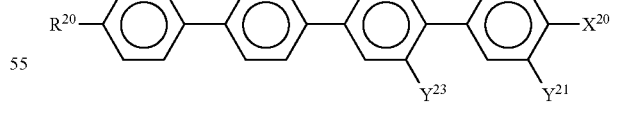

wherein R²⁰ and X²⁰ each, independently of one another, have one of the meanings indicated above, and Y²⁰⁻²³ each, independently of one another, denote H or F. X²⁰ is preferably F, Cl, CF₃, OCF₃ or OCHF₂. R²⁰ preferably denotes alkyl, alkoxy, oxaalkyl, fluoroalkyl or alkenyl, each having up to 6 C atoms.

The mixture according to the invention particularly preferably comprises one or more compounds of the formula XVIII-a, XVIII-a

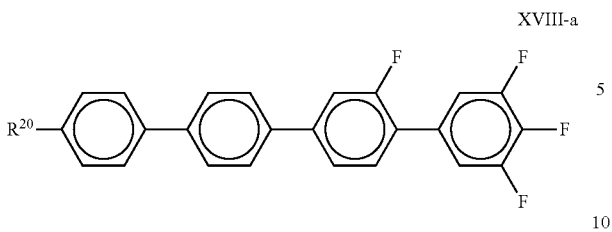

wherein $R^{20}$ has the meanings indicated above. $R^{20}$ preferably denotes straight-chain alkyl, in particular ethyl, n-propyl, n-butyl and n-pentyl and very particularly preferably n-propyl. The compound(s) of the formula XVIII, in particular of the formula XVIII-a, is (are) preferably employed in the mixtures according to the invention in amounts of 0.5-20% by weight, particularly preferably 1-15% by weight.

mm) The medium additionally comprises one or more compounds of the formula XIX,

XIX

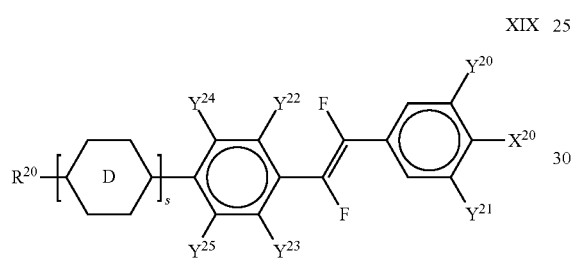

wherein $R^{20}$, $X^{20}$ and $Y^{20-25}$ have the meanings indicated in formula I, s denotes 0 or 1, and

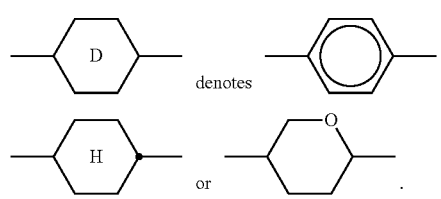

In the formula XIX, $X^{20}$ may also denote an alkyl radical having 1-6 C atoms or an alkoxy radical having 1-6 C atoms. The alkyl or alkoxy radical is preferably straight-chain.

$R^{20}$ preferably denotes alkyl having 1 to 6 C atoms. $X^{20}$ preferably denotes f;

The compounds of the formula XIX are preferably selected from the following formulae:

XIXa

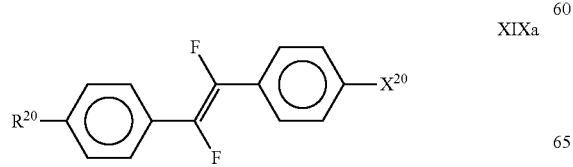

-continued

XIXb

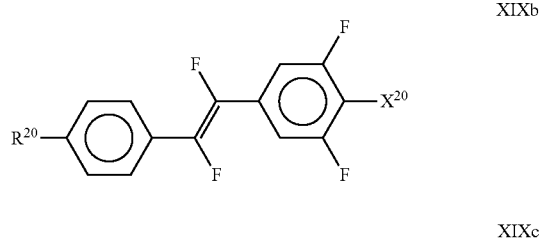

XIXc

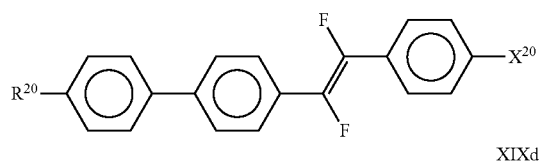

XIXd

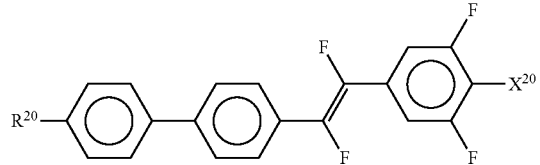

XIXe

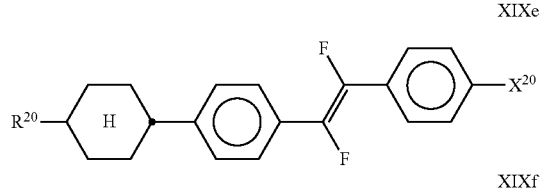

XIXf

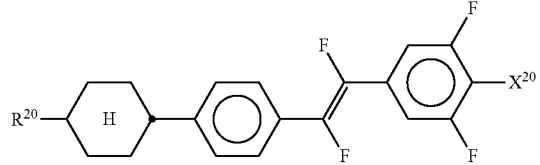

XIXg

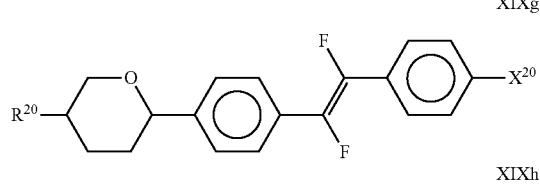

XIXh

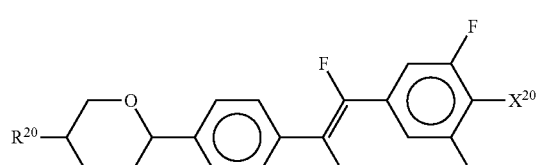

wherein $R^{20}$, $X^{20}$ and $Y^{20}$ have the meanings indicated above. $R^{20}$ preferably denotes alkyl having 1 to 6 C atoms. $X^{20}$ preferably denotes F, and $Y^{20}$ is preferably F;

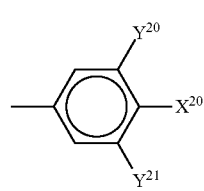

is preferably

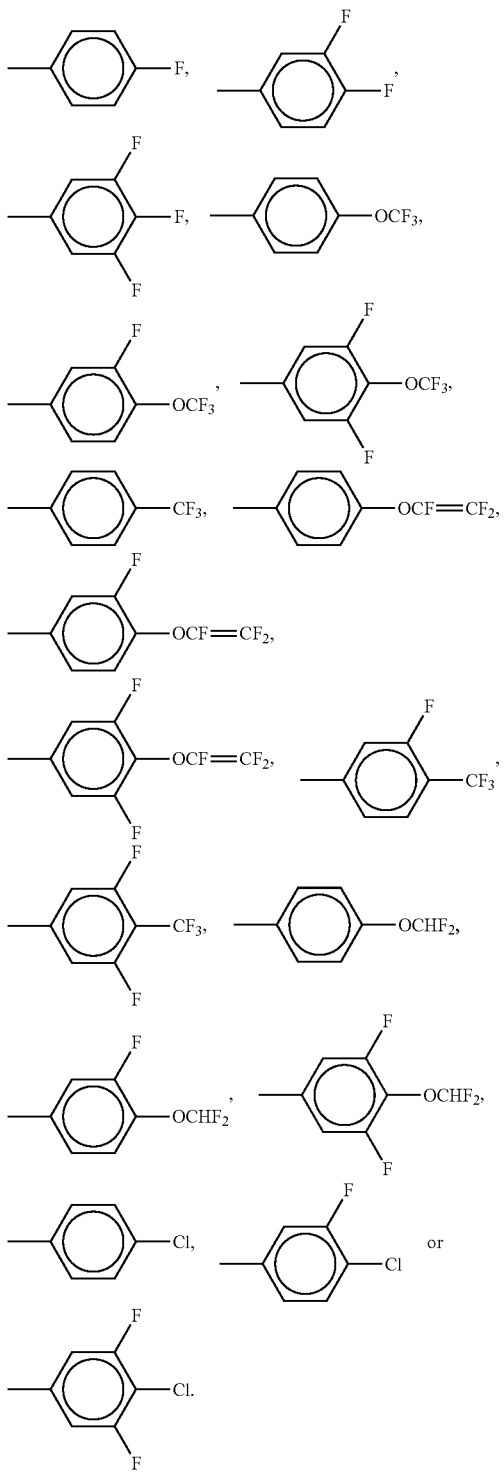

$R^{20}$ is straight-chain alkyl or alkenyl having 2 to 6 C atoms;

nn) The medium comprises one or more compounds of the formulae G1 to G4 given above, preferably selected from G1 and G2 wherein alkyl denotes $C_{1-6}$-alkyl, $L^x$ denotes H and X denotes F or Cl. In G2, X particularly preferably denotes Cl.

oo) The medium comprises one or more compounds of the following formulae:

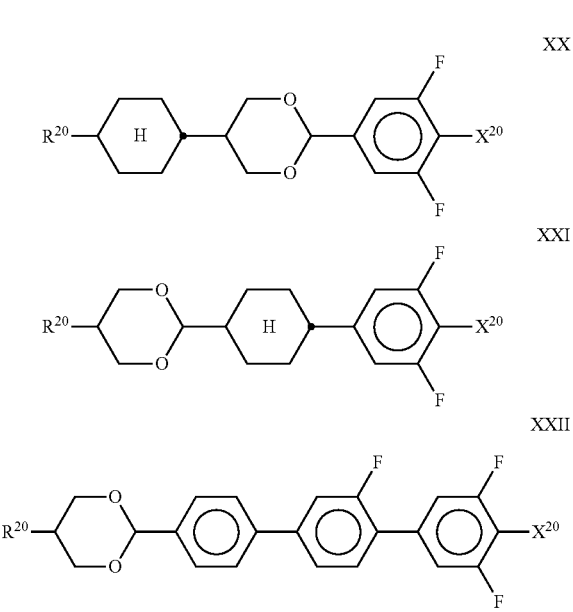

wherein $R^{20}$ and $X^{20}$ have the meanings indicated above. $R^{20}$ preferably denotes alkyl having 1 to 6 C atoms. $X^{20}$ preferably denotes F. The medium according to the invention particularly preferably comprises one or more compounds of the formula XXII wherein $X^{20}$ preferably denotes F. The compound(s) of the formulae XX-XXII is (are) preferably employed in the mixtures according to the invention in amounts of 1-20% by weight, particularly preferably 1-15% by weight. Particularly preferred mixtures comprise at least one compound of the formula XXII.

pp) The medium comprises one or more compounds of the following pyrimidine or pyridine compounds of the formulae

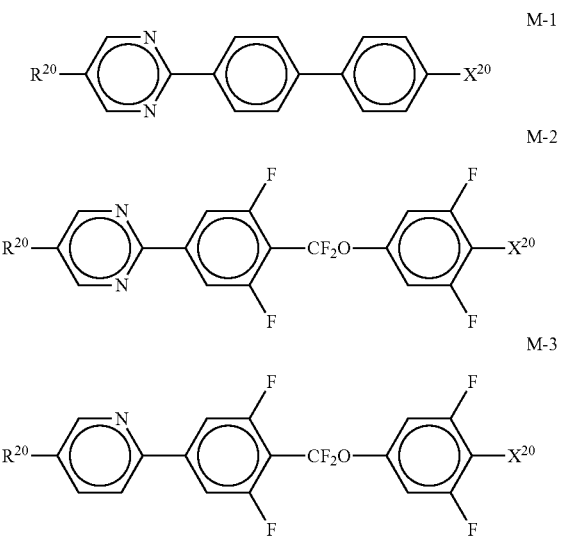

wherein $R^{20}$ and $X^{20}$ have the meanings indicated above. $R^{20}$ preferably denotes alkyl having 1 to 6 C atoms. $X^{20}$ preferably denotes F. The medium according to the invention particularly preferably comprises one or more compounds of the formula M-1, wherein $X^{20}$ preferably denotes F. The compound(s) of the formulae M-1-M-3 is (are) preferably employed in the mixtures according to the invention in amounts of 1-20% by weight, particularly preferably 1-15% by weight.

Further preferred embodiments are indicated below:

qq) The medium comprises two or more compounds of the formula XII, in particular of the formula XIIe;

rr) The medium comprises 2-30% by weight, preferably 3-20% by weight, particularly preferably 3-15% by weight, of compounds of the formula XII;

ss) Besides the compounds of the formula XII, the medium comprises further compounds selected from the group of the compounds of the formulae II, III, IX-XI, XIII, XVII and XVIII;

tt) The proportion of compounds of the formulae II, III, IX-XIII, XVII and XVIII in the mixture as a whole is 40 to 95% by weight;

uu) The medium comprises 10-50% by weight, particularly preferably 12-40% by weight, of compounds of the formulae II and/or III;

vv) The medium comprises 20-70% by weight, particularly preferably 25-65% by weight, of compounds of the formulae IX-XIII;

ww) The medium comprises 4-30% by weight, particularly preferably 5-20% by weight, of compounds of the formula XVII;

xx) The medium comprises 1-20% by weight, particularly preferably 2-15% by weight, of compounds of the formula XVIII;

yy) The medium comprises at least two compounds of the formulae

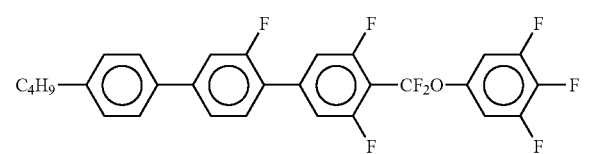

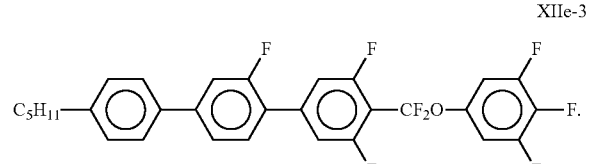

zz The medium comprises at least two compounds of the formulae

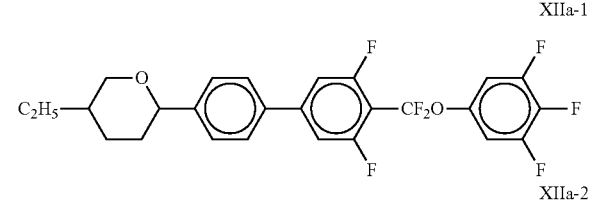

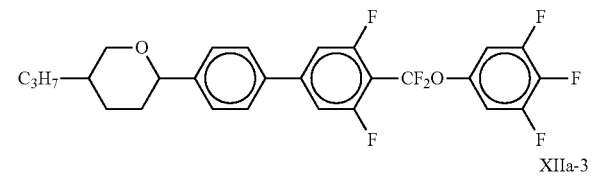

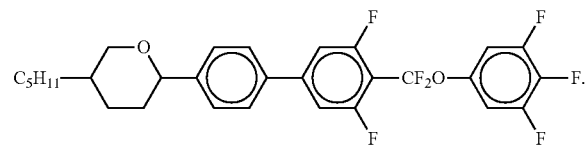

aaa) The medium comprises at least two compounds of the formula XIIa and at least two compounds of the formula XIIe.

bbb) The medium comprises at least one compound of the formula XIIa and at least one compound of the formula XIIe and at least one compound of the formula IIIa.

ccc) The medium comprises at least two compounds of the formula XIIa and at least two compounds of the formula XIIe and at least one compound of the formula IIIa.

ddd) The medium comprises in total >25% by weight, preferably >30% by weight, of one or more compounds of the formula XII.

eee) The medium comprises ≥20% by weight, preferably ≥24% by weight, preferably 25-60% by weight, of compounds of the formula ZK3, in particular the compound of the formula ZK3a,

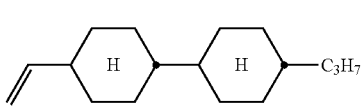

fff) The medium comprises at least one compound selected from the group of compounds ZK3a, ZK3b and ZK3c, preferably ZK3a, in combination with compound ZK3d

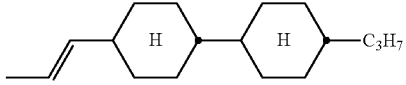

ggg) The medium comprises at least one compound of the formula DPGU-n-F.

hhh) The medium comprises at least one compound of the formula CDUQU-n-F.

iii) The medium comprises at least one compound of the formula CPU-n-OXF.

jjj) The medium comprises at least one compound of the formula CPGU-3-OT.

kkk) The medium comprises at least one compound of the formula PPGU-n-F.

lll) The medium comprises at least one compound of the formula PGP-n-m, preferably two or three compounds.

mmm) The medium comprises at least one compound of the formula PGP-2-2V having the structure

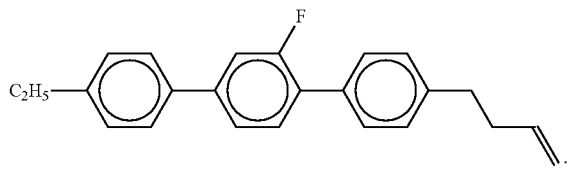

The media according to the invention preferably comprise from 0.01 to 10%, particularly preferably from 0.05 to 5% and most preferably from 0.1 to 3% of compounds of formula S according to the invention. The media preferably comprise one, two or three, more preferably one or two and most preferably one compound of the formula S according to the invention.

The media according to the invention preferably comprise from 0.01 to 10%, particularly preferably from 0.05 to 7.5% and most preferably from 2 to 5% of the of formula P according to the invention. The media preferably comprise one, two or three, more preferably one or two and most preferably one compound of the formula P according to the invention.

The compounds used in the present invention are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

In the following, the production process according to the present invention is described in greater detail.

In one embodiment of the present invention the liquid crystal composition is injected between the first and second substrates or is filled into the cell by capillary force after combining the first and second substrates. In an alternative embodiment, the liquid crystal composition may be interposed between the first and second substrates by combining the second substrate to the first substrate after loading the liquid crystal composition on the first substrate. Preferably, the liquid crystal is dispensed dropwise onto a first substrate in a process known as "one drop filling" (ODF) process, as disclosed in for example JPS63-179323 and JPH10-239694.

For the production of the displays according to the present invention, the SAPA of formula S is preferably allowed to self assemble after filling and assembly of the display panel for a time between 1 min and 3 h, preferably between 10 min and 1 h and most preferably between 20 min and 30 min. The self assembly is preferably performed at room temperature.

In an alternative embodiment, the self assembly is performed at elevated temperature, preferably at above 20° C. and below 120° C., more preferably above 40° C. and below 100° C. and most preferably above 50° C. and below 80° C.

In a preferred embodiment, one or more of the process steps of filling the display, self assembly of the SAPA, photoalignment and curing of the polymerisable compound is performed at a temperature above the clearing point of the liquid crystal host mixture.

During the photoalignment of the liquid crystal inside the liquid crystal panel, anisotropy is induced by exposing the display or the liquid crystal layer to linearly polarised light from an oblique direction.

In a first preferred embodiment of the present invention the SAPA is photoaligned in a first step using linearly polarised light and cured, in case the SAPA contains photopolymerisable groups, in a second step using UV light. In the second step, the optional compound of formula P is also cured.

In a second preferred embodiment the linearly polarised light applied according to the inventive process is ultraviolet light which enables simultaneous photoalignment and photocuring of the SAPA and, if present, photocuring of the polymerisable compound of formula P.

The polymerisable compounds of formula P are optionally polymerised or crosslinked (if a polymerisable compound contains two or more polymerisable groups) with application of a voltage. The polymerisation can be carried out in one step or in more than one step ("end curing").

According to the present invention, an alkyl radical and/or an alkoxy radical may be straight-chain or branched. It is preferably straight-chain, has 2, 3, 4, 5, 6 or 7 C atoms and accordingly preferably denotes ethyl, propyl, butyl, pentyl, hexyl, heptyl, ethoxy, propoxy, butoxy, pentoxy, hexyloxy or -heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl preferably denotes straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxa-decyl.

An alkyl radical in which one CH2 group has been replaced by —CH═CH—, may be straight-chain or branched. It is preferably straight-chain and has 2 to 10 C atoms. Accordingly, it denotes, in particular, vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, dec-1-, -2-, -3-, -4-, -5-, -6-, -7-, -8- or -9-enyl.

An alkyl or alkenyl radical which is at least monosubstituted by halogen is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

In the formulae above and below, polar end groups (substituents X) are preferably F, Cl or a mono- or polyfluorinated alkyl or alkoxy radical having 1, 2 or 3 C atoms or a mono- or polyfluorinated alkenyl radical having 2 or 3 C atoms. They are particularly preferably F, Cl, $CF_3$, $CHF_2$, $OCF_3$, $OCHF_2$, $OCFHCF_3$, $OCFHCHF_2$, $OCFHCHF_2$, $OCF_2CH_3$, $OCF_2CHF_2$, $OCF_2CHF_2$, $OCF_2CF_2CHF_2$, $OCF_2CF_2CHF_2$, $OCFHCF_2CF_3$, $OCFHCF_2CHF_2$, $OCF_2CF_2CF_3$, $OCF_2CF_2CClF_2$, $OCClFCF_2CF_3$, $OCH{=}CF_2$ or $CH{=}CF_2$, very particularly preferably F or $OCF_3$, furthermore $CF_3$, $OCF{=}CF_2$, $OCHF_2$ or $OCH{=}CF_2$.

The media according to the invention are prepared in a manner conventional per se. In general, the components are dissolved in one another, preferably at elevated temperature. By means of suitable additives, the liquid-crystalline phases of the present invention can be modified in such a way that they can be used in all types of liquid-crystal display element that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems or substances can be added in order to modify the dielectric anisotropy, the viscosity and/or the alignment of the nematic phases.

The present invention also relates to electro-optical liquid-crystal display elements containing a liquid-crystalline medium according to the invention.

Further combinations of the embodiments and variants of the invention in accordance with the description arise from the claims.

Besides the usual and well-known abbreviations, the following abbreviations are used:
C: crystalline phase; N: nematic phase; Sm: smectic phase; I: isotropic phase. The numbers between these symbols show the transition temperatures of the substance concerned.

Temperature data are in ° C., unless indicated otherwise.

Physical, physicochemical or electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt.

Above and below, Δn denotes the optical anisotropy (589 nm, 20° C.) and De denotes the dielectric anisotropy (1 kHz, 20° C.). The dielectric anisotropy De is determined at 20° C. and 1 kHz. The optical anisotropy Δn is determined at 20° C. and a wavelength of 589.3 nm.

The Δε and Δn values and the rotational viscosity ($\gamma_1$) of the compounds according to the invention are obtained by linear extrapolation from liquid-crystalline mixtures consisting of 5 to 10% of the respective compound according to the invention and 90-95% of the commercially available liquid-crystal mixture ZLI-2857 (for Δε) or ZLI-4792 (for Δn, $\gamma_1$) (mixtures, Merck KGaA, Darmstadt).

In the present invention and especially in the following examples, the structures of the mesogenic compounds are indicated by means of abbreviations, also called acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2n-1}$, $C_mH_{2m-1}$ and $C_lH_{2l-1}$ denote straight-chain alkyl or alkenyl, preferably 1E-alkenyl, each having n, m and l C atoms respectively. Table A lists the codes used for the ring elements of the core structures of the compounds, while Table B shows the linking groups. Table C gives the meanings of the codes for the left-hand or right-hand end groups. The acronyms are composed of the codes for the ring elements with optional linking groups, followed by a first hyphen and the codes for the left-hand end group, and a second hyphen and the codes for the right-hand end group. Table D shows illustrative structures of compounds together with their respective abbreviations.

TABLE A

Ring elements

| | |
|---|---|
| C |  |

TABLE A-continued

Ring elements

| | |
|---|---|
| P | 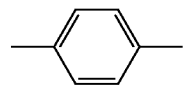 |
| D | 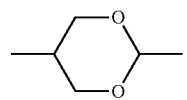 |
| DI | 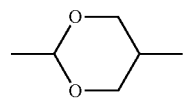 |
| A | 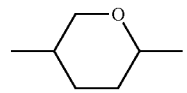 |
| AI | 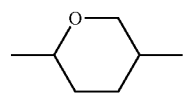 |
| G | 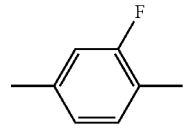 |
| GI | 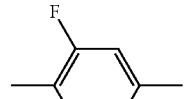 |
| U | 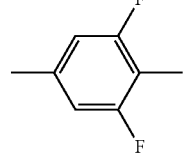 |
| UI | 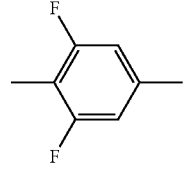 |
| Y | 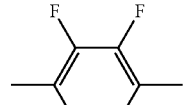 |
| M | 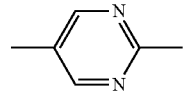 |
| MI | 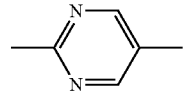 |

TABLE A-continued
Ring elements
| | |
|---|---|
| N | 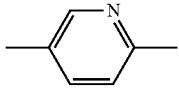 |
| NI | 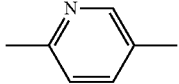 |
| Np | 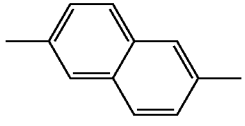 |
| dH | 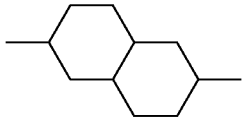 |
| N3f | 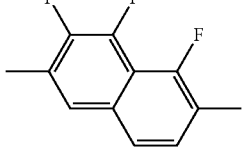 |
| N3fl | 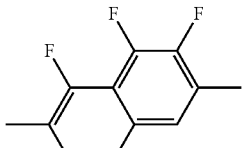 |
| tH | 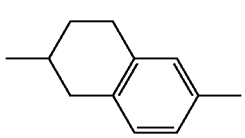 |
| tHI | 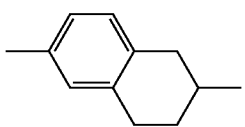 |
| tH2f | 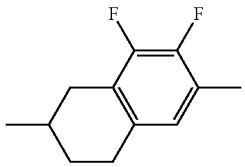 |
| tH2fl | 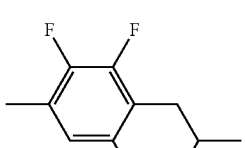 |
| K | 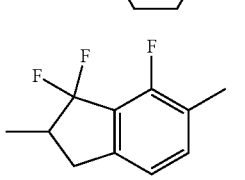 |
| KI | 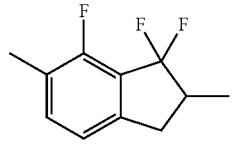 |
| L | 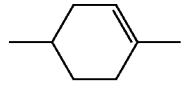 |
| LI | 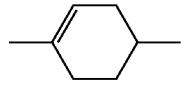 |
| F | 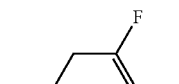 |
| FI | 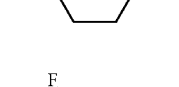 |
| Nf | 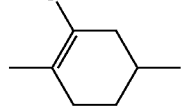 |
| Nfl | 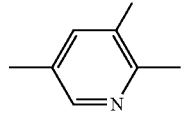 |
TABLE B
Linking groups
| | | | |
|---|---|---|---|
| E | —CH$_2$CH$_2$— | Z | —CO—O— |
| V | —CH=CH— | ZI | —O—CO— |
| X | —CF=CH— | O | —CH$_2$—O— |
| XI | —CH=CF— | OI | —O—CH$_2$— |
| B | —CF=CF— | Q | —CF$_2$—O— |
| T | —C≡C— | QI | —O—CF$_2$— |
| W | —CF$_2$CF$_2$— | T | —C≡C— |

TABLE C

| End groups | | | |
|---|---|---|---|
| Left-hand side | | Right-hand side | |
| Use alone | | | |
| -n- | $C_nH_{2n+1}$— | -n | —$C_nH_{2n+1}$ |
| -nO- | $C_nH_{2n+1}$—O— | -nO | —O—$C_nH_{2n+1}$ |
| -V- | $CH_2$=CH— | -V | —CH=$CH_2$ |
| -nV- | $C_nH_{2n+1}$—CH=CH— | -nV | —$C_nH_{2n}$—CH=$CH_2$ |
| -Vn- | $CH_2$=CH—$C_nH_{2n+1}$— | -Vn | —CH=CH—$C_nH_{2n+1}$ |
| -nVm- | $C_nH_{2n+1}$—CH=CH—$C_mH_{2m}$— | -nVm | —$C_nH_{2n}$—CH=CH—$C_mH_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | $CFH_2$— | -M | —$CFH_2$ |
| -D- | $CF_2H$— | -D | —$CF_2H$ |
| -T- | $CF_3$— | -T | —$CF_3$ |
| -MO- | $CFH_2O$— | -OM | —$OCFH_2$ |
| -DO- | $CF_2HO$— | -OD | —$OCF_2H$ |
| -TO- | $CF_3O$— | -OT | —$OCF_3$ |
| -FXO- | $CF_2$=CH—O— | -OXF | —O—CH=$CF_2$ |
| -A- | H—C≡C— | -A | —C≡C—H |
| -nA- | $C_nH_{2n+1}$—C≡C— | -An | —C≡C—$C_nH_{2n+1}$ |
| -NA- | N≡C—C≡C— | -AN | —C≡C—C≡N |
| Use together with one another and with others | | | |
| -...A...- | —C≡C— | -...A... | —C≡C— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | wherein n and m each denote integers, and the three dots " . . . " are place-holders for other abbreviations from this table.

The following table shows illustrative structures together with their respective abbreviations. These are shown in order to illustrate the meaning of the rules for the abbreviations. They furthermore represent compounds which are preferably used.

TABLE D

Illustrative structures

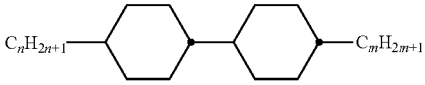

CC-n-m

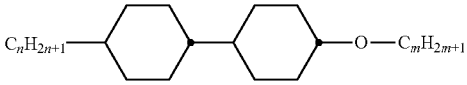

CC-n-Om

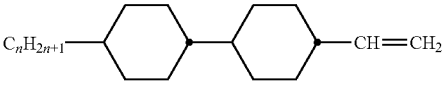

CC-n-V

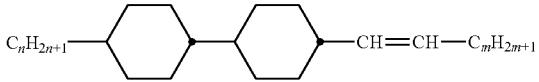

CC-n-Vm

TABLE D-continued
Illustrative structures
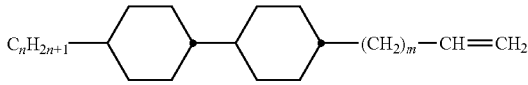
CC-n-mV
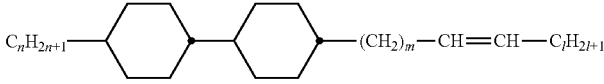
CC-n-mVl
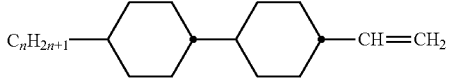
CC—V—V
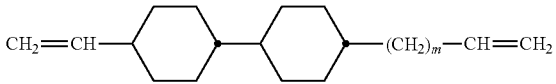
CC—V-mV
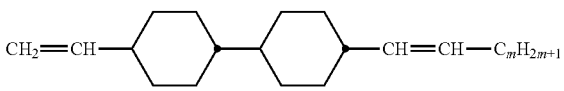
CC—V—Vm
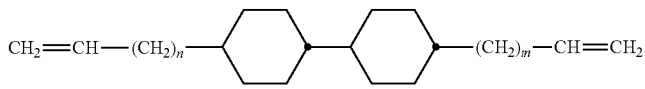
CC—Vn-mV
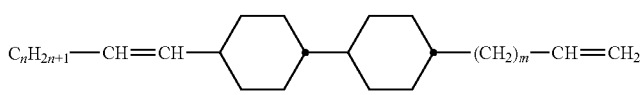
CC-nV-mV
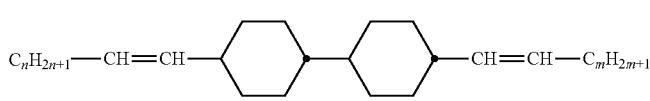
CC-nV—Vm
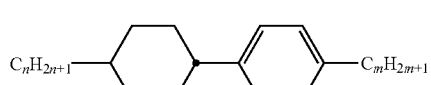
CP-n-m
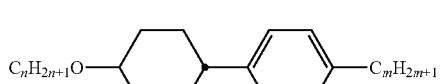
CP-nO-m
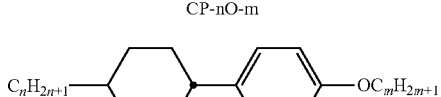
CP-n-Om TABLE D-continued
Illustrative structures
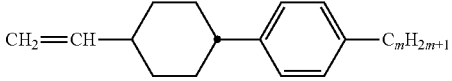
CP—V-m
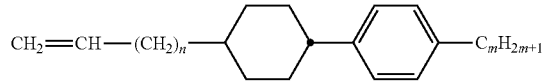
CP—Vn-m
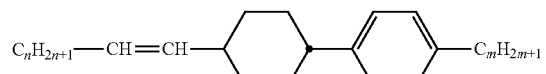
CP-nV-m
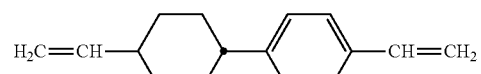
CP—V—V
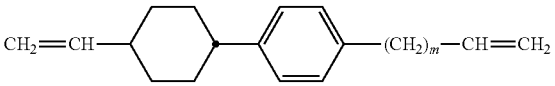
CP—V-mV
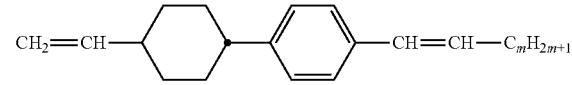
CP—V—Vm
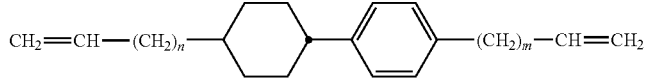
CP—Vn-mV
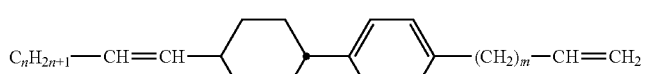
CP-nV-mV
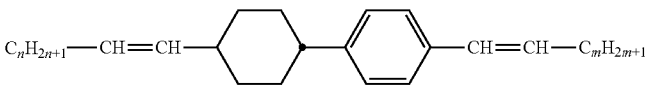
CP-nV—Vm
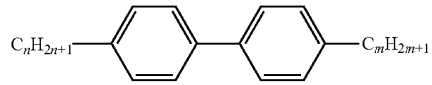
PP-n-m
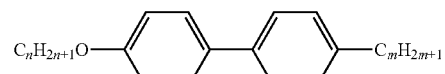
PP-nO-m TABLE D-continued
Illustrative structures
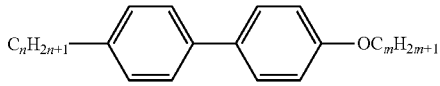
PP-n-Om
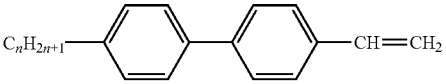
PP-n-V
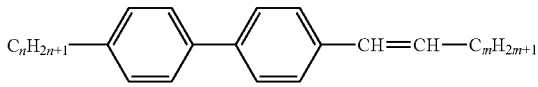
PP-n-Vm
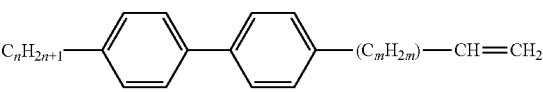
PP-n-mV
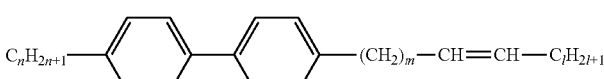
PP-n-mVl
CCP-n-m
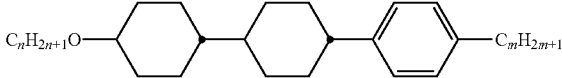
CCP-nO-m
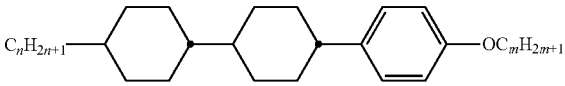
CCP-n-Om
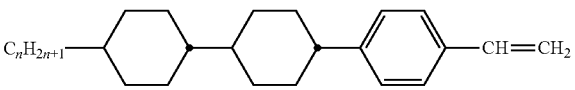
CCP-n-V
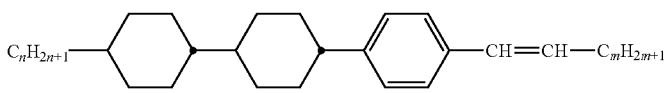
CCP-n-Vm
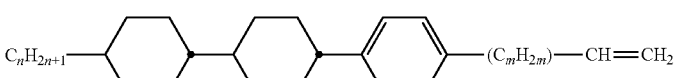
CCP-n-mV TABLE D-continued
Illustrative structures
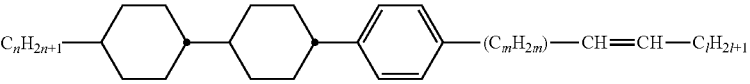
CCP-n-mVl
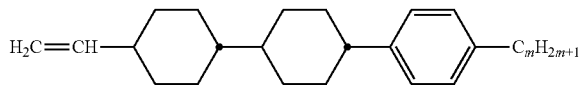
CCP—V-m
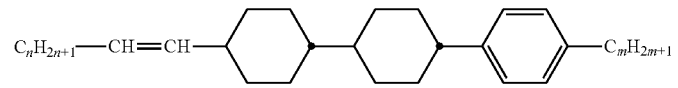
CCP-nV-m
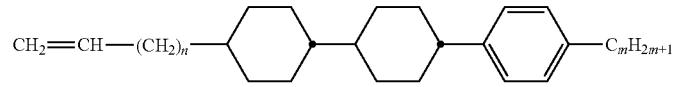
CCP—Vn-m
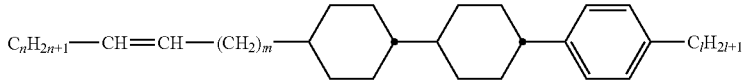
CCP-nVm-l
CPP-n-m
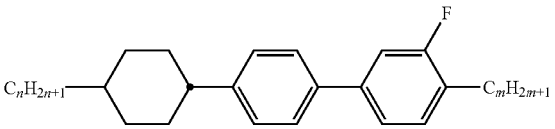
CPG-n-m
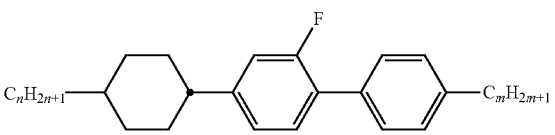
CGP-n-m
CPP-nO-m
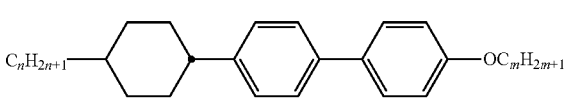
CPP-n-Om TABLE D-continued
Illustrative structures
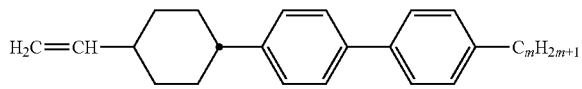
CPP—V-m
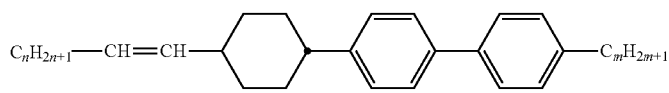
CPP-nV-m
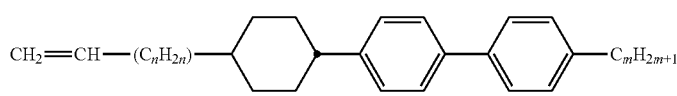
CPP—Vn-m
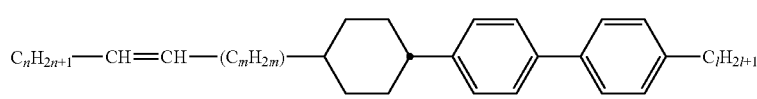
CPP-nVm-l
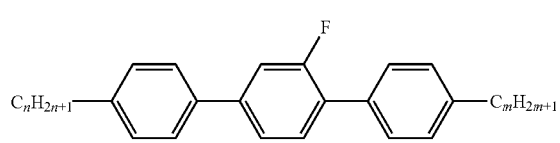
PGP-n-m
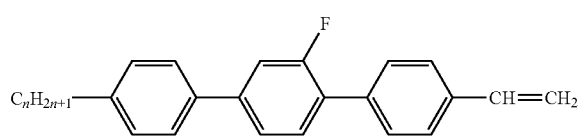
PGP-n-V
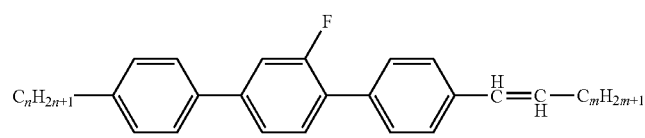
PGP-n-Vm
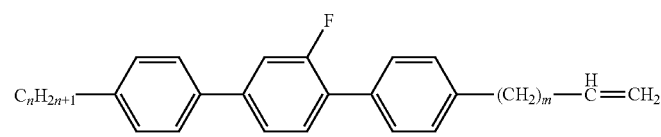
PGP-n-mV
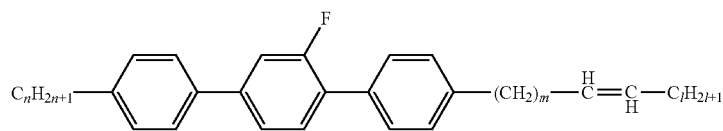
PGP-n-mVl TABLE D-continued
Illustrative structures
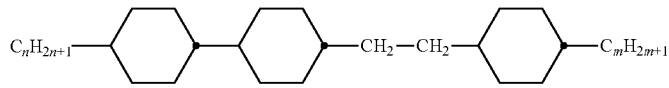
CCEC-n-m
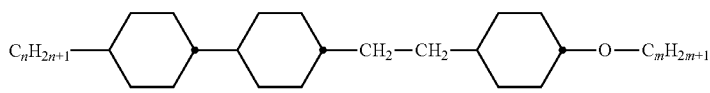
CCEC-n-Om
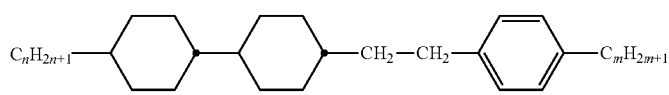
CCEP-n-m
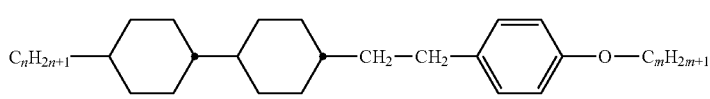
CCEP-n-Om
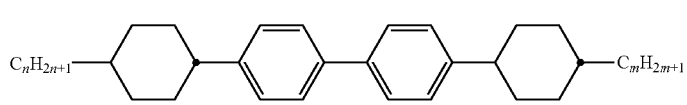
CPPC-n-m
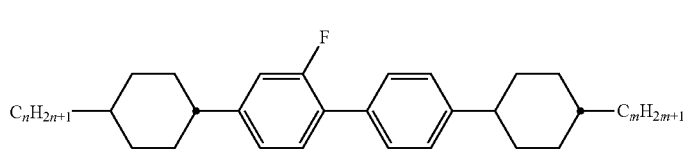
CGPC-n-m
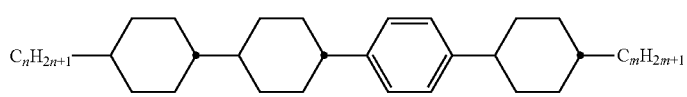
CCPC-n-m
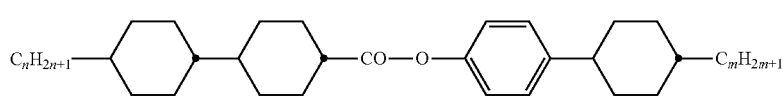
CCZPC-n-m
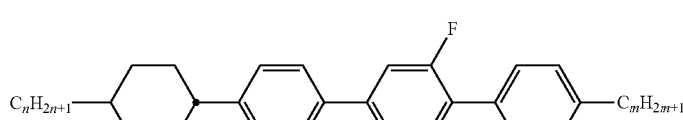
CPGP-n-m
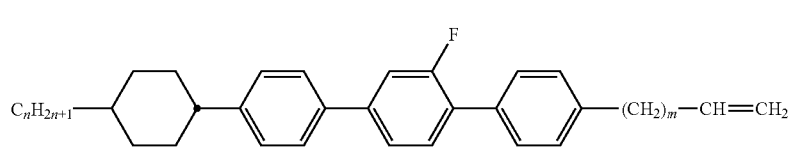
CPGP-n-mV TABLE D-continued
Illustrative structures
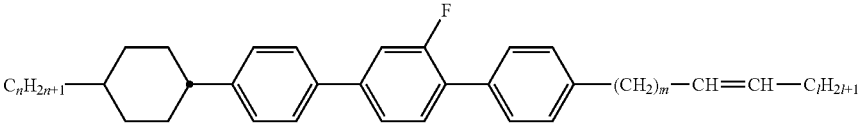
CPGP-n-mVl
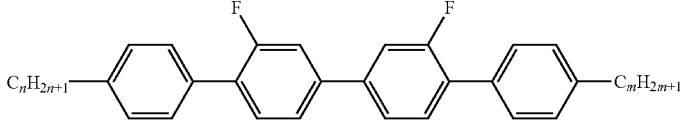
PGIGP-n-m
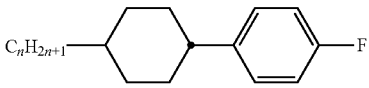
CP-n-F
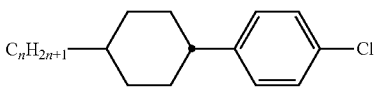
CP-n-CL
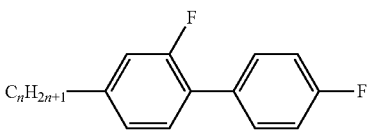
GP-n-F
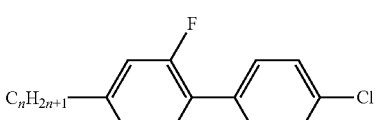
GP-n-CL
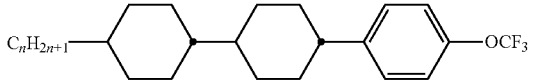
CCP-n-OT
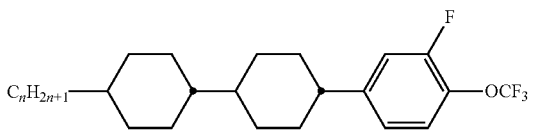
CCG-n-OT
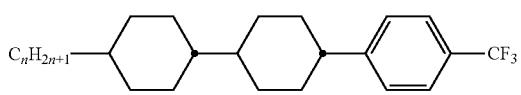
CCP-n-T TABLE D-continued
Illustrative structures
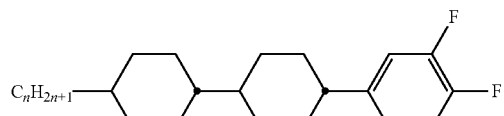
CCG-n-F
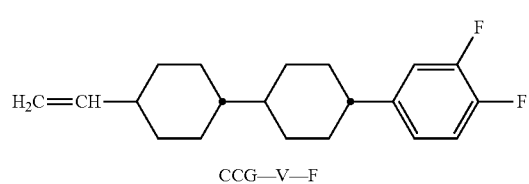
CCG—V—F
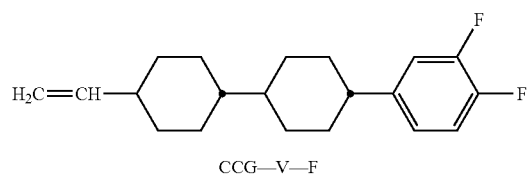
CCG—V—F
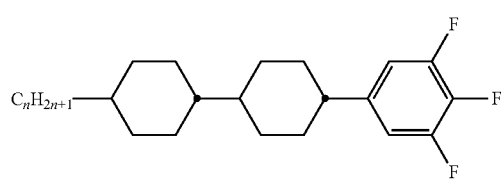
CCU-n-F
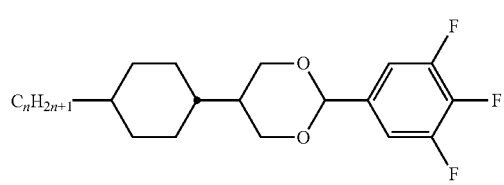
CDU-n-F
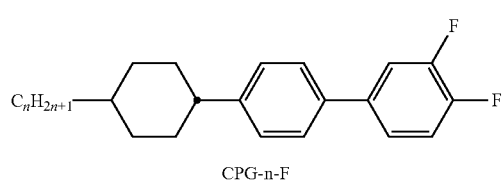
CPG-n-F
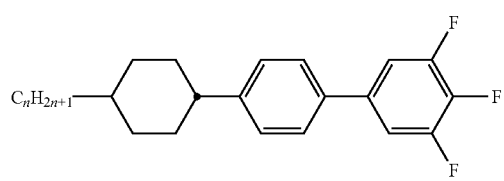
CPU-n-F
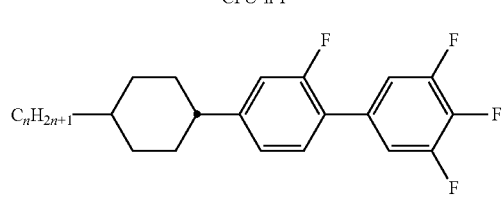
CGU-n-F TABLE D-continued
Illustrative structures
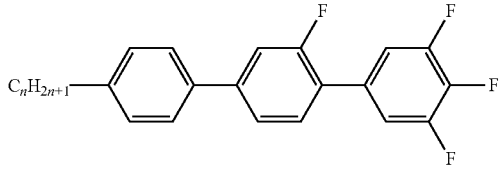
PGU-n-F
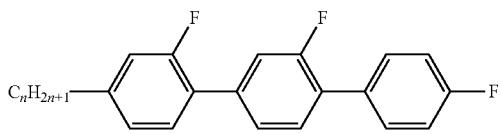
GGP-n-F
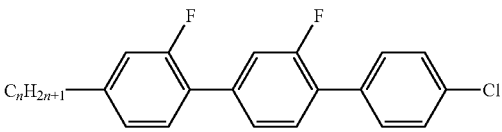
GGP-n-CL
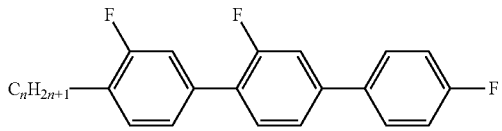
PGIGI-n-F
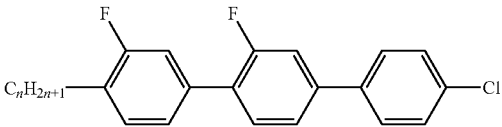
PGIGI-n-CL
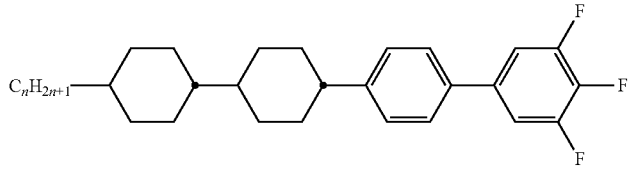
CCPU-n-F
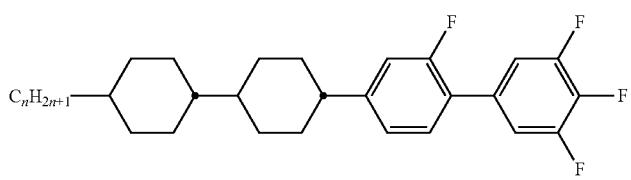
CCGU-n-F
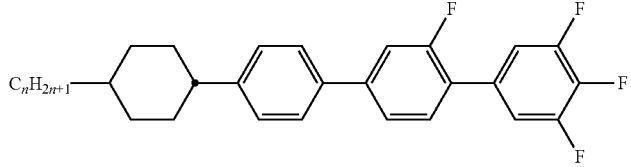
CPGU-n-F TABLE D-continued
Illustrative structures
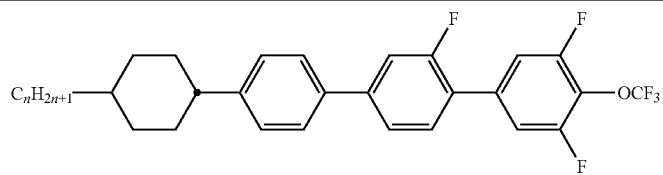
CPGU-n-OT
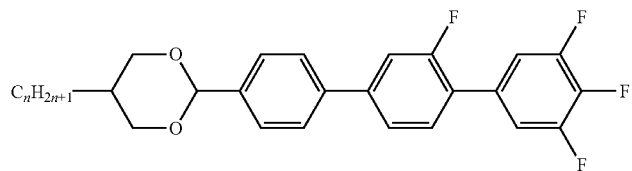
DPGU-n-F
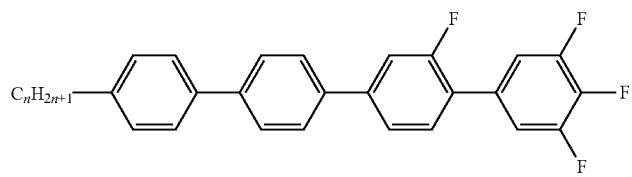
PPGU-n-F
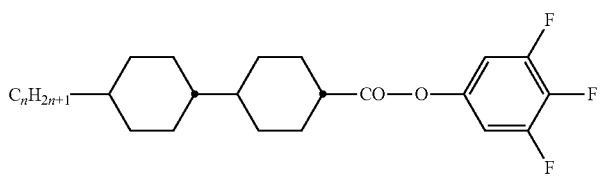
CCZU-n-F
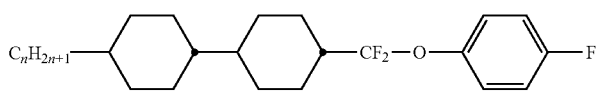
CCQP-n-F
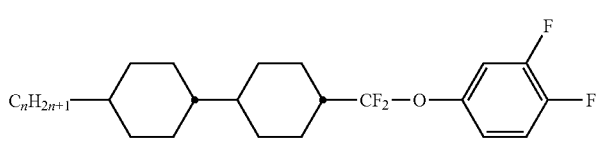
CCQG-n-F
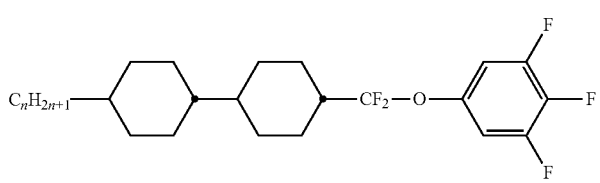
CCQU-n-F
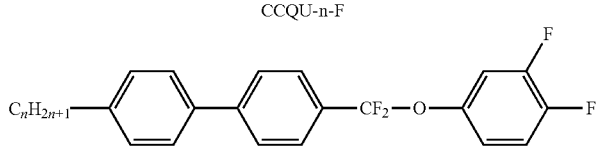
PPQG-n-F TABLE D-continued
Illustrative structures
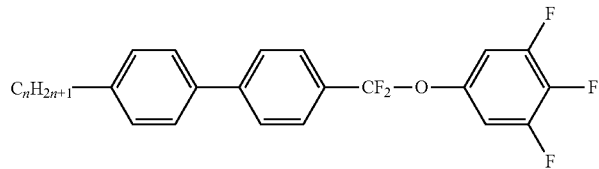
PPQU-n-F
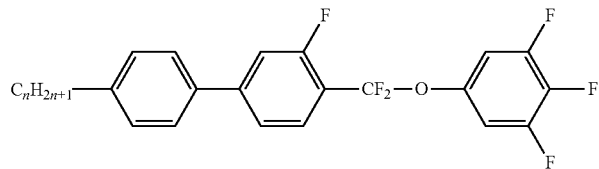
PGQU-n-F
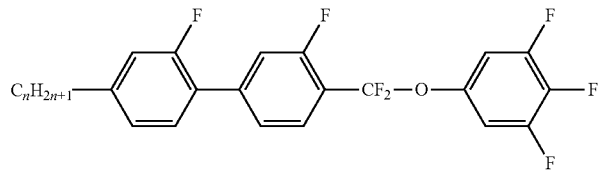
GGQU-n-F
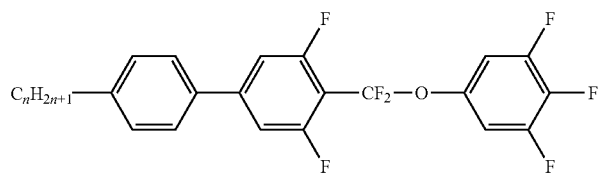
PUQU-n-F
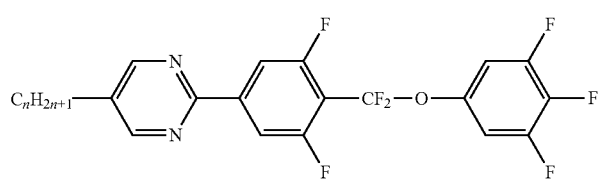
MUQU-n-F
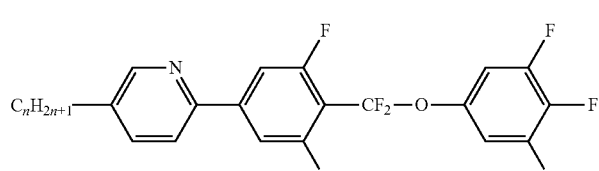
NUQU-n-F
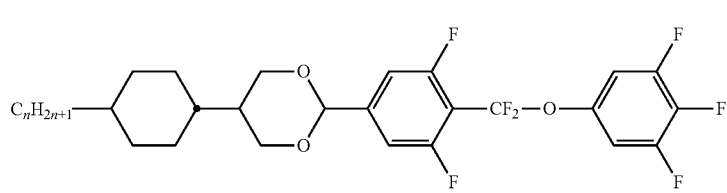
CDUQU-n-F TABLE D-continued
Illustrative structures
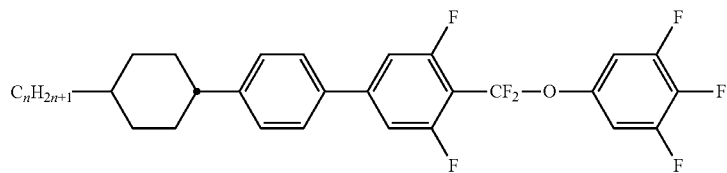
CPUQU-n-F
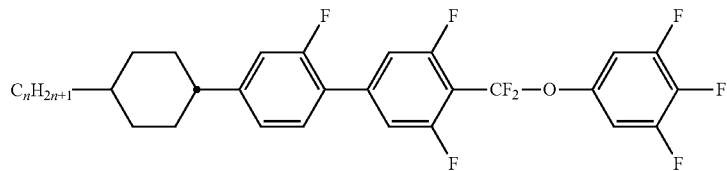
CGUQU-n-F
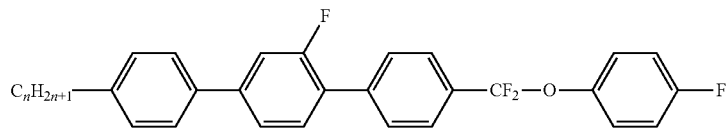
PGPQP-n-F
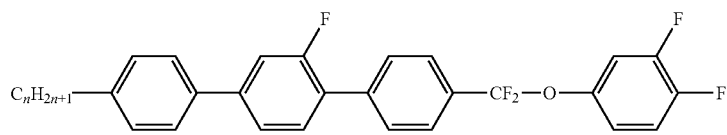
PGPQG-n-F
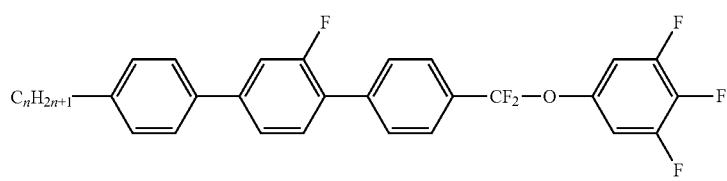
PGPQU-n-F
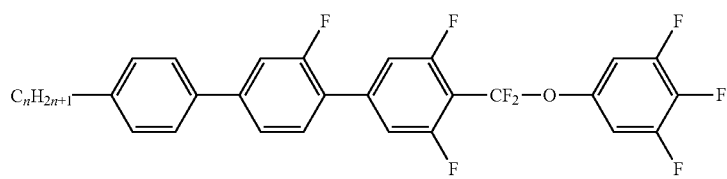
PGUQU-n-F
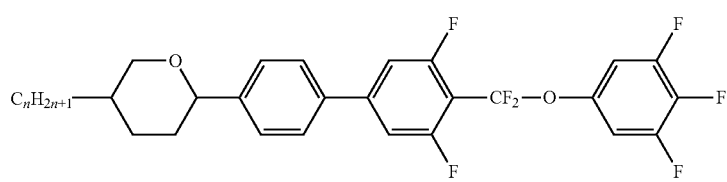
APUQU-n-F TABLE D-continued
Illustrative structures
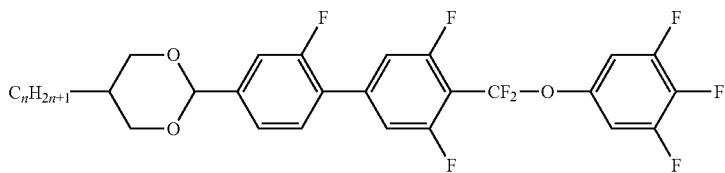
DGUQU-n-F
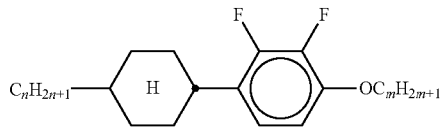
CY-n-Om
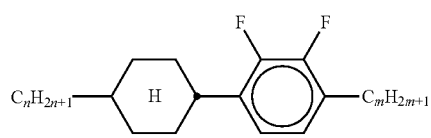
CY-n-m
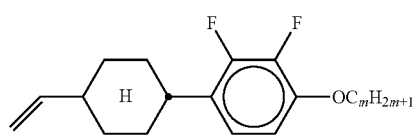
CY—V—Om
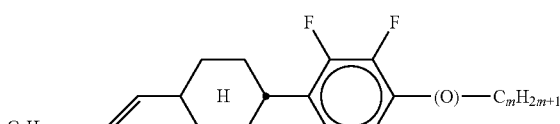
CY-nV—(O)m
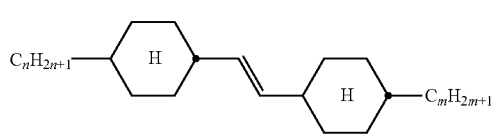
CVC-n-m
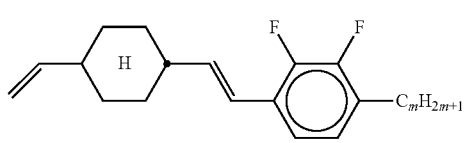
CVY—V-m
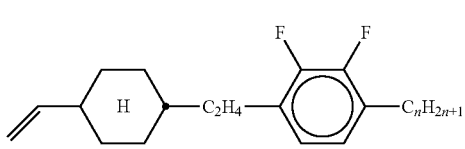
CEY—V-m TABLE D-continued
Illustrative structures
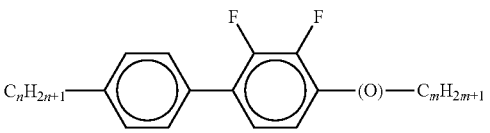
PY-n-(O)m
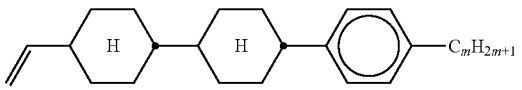
CCP—V-m
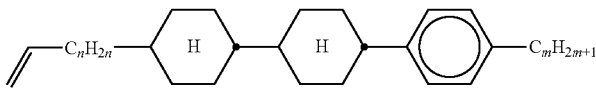
CCP—Vn-m
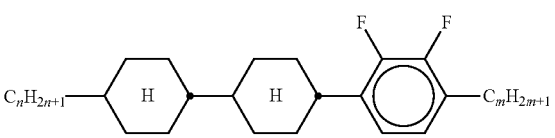
CCY-n-m
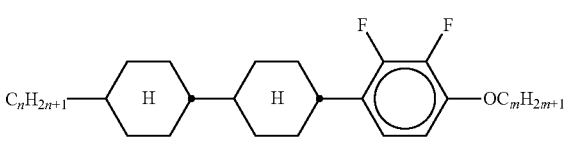
CCY-n-Om
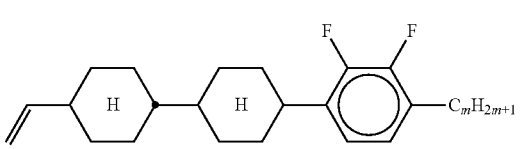
CCY—V-m
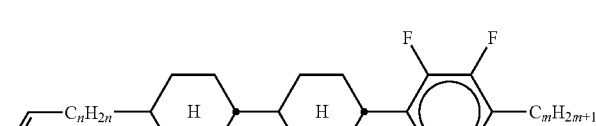
CCY—Vn-m
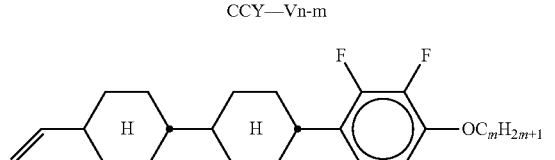
CCY—V—Om
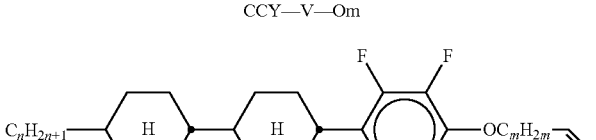
CCY-n-OmV TABLE D-continued
Illustrative structures
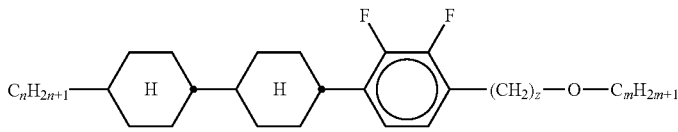
CCY-n-zOm
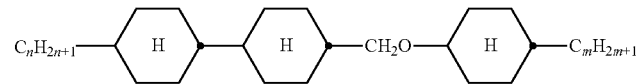
CCOC-n-m
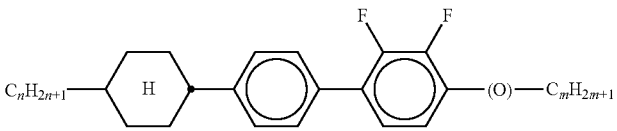
CPY-n-(O)m
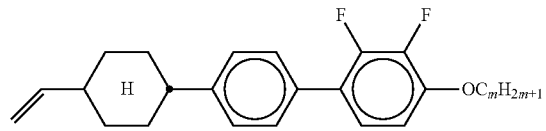
CPY—V—Om
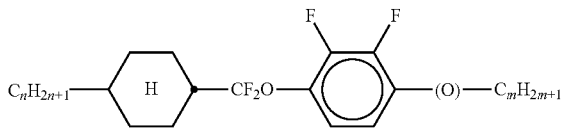
CQY-n-(O)m
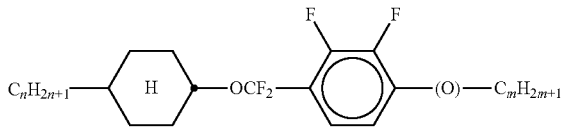
CQIY-n-(O)m
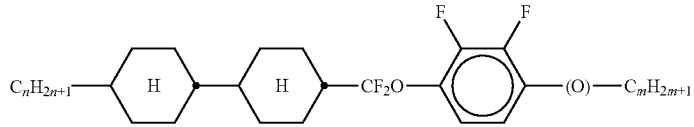
CCQY-n-(O)m
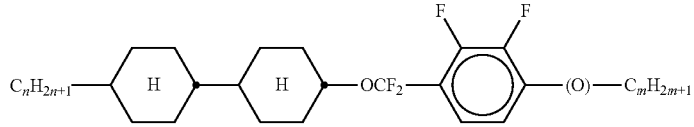
CCQIY-n-(O)m
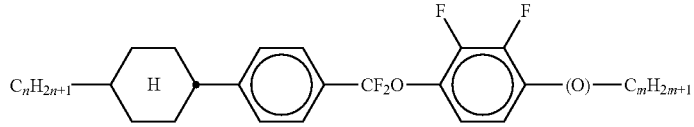
CPQY-n-(O)m TABLE D-continued
Illustrative structures
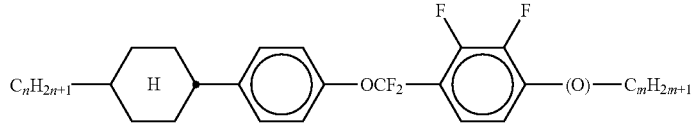
CPQIY-n-Om
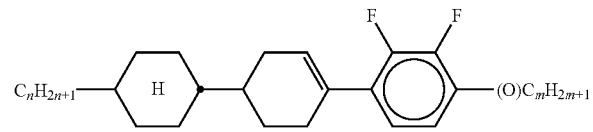
CLY-n-(O)m
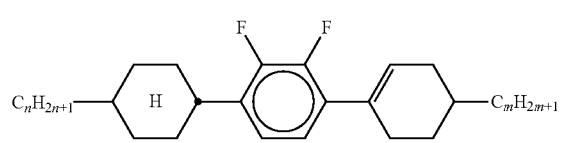
CYLI-n-m
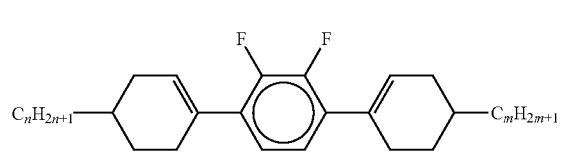
LYLI-n-m
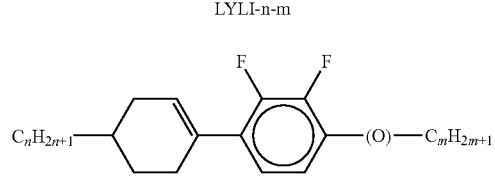
LY-n-(O)m
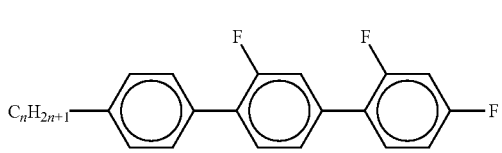
PGIGI-n-F
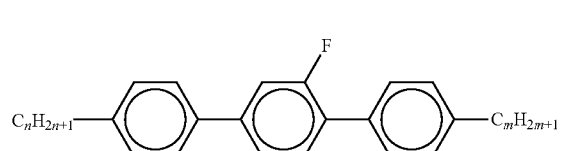
PGP-n-m
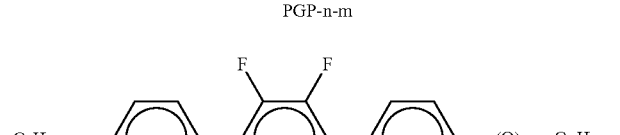
PYP-n-(O)m TABLE D-continued
Illustrative structures
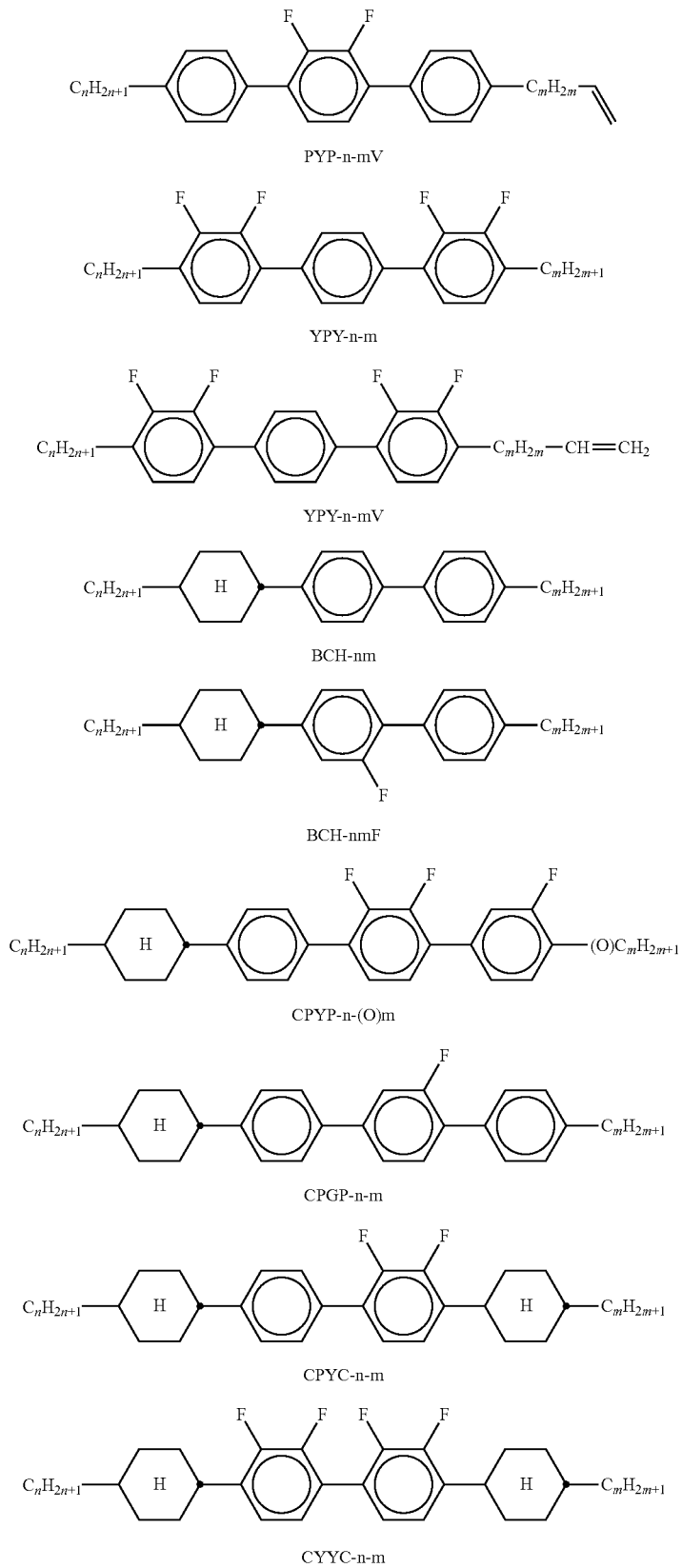

TABLE D-continued
Illustrative structures
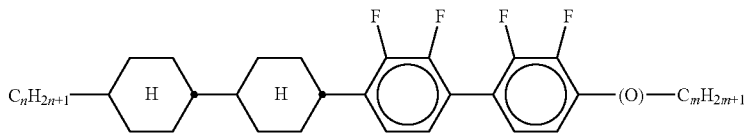
CCYY-n-m
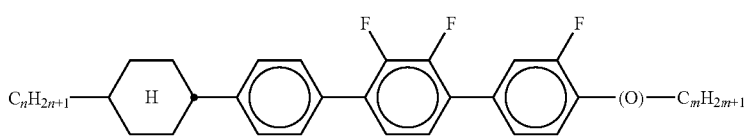
CPYG-n-(O)m
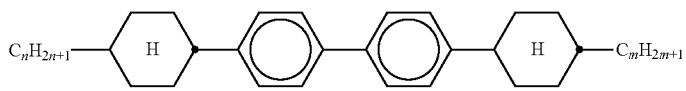
CBC-nm
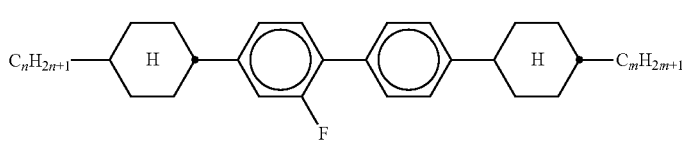
CBC-nmF
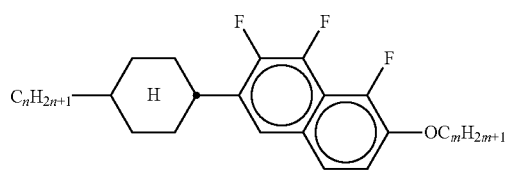
CNap-n-Om
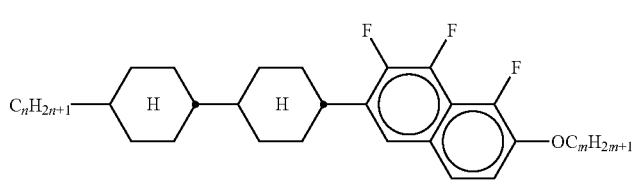
CCNap-n-Om
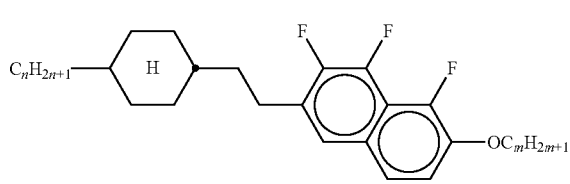
CENap-n-Om
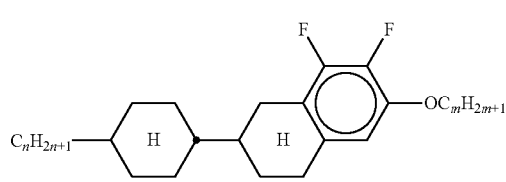
CTNap-n-Om TABLE D-continued
Illustrative structures
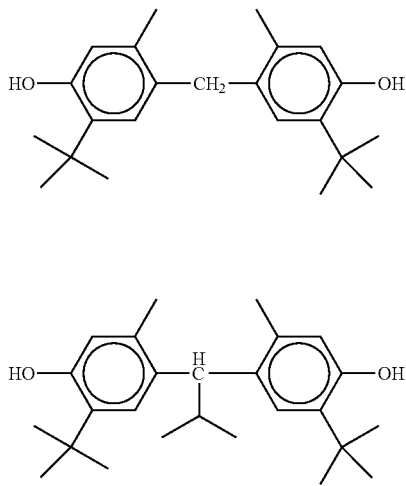
CETNap-n-Om
CK-n-F
DFDBC-n(O)—(O)m
C-DFDBF-n-(O)m
wherein n, m and l preferably, independently of one another, denote 1 to 7.
The following table, Table E, shows illustrative compounds which can be used as additional stabilisers in the mesogenic media according to the present invention.
TABLE E
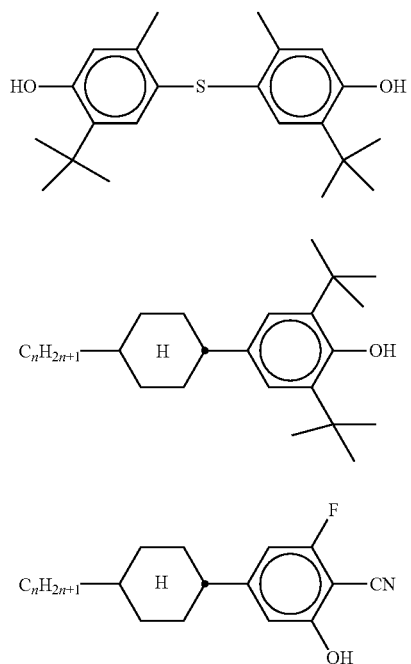
TABLE E-continued TABLE E-continued
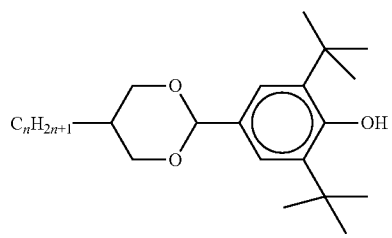
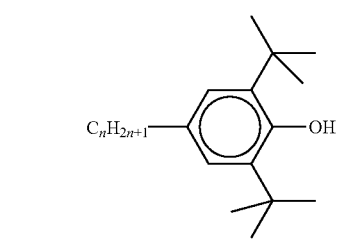
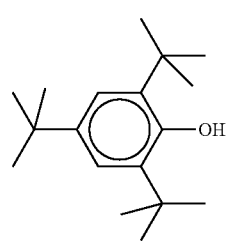
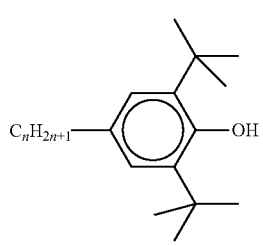
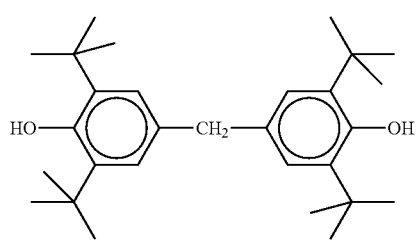
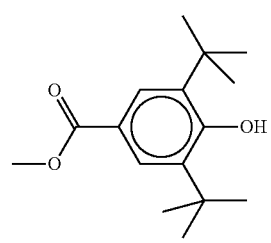
TABLE E-continued
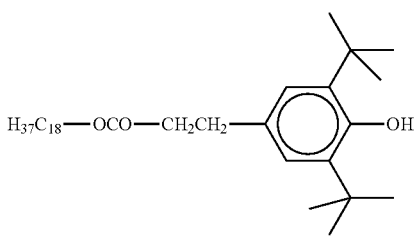
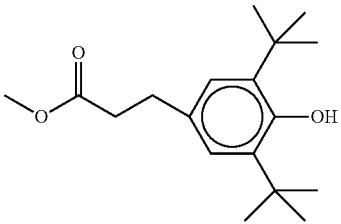
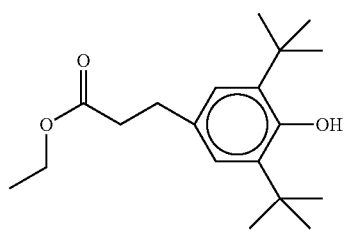
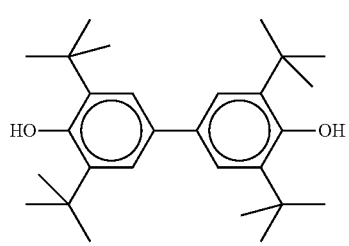
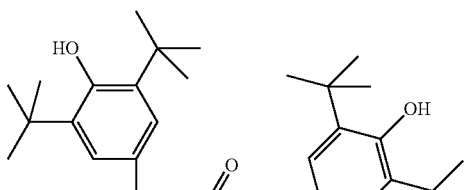
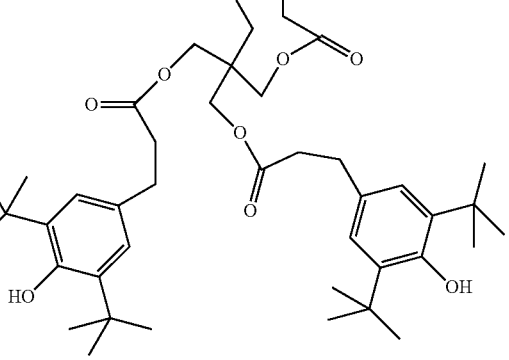

TABLE E-continued
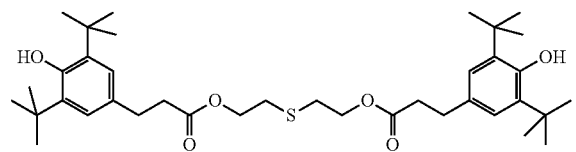 [SMILES: CC(C)(C)c1cc(CCC(=O)OCCSCCOC(=O)CCc2cc(C(C)(C)C)c(O)c(C(C)(C)C)c2)cc(C(C)(C)C)c1O]
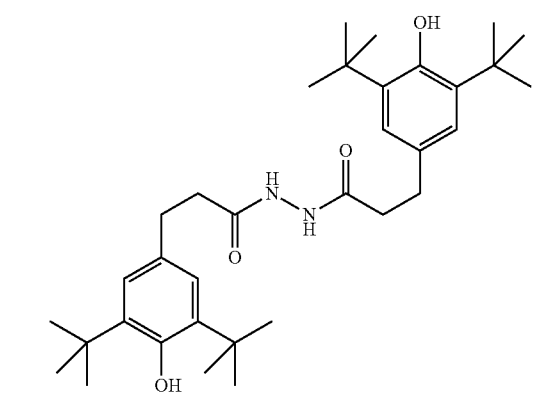 [SMILES: CC(C)(C)c1cc(CCC(=O)NNC(=O)CCc2cc(C(C)(C)C)c(O)c(C(C)(C)C)c2)cc(C(C)(C)C)c1O]
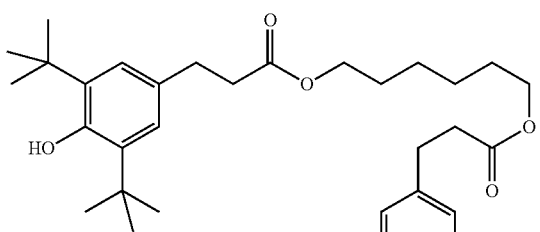
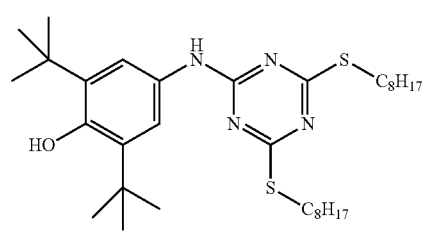
TABLE E-continued
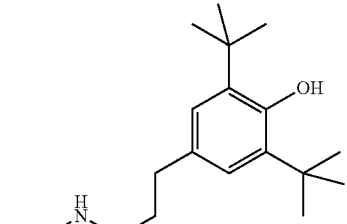
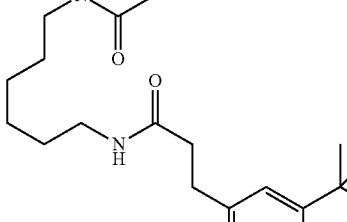
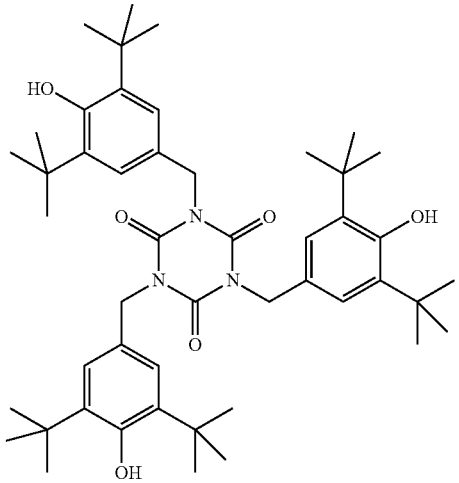 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
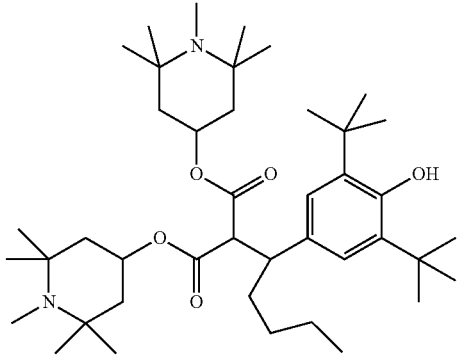 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]

TABLE E-continued
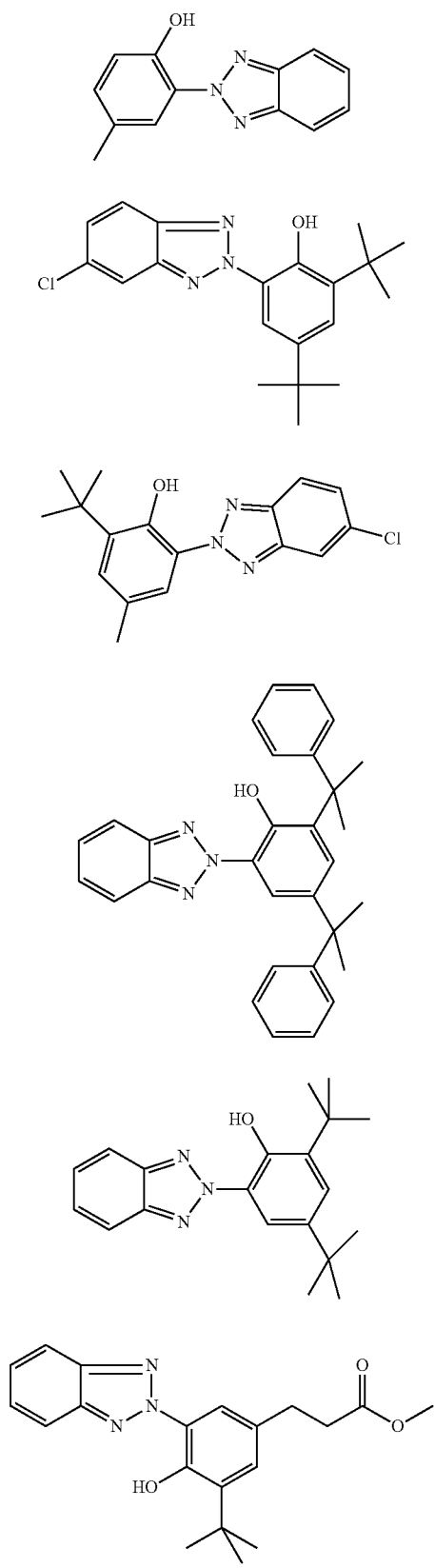
TABLE E-continued
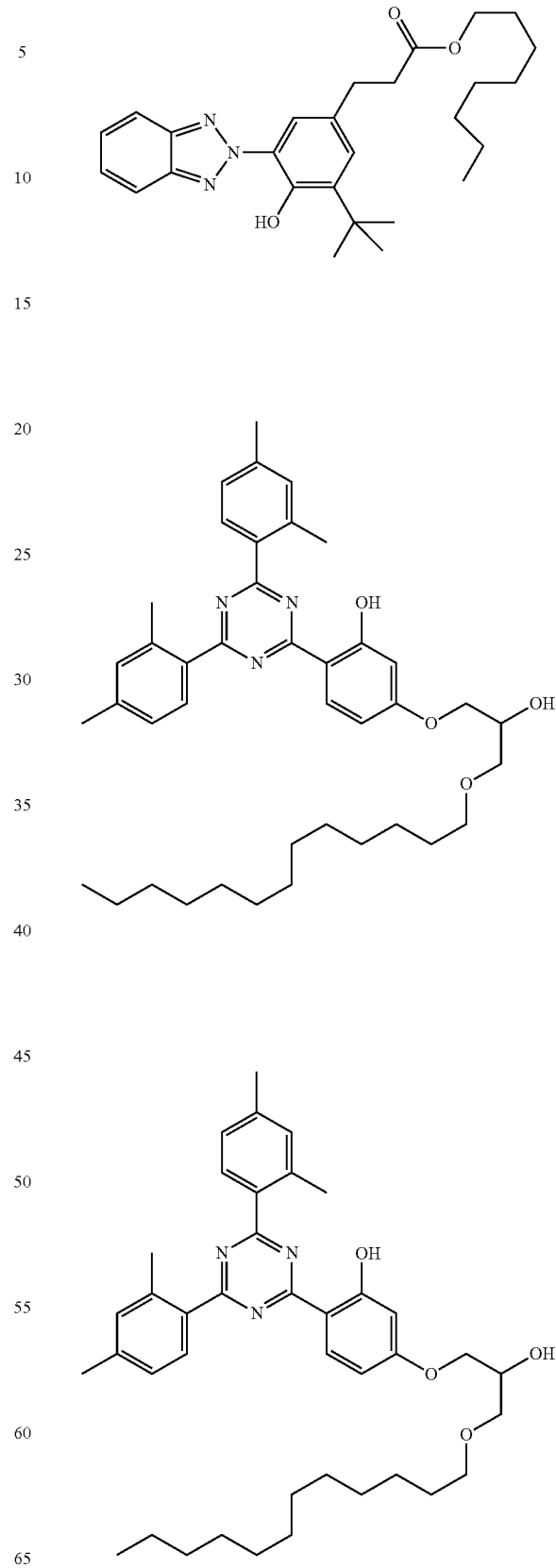

US 10,465,115 B2
125
TABLE E-continued
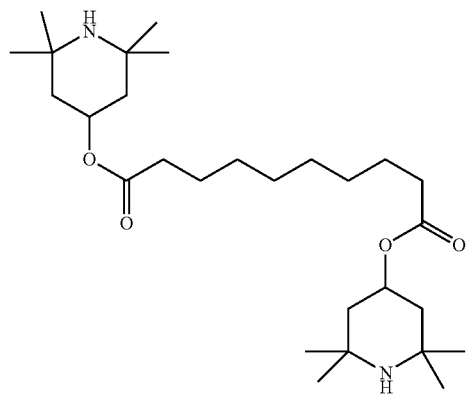
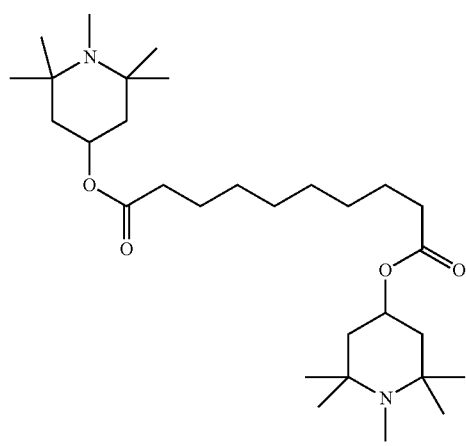
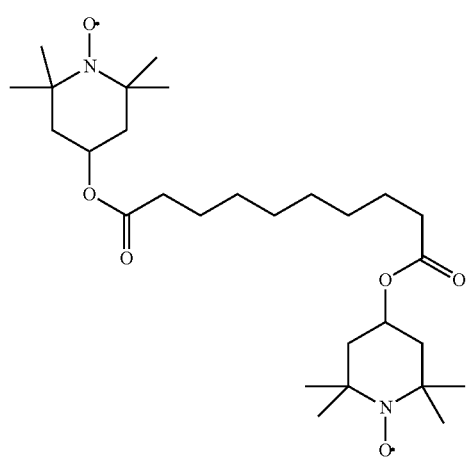
126
TABLE E-continued
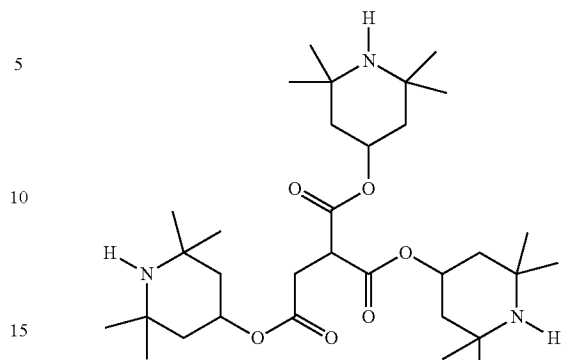
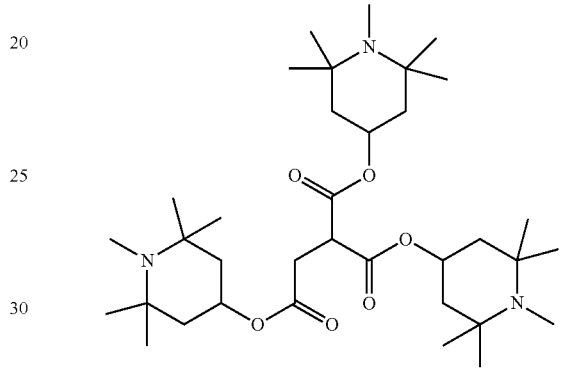
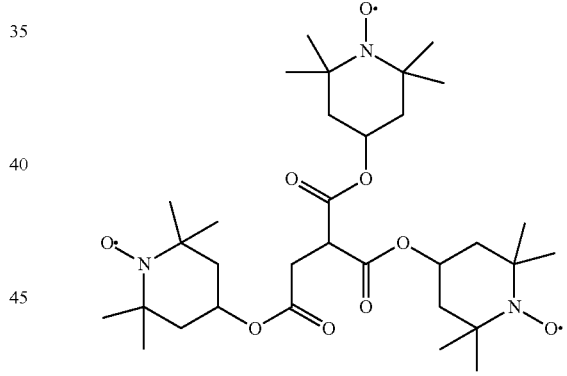
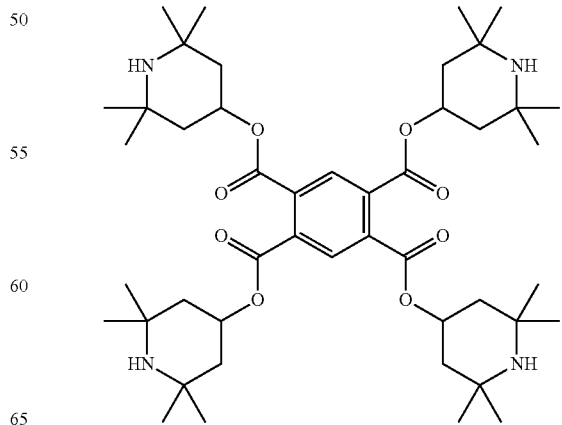

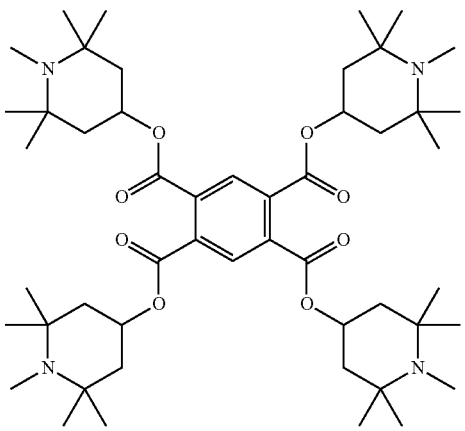

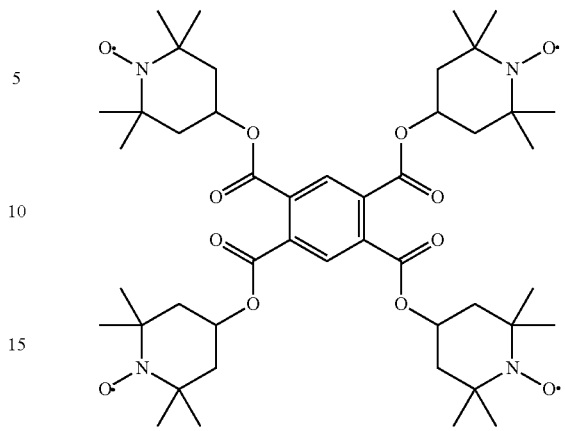

Table E shows possible stabilisers which can be added to the LC media according to the invention.

(n here denotes an integer from 1 to 12, preferably 1, 2, 3, 4, 5, 6, 7 or 8, terminal methyl groups are not shown).

The LC media preferably comprise 0 to 10% by weight, in particular 1 ppm to 5% by weight, particularly preferably 1 ppm to 1% by weight, of stabilisers.

Table F below shows illustrative compounds which can preferably be used as chiral dopants in the mesogenic media according to the present invention.

TABLE F

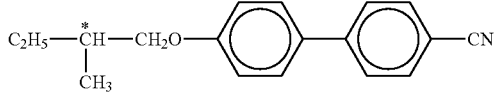

C 15

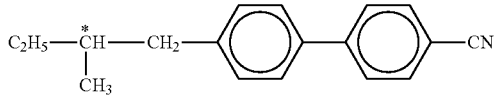

CB 15

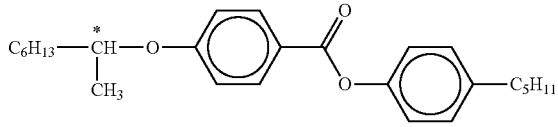

CM 21

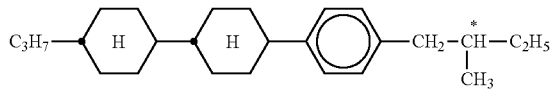

CM 44

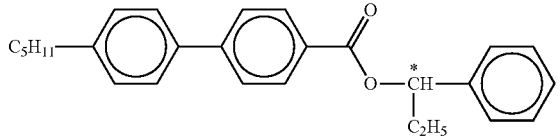

CM 45

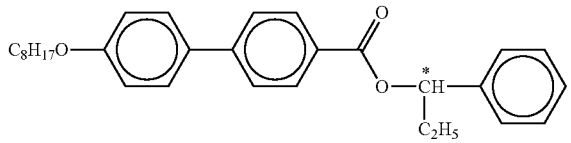

CM 47

TABLE F-continued
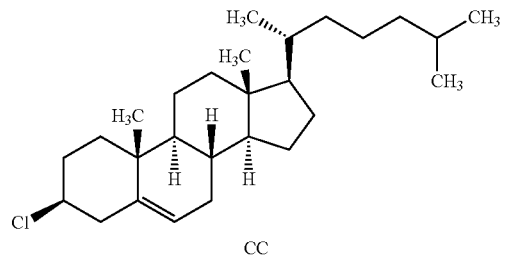
CC
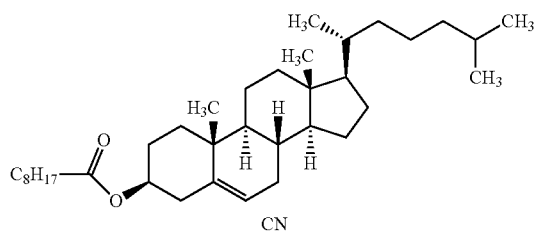
CN
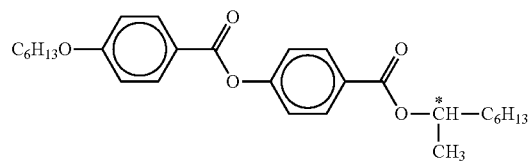
R/S-811
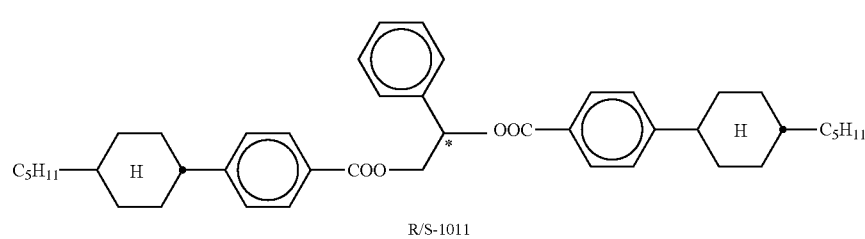
R/S-1011
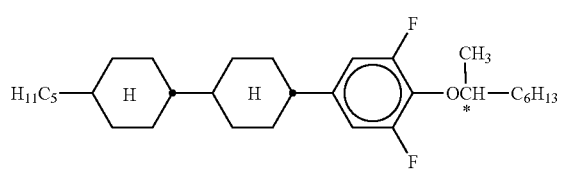
R/S-2011
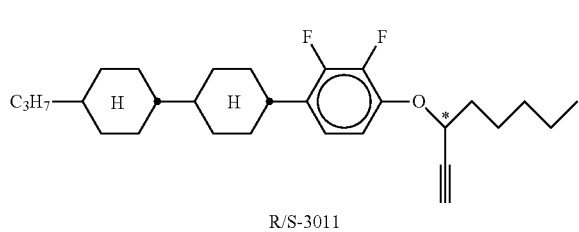
R/S-3011
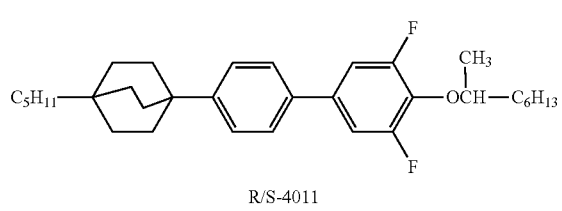
R/S-4011

TABLE F-continued

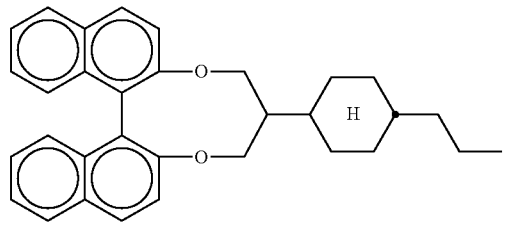

R/S-5011

In a preferred embodiment of the present invention, the mesogenic media comprise one or more compounds selected from the group of the compounds from Table F.

The mesogenic media according to the present application preferably comprise two or more, preferably four or more, compounds selected from the group consisting of the compounds from the above tables.

The liquid-crystal media according to the present invention preferably comprise
- seven or more, preferably eight or more, individual compounds, preferably of three or more, particularly preferably of four or more, different formulae, selected from the group of the compounds from Table D.

EXAMPLES

Hereinafter, the present invention is described in more detail and specifically with reference to the Examples, which however are not intended to limit the present invention.

Synthesis Example 1: Ethyl (E)-3-[3-(2-hydroxyethoxy)-4-(4-pentylbiphenyl)]prop-2-enoate The starting material 2-fluoro-4-iodo-1-(4-pentyl-phenyl)-benzene was prepared according to a literature procedure by Suzuki-coupling of 5-pentylbenzene boronic acid and 4-bromo-2-fluoro-1-iodo-benzene followed by bromine-lithium exchange and reaction of the lithiated intermediate with iodine.

Stage 1: 2-[5-iodo-2-(4-pentylphenyl)phenoxy]ethanol

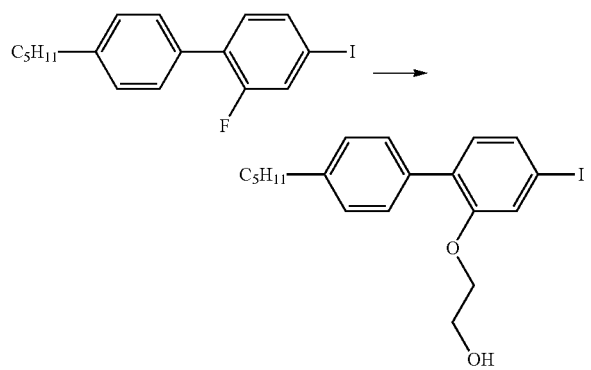

Triethylene glycol dimethyl ether (100 ml), dibenzo-18-crown-6 (1.3 g, 3.6 mmol), and sodium hydride (8 g, 60% dispersion in oil, 200 mmol) are stirred at room temperature. Anhydrous ethylene glycol (40 ml, 720 mmol), is added dropwise over 30 minutes keeping the temperature below 60° C. 2-Fluoro-4-iodo-1-(4-pentyl-phenyl)-benzene (11 g, 30 mmol) is added and the mixture heated to 160° C. over a period of 30 minutes, then stirred overnight at 160° C. The mixture is cooled, water (300 ml) and concentrated hydrochloric acid (20 ml) are added and the mixture is extracted with ethyl acetate (3×100 ml). The combined organic layers are diluted with petrol B.p 40-60° C. (300 ml) and washed with water (400 ml, 2×250 ml). The solvent from the organic layer is removed in vacuo to give an oil. The oil is purified by vacuum flash chromatography on silica with petrol/dichloromethane to give 2-[5-iodo-2-(4-pentylphenyl)phenoxy]-ethanol.

Stage 2: Ethyl (E)-3-[3-(2-hydroxyethoxy)-4-(4-pentylbiphenyl)]prop-2-enoate

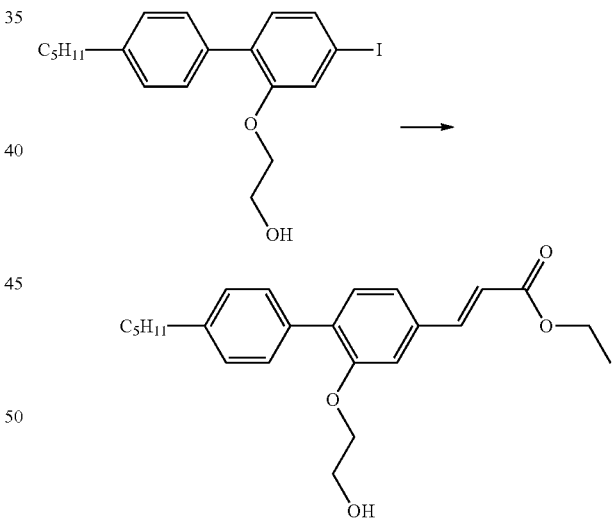

2-[5-iodo-2-(4-pentylphenyl)phenoxy]ethanol (2.0 g, 5.5 mmol), sodium bicarbonate (1.1 g, 13 mmol), tetra-n-butylammonium bromide (1.8 g, 5.6 mmol), ethyl acrylate (2.4 ml, 22 mmol), palladium acetate (62 mg) and dimethylformamide (22 ml) are heated to 100° C. and held for 6 hours. The mixture is cooled, then acidified with dilute hydrochloric acid (60 ml, 1 M, 60 mmol). The mixture is extracted with ethyl acetate (100 ml). The organic layer is washed with water (2×30 ml). The solvent from the organic layer is removed in vacuo. The oil is purified by vacuum flash chromatography on silica (60 g) eluting with the following; petrol B.p 40-60° C.:dichloromethane:ethyl acetate. The solvent is removed in vacuo and the residue is crystallised from heptane (30 ml) to give ethyl (E)-3-[3-(2-hydroxyethoxy)-4-(4-pentylbiphenyl)]prop-2-enoate.

Example 2: Ethyl (E)-3-[4-(4-pentylphenyl)-3-(3-trimethoxysilylpropoxy)-phenyl]prop-2-enoate Step 1: Ethyl (E)-3-[3-allyloxy-4-(4-pentylphenyl)phenyl]prop-2-enoate

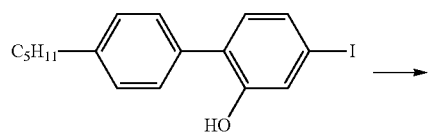

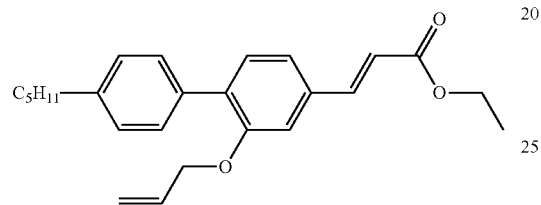

2-Fluoro-4-iodo-1-(4-pentyl-phenyl)-benzene was reacted with sodium hydroxide in triethylene glycol under the same reaction conditions as described in example 1 to give 5-iodo-2-(4-pentylphenyl)phenol. 5-iodo-2-(4-pentylphenyl)phenol (0.5 g, 1.48 mmol), allyl bromide (0.14 ml, 1.62 mmol), potassium carbonate (0.3 g, 2.2 mmol) and butanone (3 ml) were heated at 80° C. for 3 hours. The mixture was cooled and the solvent removed in vacuo. The residue was dissolved in dichloromethane and purified by vacuum flash chromatography on silica (40 g) eluting with dichloromethane. The fractions containing the product were combined and the solvent removed in vacuo to give ethyl (E)-3-[3-allyloxy-4-(4-pentylphenyl)phenyl]prop-2-enoate.

Step 2: Ethyl (E)-3-[4-(4-pentylphenyl)-3-(3-trimethoxysilylpropoxy)-phenyl]prop-2-enoate

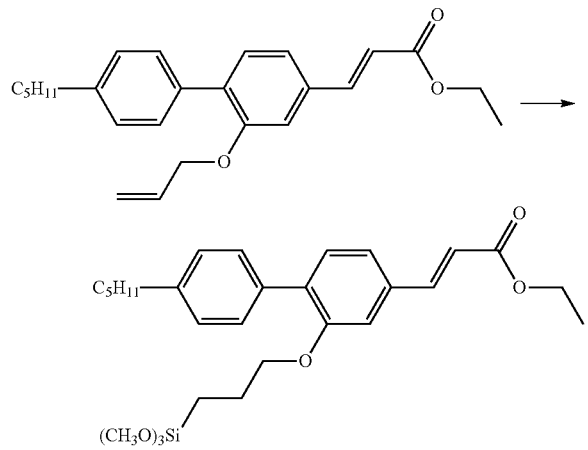

Ethyl (E)-3-[3-allyloxy-4-(4-pentylphenyl)phenyl]prop-2-enoate (0.55 g, 1.46 mmol), trimethoxysilane (0.24 ml, 1.89 mmol), toluene (1 ml), and platinum(0)-1,3-Divinyl-1,1,3,3-tetramethyldisiloxane complex (solution in xylene, 25 mg~2% platinum) were heated at 80° C. overnight. The mixture was cooled, the solvent removed in vacuo and the residue was purified by vacuum flash chromatography on silica (40 g) eluting with toluene:petrol B.p 40-60° C.:dichloromethane:ethyl acetate to give ethyl (E)-3-[4-(4-pentylphenyl)-3-(3-trimethoxysilylpropoxy)-phenyl]prop-2-enoate.

In analogy to the above described procedures the following examples are obtained:

Example 3

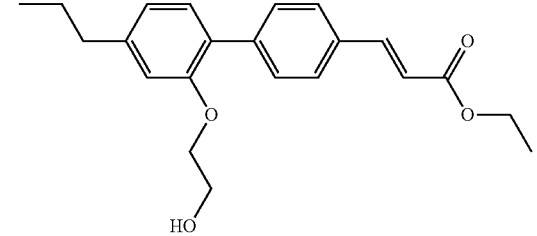 [SMILES: CCCc1ccc(-c2ccc(/C=C/C(=O)OCC)cc2)c(OCCO)c1]

Example 4

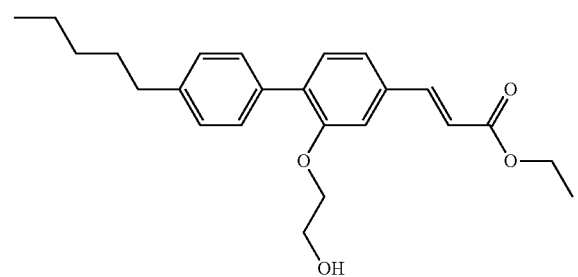 [SMILES: CCCCCc1ccc(-c2ccc(/C=C/C(=O)OCC)cc2OCCO)cc1]

Example 5

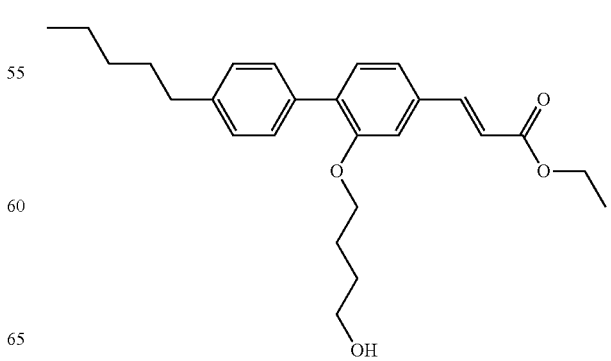

135
Example 6
136
Example 8
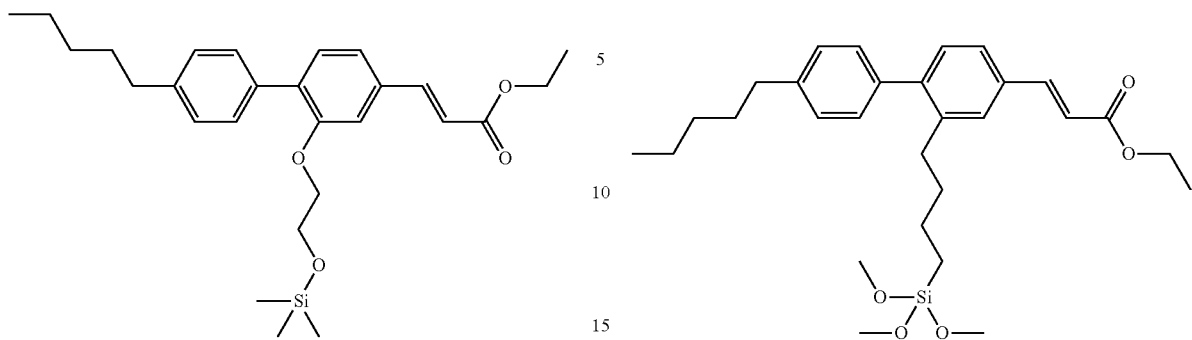
Example 7
Example 9
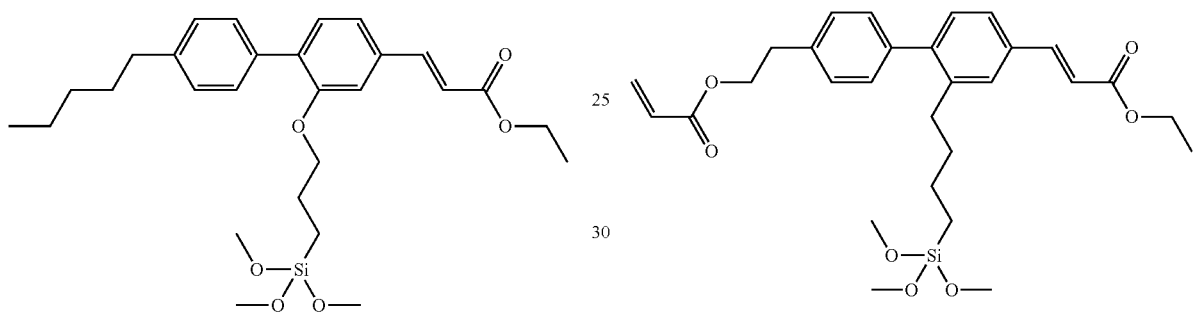
Example 10
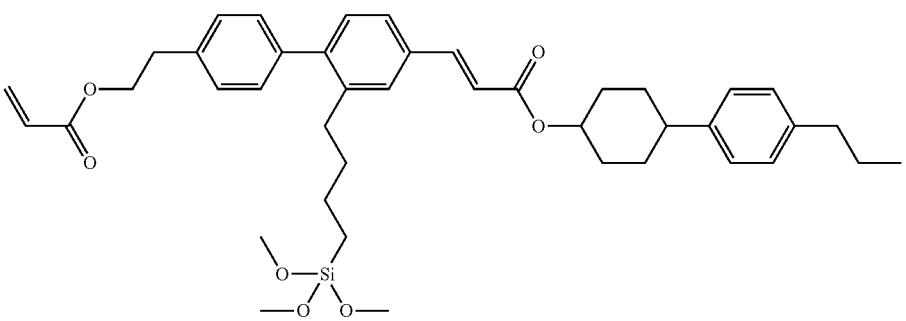 [SMILES: C=CC(=O)OCCc1ccc(-c2ccc(/C=C/C(=O)OC3CCC(c4ccc(CCC)cc4)CC3)cc2CCCC[Si](OC)(OC)OC)cc1]
Example 11
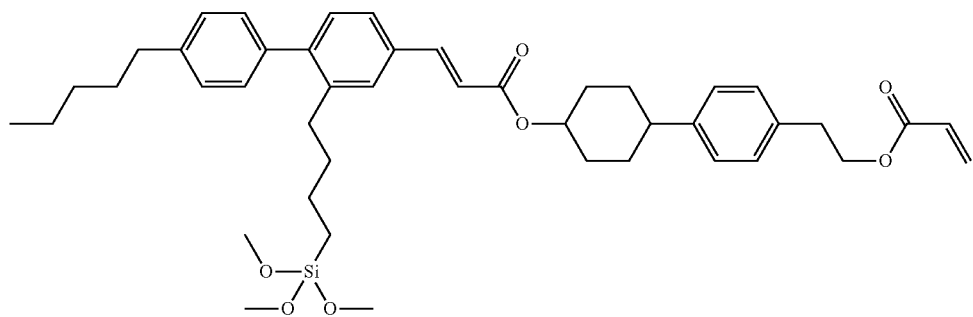 [SMILES: C=CC(=O)OCCc1ccc(C2CCC(OC(=O)/C=C/c3ccc(-c4ccc(CCCCC)cc4)c(CCCC[Si](OC)(OC)OC)c3)CC2)cc1]

Example 12

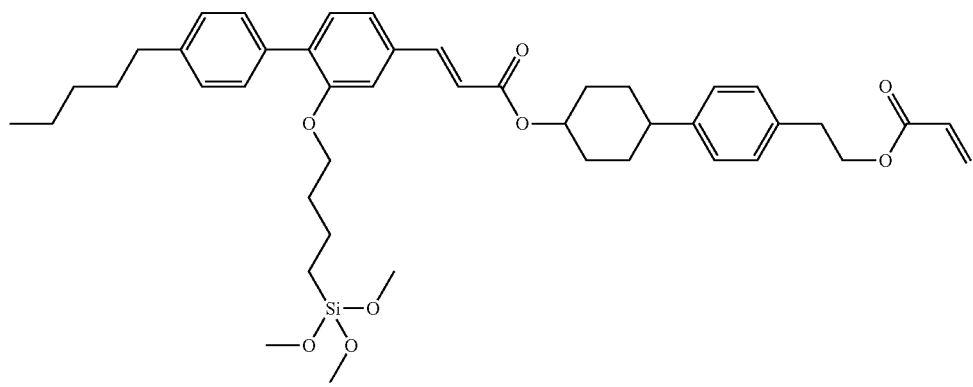 [SMILES: C=CC(=O)OCCc1ccc(C2CCC(OC(=O)/C=C/c3ccc(-c4ccc(CCCCC)cc4)c(OCCCC[Si](OC)(OC)OC)c3)CC2)cc1]

Example 13

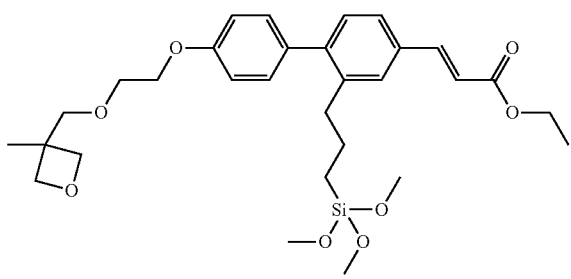 [SMILES: CCOC(=O)/C=C/c1ccc(-c2ccc(OCCOCC3(C)COC3)cc2)c(CCC[Si](OC)(OC)OC)c1]

Fabrication of Display Cells

The display cells are made with raw untreated AF glass using 5 μm spacer beads in Norland 65 adhesive. The cells are assembled by hand and then cured using a high pressure mercury lamp (Omnicure®, 250-450 nm) at 78 mW/cm2 for 60 s.

Cell Filling and Curing

The LC mixtures are capillary filled on a hot plate at 100° C., then left to stand for a further hour at 100° C. and then irradiated with linearly polarised UV light (50 mW/cm²) for 60 s with the wire grid polariser being either perpendicular or parallel to the IPS electrodes which have a 10° offset to the edge of the IPS cell glass. The cells are cooled slowly to room temperature at a cooling rate of 5° C. per minute.

Mixture Examples

A nematic LC host mixture N-1 was prepared as follows:

| Mixture N-1: | | |
|---|---|---|
| Composition Compound | | |
| No. | Abbreviation | c/% |
| 1 | CC-3-V | 37.00 |
| 2 | CCY-3-O1 | 5.00 |
| 3 | CCY-3-O2 | 9.50 |
| 4 | CCY-4-O2 | 5.00 |
| 5 | CPY-2-O2 | 10.00 |
| 6 | CPY-3-O2 | 10.00 |

-continued

| Mixture N-1: | | |
|---|---|---|
| 7 | CY-3-O2 | 11.50 |
| 8 | PY-3-O2 | 12.00 |
| Σ | | 100.0 |
| Physical properties | | |
| T(N, I) = | | 73.5° C. |
| $n_e$ (20° C., 589.3 nm) = | | 1.583 |
| Δn (20° C., 589.3 nm) = | | 0.1005 |
| $\varepsilon_\parallel$ (20° C., 1 kHz) = | | 3.70 |
| Δε (20° C., 1 kHz) = | | -3.65 |
| $k_1$(20° C.) = | | 12.7 |
| $k_3$(20° C.) = | | 14.7 |
| $\gamma_1$ (20° C.) = | | 93 |

A nematic LC host mixture N-2 was prepared as follows:

| Mixture N-2: | | |
|---|---|---|
| Composition Compound | | |
| No. | Abbreviation | c/% |
| 1 | APUQU-2-F | 6.00 |
| 2 | APUQU-3-F | 6.00 |
| 3 | CC-3-V | 44.5 |
| 4 | CC-3-V1 | 4.00 |
| 5 | CCP-3OCF$_3$ | 7.00 |
| 6 | CCP-V-1 | 5.00 |
| 7 | CPGU-3-OT | 3.00 |
| 8 | PGP-2-2V | 5.50 |
| 9 | PGUQU-3-F | 3.00 |
| 10 | PGUQU-4-F | 7.00 |
| 11 | PGUQU-5-F | 3.00 |
| 12 | PUQU-3-F | 6.00 |
| Σ | | 100.0 |
| Physical properties | | |
| T(N, I) = | | 73.5° C. |
| $n_e$ (20° C., 589.3 nm) = | | 1.5902 |
| Δn (20° C., 589.3 nm) = | | 0.1086 |
| $\varepsilon_\parallel$ (20° C., 1 kHz) = | | 12.9 |
| Δε (20° C., 1 kHz) = | | 9.6 |
| $k_1$(20° C.) = | | 12.4 |
| $k_3$(20° C.) = | | 13.8 |
| $\gamma_1$ (20° C.) = | | 67 |

Mixture Example 1

A test display is fabricated according to the procedure described above using 2% of the compound from synthesis example 5 in nematic host mixture N-1. The cell is placed between crossed polarisers on a light table and aligned so that a dark state is achieved. Rotation by 45° gives the bright state. Both dark and bright state appear uniform which proves uniform planar alignment.

Mixture Example 2

A test display is fabricated according to the procedure described above using 2% of the compound from synthesis example 3 in nematic host mixture N-1. The cell is placed between crossed polarisers on a light table and aligned so that a dark state is achieved. Rotation by 45° gives the bright state. Both dark and bright state appear uniform which proves uniform planar alignment.

The change in transmission of the display was measured as follows: The true bright and true dark transmission voltages were measured with parallel polarisers and crossed polarisers respectively, with no cell. The cell was then placed between the crossed polarisers and the transmission voltage was measured with increasing electric field voltage. The relative transmission (% T) was calculated where 100% is defined as "true bright" and 0% is defined as "true dark", using the following equation:

% $T$=100((measured value−true dark)/(true bright−true dark))

The following Table 1 shows the % Transmission values versus the applied voltage.

TABLE 1

| Voltage/V | % T |
|---|---|
| 0 | 1.42 |
| 1 | 1.47 |
| 2 | 4.40 |
| 3 | 16.55 |
| 4 | 32.97 |
| 5 | 44.48 |
| 6 | 49.56 |
| 7 | 50.41 |
| 8 | 49.73 |
| 9 | 47.36 |
| 10 | 45.67 |
| 11 | 43.97 |
| 12 | 42.28 |

As can be seen from table 1, a display fabricated using the mixture from Mixture Example 2 containing the compound from example 1 shows excellent switching behaviour.

Mixture Example 3

A test display is fabricated according to the procedure described above using 2% of the compound from synthesis example 5 in nematic host mixture N-2. The cell is placed between crossed polarisers on a light table and aligned so that a dark state is achieved. Rotation by 45° gives the bright state. Both dark and bright state appear uniform which proves uniform planar alignment.

The invention claimed is:

1. A compound of formula S

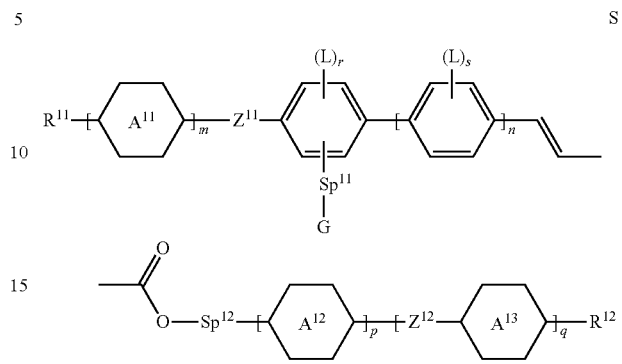

wherein $R^{11}$ and $R^{12}$ identically or differently denote P, P-Sp-, H, F, Cl, Br, I, —CN, —NO$_2$, —NCO, —NCS, —OCN, —SCN, SF$_5$ or straight-chain or branched alkyl having 1 to 25 C atoms, in which, in addition, one or more non-adjacent CH$_2$ groups may each be replaced, independently of one another, by —C(R$^0$)═C(R$^{00}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN, P or P-Sp-, P denotes a polymerisable group, Sp, $Sp^{11}$, $Sp^{12}$ denote a spacer group or a single bond, $A^{11}$, $A^{12}$ and $A^{13}$ on each occurrence, identically or differently, denote an aromatic, alicyclic or heterocyclic group, and which is unsubstituted, or mono- or polysubstituted by L, $Z^{11}$, $Z^{12}$ on each occurrence, identically or differently, denote —O—, —S—, —CO—, —CO—O—, —OCO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH═CH—, —CF═CF—, —C≡C—, —CH═CH—COO—, —OCO—CH═CH—, CR$^0$R$^{00}$ or a single bond, R$^0$ and R$^{00}$ each, independently of one another, denote H or alkyl having 1 to 12 C atoms, n1 is 1, 2, 3 or 4, m is 0, 1 or 2, n is 0 or 1 p is 0 or 1 q is 0, 1 or 2 m+n+p+q is ≤4 r is 0, 1, 2 or 3, s is 0, 1, 2, 3, or 4,

L P, P-Sp-, OH, CH$_2$OH, F, Cl, Br, I, —CN, —NO$_2$, —NCO, —NCS, —OCN, —SCN, —C(═O)N(R$^x$)$_2$, —C(═O)Y$^1$, —C(═O)R$^x$, —N(R$^x$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may be replaced by F, Cl, or P-Sp-, Y$^1$ denotes halogen, R$^x$ denotes P, P-Sp-, H, halogen, straight-chain, branched or cyclic alkyl having 1 to 25 C atoms, in which, in addition, one or more non-adjacent CH$_2$ groups may be replaced by —O—, —S—, —CO—, —CO—O—, —O—CO—, —O—CO—O— in such a way that —O— and/or —S— atoms are not linked directly to one another, and in which, in addition, one or more H atoms may be replaced by F, Cl, P or P-Sp-, an optionally substituted aryl or aryloxy group having 6 to 40 C atoms, or an optionally substituted heteroaryl or heteroaryloxy group having 2 to 40 C atoms, G denotes OH or Si(OR$^{13}$)$_3$, R$^{13}$ denotes straight chain or branched alkyl having 1 to 6 C atoms.

2. The compound of claim 1 selected from the following sub-formulae

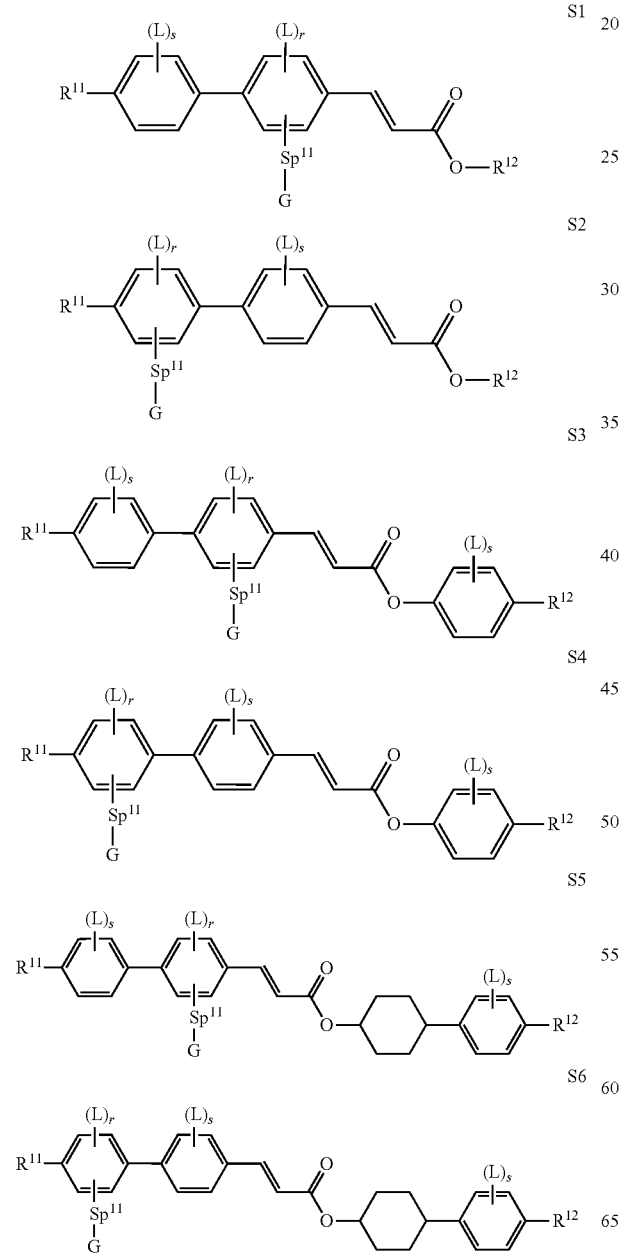

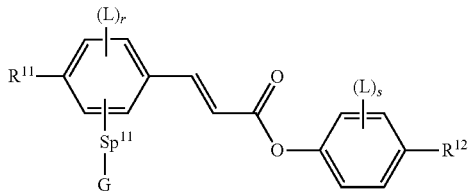

wherein the radicals and parameters have the meaning indicated.

3. The compound of claim 1 wherein G denotes Si(OR$^{13}$)$_3$.

4. The compound of claim 1 wherein G denotes OH.

5. A Liquid crystal mixture, characterised in that it comprises one or more compounds according to claim 1.

6. The liquid crystal mixture according to claim 5, characterised in that the concentration of the compounds of formula S is in the range of from 0.01 to 10% by weight.

7. The liquid crystal mixture according to claim 5, characterised in that it additionally comprises one or more polymerisable compounds of formula P $$P^a\text{-}(Sp^a)_{s1}\text{-}A^2\text{-}(Z^a\text{-}A^1)_{n2}\text{-}(Sp^b)_{s2}\text{-}P^b \qquad P$$

wherein

P$^a$, P$^b$ each, independently of one another, denote a polymerisable group,

Sp$^a$, Sp$^b$ on each occurrence, identically or differently, denote a spacer group, s1, s2 each, independently of one another, denote 0 or 1, A$^1$, A$^2$ each, independently of one another, denote a radical selected from the following groups:
a) the group consisting of trans-1,4-cyclohexylene, 1,4-cyclo-hexenylene and 4,4'-bicyclohexylene, wherein, in addition, one or more non-adjacent CH$_2$ groups may be replaced by —O— and/or —S— and wherein, in addition, one or more H atoms may be replaced by F,
b) the group consisting of 1,4-phenylene and 1,3-phenylene, wherein, in addition, one or two CH groups may be replaced by N and wherein, in addition, one or more H atoms may be replaced by L,
c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may also be mono- or polysubstituted by L,
d) the group consisting of saturated, partially unsaturated or fully unsaturated, and optionally substituted, polycyclic radicals having 5 to 20 cyclic C atoms, one or more of which may, in addition, be replaced by heteroatoms, preferably selected from:

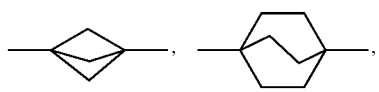

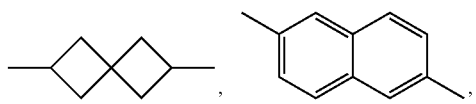

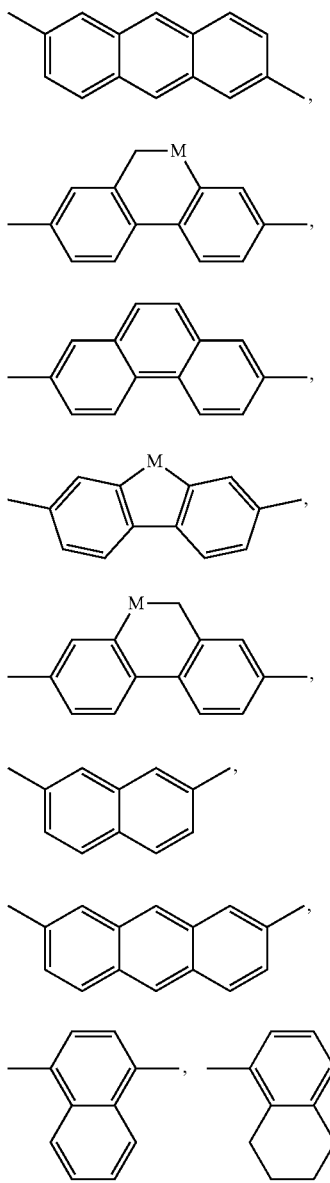

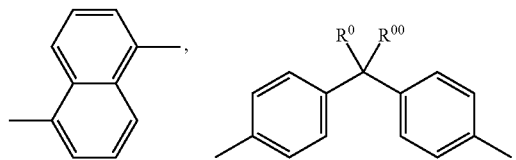

where, in addition, one or more H atoms in these radicals may be replaced by L, and/or one or more double bonds may be replaced by single bonds, and/or one or more CH groups may be replaced by N, n2 denotes 0, 1, 2 or 3, $Z^1$ in each case, independently of one another, denotes —CO—O—, —O—CO—, —CH$_2$O—, —OCH$_2$—, —CF$_2$O—, —OCF$_2$—, or —(CH$_2$)$_n$—, where n is 2, 3 or 4, —O—, —CO—, —C(R$^0$R$^{00}$)—, —CH$_2$CF$_2$—, —CF$_2$CF$_2$— or a single bond, L on each occurrence, identically or differently, denotes F, Cl, CN, SCN, SF$_5$ or straight-chain or branched, in each case optionally fluorinated, alkyl, alkoxy, alkylcarbonyl, alkoxycarbonyl, alkylcarbonyloxy or alkoxycarbonyloxy having up to 12 C atoms, $R^0$, $R^{00}$ each, independently of one another, denote H, F or straight-chain or branched alkyl having 1 to 12 C atoms, wherein, in addition, one or more H atoms may be replaced by F, M denotes —O—, —S—, —CH$_2$—, —CHY$^1$— or —CY$^1$Y$^2$—, and $Y^1$ and $Y^2$ each, independently of one another, have one of the meanings indicated for $R^0$ above or denote Cl or CN.

8. The liquid crystal mixture according to claim 5, characterised in that it comprises one or more compounds selected from the compounds of the formulae P10-1-1 and P10-1-2

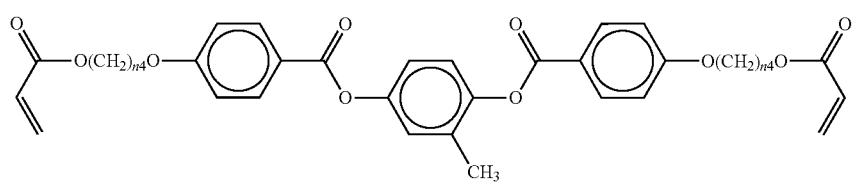

P10-1-1

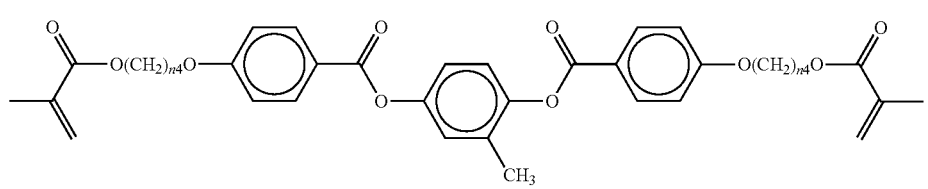

P10-1-2 wherein
n4 denotes an integer between 2 and 10.

9. The liquid crystal mixture according to claim 5, characterised in that it has negative dielectric anisotropy.

10. The liquid crystal mixture of claim 9, characterised in that it comprises one or more compounds selected from the following formulae:

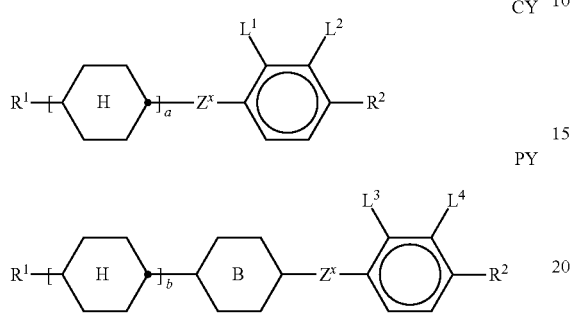

CY

PY wherein the individual radicals have the following meanings:
a denotes 1 or 2,
b denotes 0 or 1,

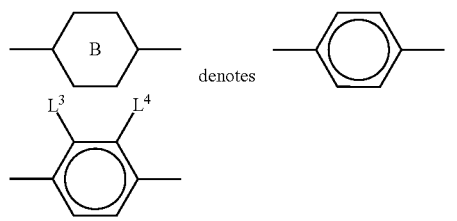

$R^1$ and $R^2$ each, independently of one another, denote alkyl having 1 to 12 C atoms, where, in addition, one or two non-adjacent $CH_2$ groups may be replaced by —O—, —CH=CH—, —CO—, —O—CO— or —CO—O— in such a way that O atoms are not linked directly to one another,
$Z^x$ denotes —CH=CH—, —CH$_2$O—, —OCH$_2$—, —CF$_2$O—, —OCF$_2$—, —O—, —CH$_2$—, —CH$_2$CH$_2$— or a single bond, preferably a single bond,
$L^{1-4}$ each, independently of one another, denote F, Cl, OCF$_3$, CF$_3$, CH$_3$, CH$_2$F, CHF$_2$.

11. The liquid crystal mixture according to claim 5 characterised in that it has positive dielectric anisotropy.

12. The liquid crystal mixture of claim 11, characterised in that it comprises one or more compounds selected from the group of compounds of the formulae II and III,

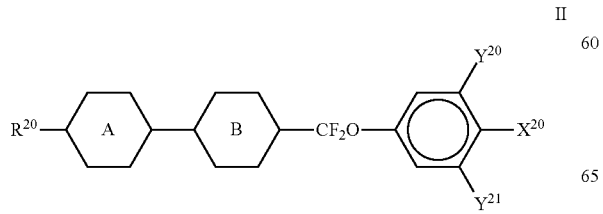

II

-continued

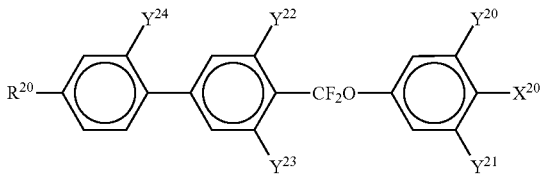

III wherein
$R^{20}$ each, identically or differently, denote a halogenated or unsubstituted alkyl or alkoxy radical having 1 to 15 C atoms, where, in addition, one or more $CH_2$ groups in these radicals may each be replaced, independently of one another, by —C≡C—, —CF$_2$O—, —CH=CH—,

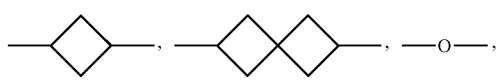

—CO—O— or —O—CO— in such a way that O atoms are not linked directly to one another,
$X^{20}$ each, identically or differently, denote F, Cl, CN, SF$_5$, SCN, NCS, a halogenated alkyl radical, a halogenated alkenyl radical, a halogenated alkoxy radical or a halogenated alkenyloxy radical, each having up to 6 C atoms, and
$Y^{20-24}$ each, identically or differently, denote H or F,

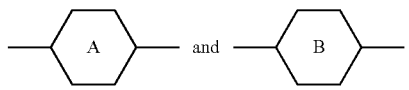

and B each, identically or differently,
denote

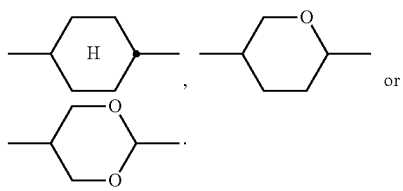

13. The liquid crystal mixture according to claim 11, characterised in that it comprises one or more compounds selected from the group of compounds of the formulae XI and XII

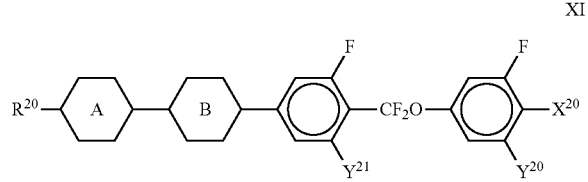

XI

-continued

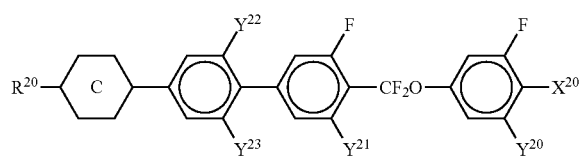

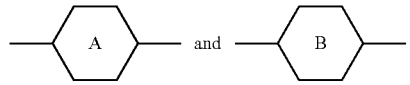

and each, independently of one another, denote

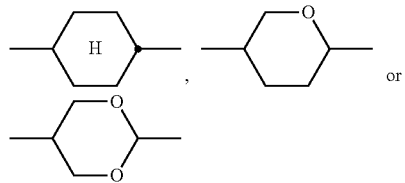

and

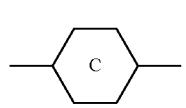

denotes

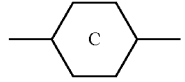

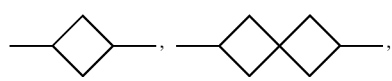

$R^{20}$ each, identically or differently, denote a halogenated or unsubstituted alkyl or alkoxy radical having 1 to 15 C atoms, where, in addition, one or more $CH_2$ groups in these radicals may each be replaced, independently of one another, by —C≡C—, —CF$_2$O—, —CH═CH—, —O—, —CO—O— or —O—CO— in such a way that O atoms are not linked directly to one another, $X^{20}$ each, identically or differently, denote F, Cl, CN, SF$_5$, SCN, NCS, a halogenated alkyl radical, a halogenated alkenyl radical, a halogenated alkoxy radical or a halogenated alkenyloxy radical, each having up to 6 C atoms, and $Y^{20-23}$ each, identically or differently, denote H or F.

14. The liquid crystal mixture according to claim 5 characterised in that it comprises one or more compounds selected from the following formula:

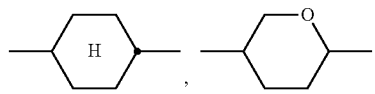

wherein the individual radicals have the following meanings:

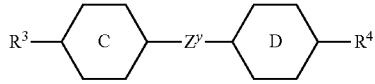

denotes

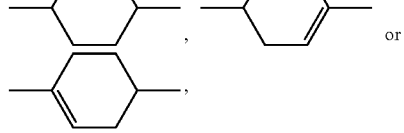

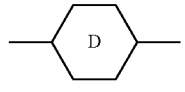

denotes

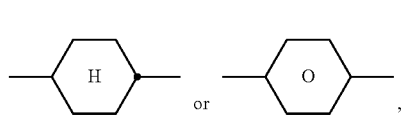

$R^3$ and $R^4$ each, independently of one another, denote alkyl having 1 to 12 C atoms, wherein, in addition, one or two non-adjacent $CH_2$ groups may be replaced by —O—, —CH═CH—, —CO—, —O—CO— or —CO—O— in such a way that O atoms are not linked directly to one another, $Z^y$ denotes —CH$_2$CH$_2$—, —CH═CH—, —CF$_2$O—, —OCF$_2$—, —CH$_2$O—, —OCH$_2$—, —COO—, —OCO—, —C$_2$F$_4$—, —CF═CF— or a single bond.

15. The liquid crystal mixture according to claim 5, characterised in that it comprises one or more compounds selected from the following formulae:

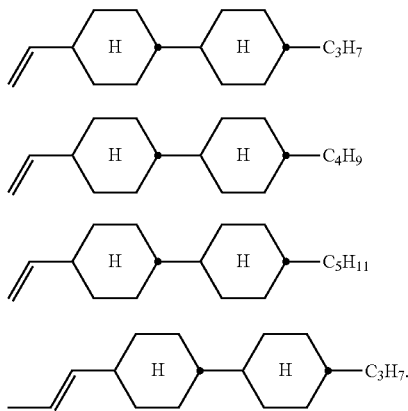

D1a

D1b

D1c

D1d

16. A liquid crystal display, comprising a liquid crystal mixture according to claim 5.

17. A process for the fabrication of a liquid crystal display device, comprising at least the steps:
providing a first substrate which includes a pixel electrode and a common electrode;
providing a second substrate, the second substrate being disposed opposite to the first substrate;
interposing a liquid crystal mixture according to claim 5;
irradiating the liquid crystal mixture with linearly polarised light causing photoalignment of the liquid crystal mixture.

18. The process according to claim 17, characterisd in that after irradiation with polarised light the polymerisable compounds of the liquid crystal mixture are cured by irradiation with ultraviolet light.

19. The process according to claim 17 characterised in that the linearly polarised light is ultraviolet light.

20. A Liquid crystal display, obtainable by a process according to claim 17.

21. The liquid crystal display according to claim 20, wherein the liquid crystal display is an IPS or FFS display.

* * * * *